United States Patent
Hayashi et al.

(10) Patent No.: US 10,559,759 B2
(45) Date of Patent: Feb. 11, 2020

(54) ORGANIC ELECTROLUMINESCENT DEVICE

(71) Applicant: HODOGAYA CHEMICAL CO., LTD., Tokyo (JP)

(72) Inventors: Shuichi Hayashi, Tokyo (JP); Naoaki Kabasawa, Tokyo (JP); Shunji Mochiduki, Tokyo (JP)

(73) Assignee: HODOGAYA CHEMICAL CO., LTD., Tokyo (JP)

( * ) Notice: Subject to any disclaimer, the term of this patent is extended or adjusted under 35 U.S.C. 154(b) by 269 days.

(21) Appl. No.: 15/541,432

(22) PCT Filed: Jan. 5, 2016

(86) PCT No.: PCT/JP2016/050063
§ 371 (c)(1),
(2) Date: Jul. 3, 2017

(87) PCT Pub. No.: WO2016/111269
PCT Pub. Date: Jul. 14, 2016

(65) Prior Publication Data
US 2017/0358754 A1    Dec. 14, 2017

(30) Foreign Application Priority Data

Jan. 8, 2015    (JP) .................................. 2015-001991

(51) Int. Cl.
*H01L 51/50*    (2006.01)
*H01L 51/00*    (2006.01)
(Continued)

(52) U.S. Cl.
CPC ........ *H01L 51/0059* (2013.01); *C07C 211/54* (2013.01); *C07C 211/61* (2013.01);
(Continued)

(58) Field of Classification Search
None
See application file for complete search history.

(56) References Cited

U.S. PATENT DOCUMENTS

| 5,639,914 A | 6/1997 | Tomiyama et al. |
| 5,707,747 A | 1/1998 | Tomiyama et al. |

(Continued)

FOREIGN PATENT DOCUMENTS

| CN | 103087065 A | 5/2013 |
| CN | 103956434 A | 7/2014 |

(Continued)

OTHER PUBLICATIONS

International Search Report issued in WIPO Patent Application No. PCT/JP2016/050063, dated Mar. 22, 2016.
(Continued)

*Primary Examiner* — Gregory D Clark
(74) *Attorney, Agent, or Firm* — Greenblum & Bernstein, P.L.C.

(57) ABSTRACT

The organic EL device of the present invention has an anode, a first hole transport layer, a second hole transport layer, a luminous layer, an electron transport layer, and a cathode in the order of description. The second hole transport layer includes an arylamine derivative represented by the following general formula (1):

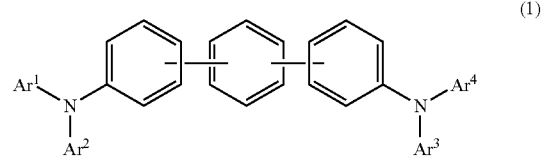

(1)

(Continued)

9 CATHODE
8 ELECTRON INJECTION LAYER
7 ELECTRON TRANSPORT LAYER
6 LUMINOUS LAYER
5 SECOND HOLE TRANSPORT LAYER
4 FIRST HOLE TRANSPORT LAYER
3 HOLE INJECTION LAYER
2 TRANSPARENT ANODE
1 GLASS SUBSTRATE and the electron transport layer includes a pyrimidine compound represented by the following general formula (2):

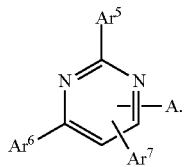

(2)

6 Claims, 48 Drawing Sheets

(51) Int. Cl.
    C09K 11/06      (2006.01)
    C07C 211/54     (2006.01)
    C07C 211/61     (2006.01)
    C07D 209/08     (2006.01)
    H01L 51/52      (2006.01)

(52) U.S. Cl.
    CPC ............ C07D 209/08 (2013.01); C09K 11/06
            (2013.01); H01L 51/006 (2013.01); H01L
            51/0052 (2013.01); H01L 51/0054 (2013.01);
            H01L 51/0058 (2013.01); H01L 51/0061
            (2013.01); H01L 51/0067 (2013.01); H01L
            51/0072 (2013.01); H01L 51/0077 (2013.01);
            C07C 2603/18 (2017.05); C07C 2603/42
            (2017.05); C09K 2211/1007 (2013.01); C09K
            2211/1011 (2013.01); C09K 2211/1014
            (2013.01); C09K 2211/1018 (2013.01); H01L
            51/5016 (2013.01); H01L 51/5064 (2013.01);
            H01L 51/5072 (2013.01); H01L 51/5206
            (2013.01); H01L 51/5221 (2013.01)

(56)              References Cited

U.S. PATENT DOCUMENTS

| 5,792,557 | A  | 8/1998  | Nakaya et al. |
| 7,759,030 | B2 | 7/2010  | Abe et al. |
| 7,799,492 | B2 | 9/2010  | Abe et al. |
| 8,021,764 | B2 | 9/2011  | Hwang et al. |
| 8,021,765 | B2 | 9/2011  | Hwang et al. |
| 8,188,315 | B2 | 5/2012  | Hwang et al. |
| 8,394,510 | B2 | 3/2013  | Mizuki et al. |
| 8,895,159 | B2 | 11/2014 | Mizuki et al. |
| 8,974,922 | B2 | 3/2015  | Hwang et al. |
| 9,478,754 | B2 | 10/2016 | Hwang et al. |
| 2004/0170863 | A1* | 9/2004 | Kim ................ C07C 13/72 428/690 |
| 2009/0091244 | A1 | 4/2009 | Negishi et al. |
| 2010/0052526 | A1 | 3/2010 | Je |
| 2010/0244008 | A1* | 9/2010 | Lee ................ C07D 409/10 257/40 |
| 2013/0112946 | A1 | 5/2013 | Park et al. |
| 2013/0193414 | A1* | 8/2013 | Werner ............ C09K 11/06 257/40 |
| 2013/0328040 | A1* | 12/2013 | Yokoyama ........ C09K 11/06 257/40 |
| 2015/0034923 | A1* | 2/2015 | Kim ................ H01L 51/5044 257/40 |
| 2015/0236264 | A1 | 8/2015 | Kim et al. |
| 2015/0380657 | A1* | 12/2015 | Yokoyama ........ H01L 51/0059 257/40 |
| 2016/0118591 | A1 | 4/2016 | Yokoyama et al. |
| 2016/0126464 | A1 | 5/2016 | Yokoyama et al. |
| 2017/0005273 | A1 | 1/2017 | Hwang et al. |

FOREIGN PATENT DOCUMENTS

| JP | 8-48656 | 2/1996 |
| JP | 3194657 | 6/2001 |
| JP | 2006-151979 | 6/2006 |
| JP | 2007-191465 | 8/2007 |
| JP | 4943840 | 3/2012 |
| KR | 10-2010-0024894 | 3/2010 |
| WO | 2008/062636 | 5/2008 |
| WO | 2014/129201 | 8/2014 |
| WO | 2014199567 A1 | 12/2014 |
| WO | 2015/004875 | 1/2015 |
| WO | 2015/190400 | 12/2015 |

OTHER PUBLICATIONS

Chinese Office Action issued with respect to Application No. 201680014293.6, dated Sep. 4, 2018.

European Search Report issued with respect to Application No. 16735008.1, dated Jul. 12, 2018.

* cited by examiner

9 CATHODE
8 ELECTRON INJECTION LAYER
7 ELECTRON TRANSPORT LAYER
6 LUMINOUS LAYER
5 SECOND HOLE TRANSPORT LAYER
4 FIRST HOLE TRANSPORT LAYER
3 HOLE INJECTION LAYER
2 TRANSPARENT ANODE
1 GLASS SUBSTRATE (1-28)

(1-29)

(1-30)

(1-31)

(1-32)

(1-33)

(1-47)

(1-48)

(1-49)

(1-50)

(1-51)

(1-52)

(1-53)

(1-54)

(1-55)

(1-56)

(1-57)

(1-58)

(1-59)

(1-60)

(1-61)

(1-62)

(1-63)

(1-64)

(4-1)
(4-2)
(4-3)
(4-4)
(4-5)
(4-6)

(4-12)

(4-13)

(4-14)

(4-15)

(4-16)

(4-17)

(4'-1)

(4'-2)

(5-1)

(5-2)

(5-3)

(5-4)

(5-5)

(5-17)

(5-18)

(5-19)

(5-20)

(5-21)

(5-22)

(5-23)

(5'-1)

(5'-2)

(2-14)

(2-15)

(2-16)

(2-17)

(2-18)

(2-19)

(2-32)

(2-33)

(2-34)

(2-35)

(2-36)

(2-37)

(2-38)

(2-39)

(2-40)

(2-41)

(2-42)

(2-43)

(2-44)

(2-45)

(2-46)

(2-68)

(2-69)

(2-70)

(2-71)

(2-72)

(2-78)

(2-79)

(2-80)

(2-81)

(2-82)

(2-83)

(2-84)

(2-85)

(2-86)

(2-87)

(2-93)

(2-94)

(2-95)

(2-96)

(2-102)

(2-103)

(2-104)

(2-105)

(2-106)

(2-107)

(2-108)

(2-109)

(2-110)

(2-111)

(2-121)

(2-122)

(2-123)

(2-124)

(2-125)

ORGANIC ELECTROLUMINESCENT DEVICE

TECHNICAL FIELD

The present invention relates to an organic electroluminescence device (organic EL device), which is a self light-emitting device suitable for various display devices, and more particularly to an organic EL device including a specific arylamine compound and a specific pyrimidine compound.

BACKGROUND ART

An organic EL device is a self light-emitting device, and is thus brighter, better in visibility, and capable of clearer display, than a liquid crystal device. Hence, active researches have been conducted on organic EL devices.

In 1987, C. W. Tang et al. of Eastman Kodak Company developed a laminated structure device sharing various roles for light emission among different materials, thereby imparting practical applicability to organic EL devices. The developed organic EL device is configured by laminating a layer of a fluorescent body capable of transporting electrons, and a layer of an organic substance capable of transporting holes. As a result of injecting positive charges and negative charges into the layer of the fluorescent body to perform light emission, it is possible to obtain a high luminance of 1000 $cd/m^2$ or higher at a voltage of 10 V or less.

Many improvements have been heretofore made to put the organic EL devices to practical use. It is generally well known that high efficiency and durability can be achieved by an electroluminescence device having a laminated structure, in which the roles to be played by respective layers are further segmented, i.e., having an anode, a hole injection layer, a hole transport layer, a luminous layer, an electron transport layer, an electron injection layer, and a cathode on a substrate.

For further increase in the luminous efficiency, it has been attempted to utilize triplet excitons, and the utilization of phosphorescent luminous compounds has been investigated.

Furthermore, devices utilizing light emission by thermally activated delayed fluorescence (TADF) have been developed. For example, in 2011, Adachi et al. from Kyushu University have realized an external quantum efficiency of 5.3% with a device using a thermally activated delayed fluorescence material.

The luminous layer can also be prepared by doping a charge transport compound, generally called a host material, with a fluorescent compound, a phosphorescent luminous compound, or a material radiating delayed fluorescence. The selection of the organic material in the organic EL device greatly affects the characteristics of the device, such as efficiency and durability.

With the organic EL device, the charges injected from both electrodes recombine in the luminous layer, thereby producing light emission, and how efficiently the charges of the holes and the electrons are passed on to the luminous layer is of importance, and a device that exhibits excellent carrier balance is required. Further, by enhancing hole injection property or increasing electron blocking property, that is, property to block electrons injected from the cathode, it is possible to increase the probability of holes and electrons recombining. Besides, excitons generated in the luminous layer are confined. By so doing, it is possible to obtain a high luminous efficiency. Therefore, the role of the hole transport material is important, and a demand has been created for a hole transport material having high hole injection property, high hole mobility, high electron blocking property, and high durability to electrons.

Further, from the viewpoint of device life, heat resistance and amorphousness of the materials are also important. A material with a low heat resistance is thermally decomposed even at a low temperature by heat produced during device driving, and the material deteriorates. In a material with low amorphousness, crystallization of a thin film occurs even in a short time, and the device deteriorates. Thus, high heat resistance and satisfactory amorphousness are required of the materials to be used.

N,N'-diphenyl-N,N'-di(α-naphthyl)benzidine (NPD) and various aromatic amine derivatives are known as hole transport materials which have been heretofore used in organic EL devices (see, for example, PTL 1 and PTL 2). NPD has satisfactory hole transport capability, but the glass transition temperature (Tg), which is an indicator of heat resistance, is as low as 96° C. and device characteristics degrade due to crystallization under high-temperature conditions.

Further, among the aromatic amine derivatives, there are also compounds with an excellent hole mobility of $10^{-3}$ $cm^2/Vs$ or higher (see, for example, PTL 1 and PTL 2). Since electron blocking property is insufficient, however, some of electrons pass through the luminous layer, and no increase in luminous efficiency can be expected. Thus, materials with better electron blocking property, higher stability of a thin film, and high heat resistance are needed to increase further the efficiency.

An aromatic amine derivative with high durability has also been reported (see, for example, PTL 3), but this derivative is used as a charge transport material for use in an electrophotographic photosensitive body and there is no example of application to an organic EL device.

Arylamine compounds having a substituted carbazole structure have been suggested as compounds with improved properties such as heat resistance and hole injection property (see, for example, PTL 4 and PTL 5). Although heat resistance, luminous efficiency, and the like of devices using these compounds for a hole injection layer or hole transport layer have been improved, the results are still insufficient and further decrease in a driving voltage and increase in luminous efficiency are needed.

Devices in which holes and electrons can recombine with a high efficiency and which have a high luminous efficiency, a low driving voltage, and a long life need to be provided by combining materials with excellent hole and electron injection-transport performance and stability and durability of a thin film so as to improve device characteristics of organic EL devices and increase the yield in device production.

Further, devices which have carrier balance, a high efficiency, a low driving voltage, and a long life need to be provided by combining materials with excellent hole and electron injection-transport performance and stability and durability of a thin film so as to improve device characteristics of organic EL devices.

CITATION LIST

Patent Literature

PTL 1: Japanese Patent Application Publication No. H8-048656
PTL 2: Japanese Patent No. 3194657
PTL 3: Japanese Patent No. 4943840
PTL 4: Japanese Patent Application Publication No. 2006-151979
PTL 5: WO 2008-62636

SUMMARY OF INVENTION

Technical Problem

It is an object of the present invention to provide an organic EL device which has a high efficiency, a low driving voltage, and a particularly long life by combining materials for an organic EL device with excellent hole and electron injection-transport performance, electron blocking capability, and stability and durability in a thin-film state so as to demonstrate effectively the properties possessed by each material.

Means for Solving the Problem

The inventors of the present invention found that an organic EL device in which excellent carrier balance is ensured and which excels in various characteristics can be obtained when a hole transport layer has a two-layer structure including a first hole transport layer and a second hole transport layer, the second hole transport layer adjacent to a luminous layer includes an arylamine derivative having a specific molecular structure, and an electron transport layer includes a pyrimidine compound having a specific molecular structure. As a result, the inventors have accomplished the present invention.

According to the present invention, there is provided an organic electroluminescence device having an anode, a first hole transport layer, a second hole transport layer, a luminous layer, an electron transport layer, and a cathode in the order of description, wherein the second hole transport layer includes an arylamine derivative represented by the following general formula (1), and the electron transport layer includes a pyrimidine compound represented by the following general formula (2).

The arylamine derivative;

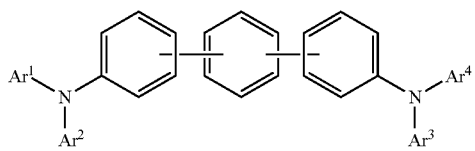
(1)

in this formula,
$Ar^1$ to $Ar^4$ each represent an aromatic hydrocarbon group or an aromatic heterocyclic group.

The pyrimidine compound;

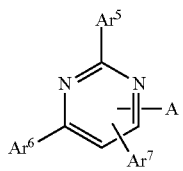
(2)

in this formula,
$Ar^5$ represents an aromatic hydrocarbon group or an aromatic heterocyclic group;

$Ar^6$ and $Ar^7$ each represent a hydrogen atom, an aromatic hydrocarbon group, or an aromatic heterocyclic group; $Ar^6$ and $Ar^7$ may not each be a hydrogen atom at the same time;

A represents a monovalent organic group represented by the following general formula (3):

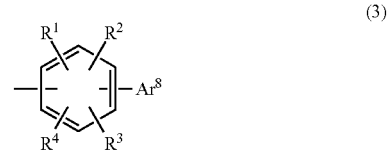
(3)

in this formula,
$Ar^8$ represents an aromatic heterocyclic group;

$R^1$ to $R^4$ each represent a hydrogen atom, a deuterium atom, a fluorine atom, a chlorine atom, a cyano group, a trifluoromethyl group, an alkyl group having 1 to 6 carbon atoms, an aromatic hydrocarbon group, or an aromatic heterocyclic group; any of $R^1$ to $R^4$ may be bonded to $Ar^8$ via a single bond, an oxygen atom, a sulfur atom, or an optionally substituted methylene group to form a ring.

In the organic EL device of the present invention, it is preferred that the first hole transport layer include an arylamine compound having hole transport property and having a molecular structure different from that of the arylamine derivative included in the second hole transport layer.

The arylamine compound included in the first hole transport layer is preferably:

(1) a poly(triarylamine) compound having a structure which has 3 to 6 triarylamine skeletons, the triarylamine skeletons being linked to each other via a single bond or a divalent group having no heteroatom; or (2) a di(triarylamine) compound having a structure which has two triarylamine skeletons in a molecule, the triarylamine skeletons being linked to each other via a single bond or a divalent group having no heteroatom.

Further, it is preferred that the poly(triarylamine) compound be represented by the following general formula (4);

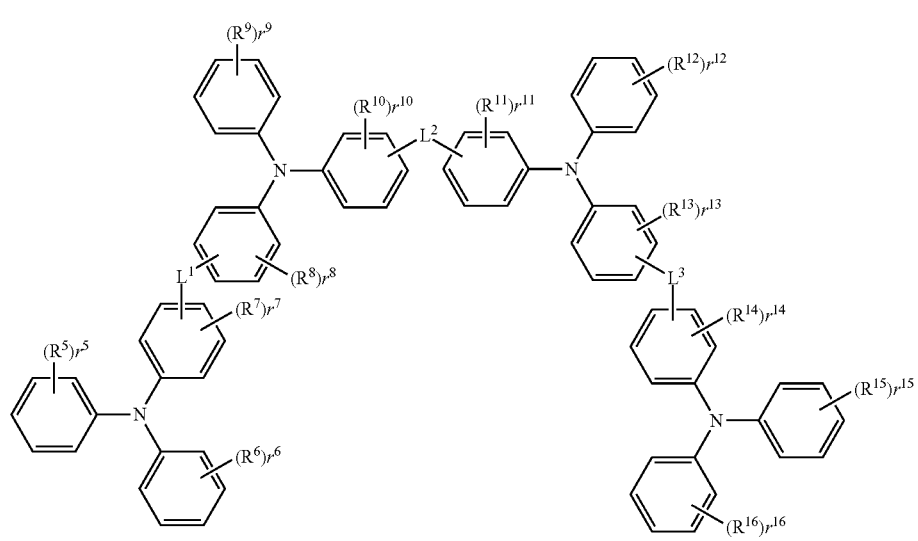
(4)

in this formula, $r^5$ to $r^{16}$ each represent an integer indicating the number of substituents $R^5$ to $R^{16}$ bonded to aromatic rings; $r^5$, $r^6$, $r^9$, $r^{12}$, $r^{15}$, and $r^{16}$ each represent an integer of 0 to 5; $r^7$, $r^8$, $r^{10}$, $r^{11}$, $r^{13}$, and $r^{14}$ each represent 0 or an integer of 1 to 4;

$R^5$ to $R^{16}$ each represent a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, an aromatic hydrocarbon group, an aromatic heterocyclic group, an aralkyl group, or an aryloxy group; when a plurality of $R^5$ to $R^{16}$ is bonded to the same benzene ring, the plurality of present groups may be bonded to each other via a single bond, an oxygen atom, a sulfur atom, or an optionally substituted methylene group to form a ring; and $L^1$, $L^2$, and $L^3$ each represent a single bond or a divalent organic group represented by the following formulas (B) to (G);

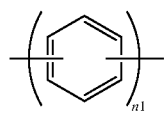

(B)

(n1 represents an integer of 1 to 3)

(C)

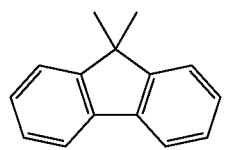

(D)

—CH$_2$—

(E)

—CH—

(F)

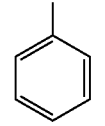

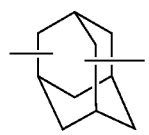

(G)

Furthermore, it is preferred that the di(triarylamine) compound be represented by the following general formula (5);

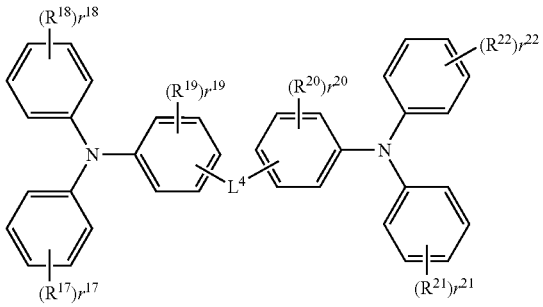

(5)

in this formula, $r^{17}$ to $r^{22}$ each represent an integer indicating the number of substituents $R^{17}$ to $R^{22}$ bonded to aromatic rings; $r^{17}$, $r^{18}$, $r^{21}$, and $r^{22}$ each represent an integer of 0 to 5; $r^{19}$ and $r^{20}$ each represent 0 or an integer of 1 to 4;

$R^{17}$ to $R^{22}$ each represent a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, an aromatic hydrocarbon group, an aromatic heterocyclic group, an aralkyl group, or an aryloxy group; when a plurality of $R^{17}$ to $R^{22}$ is bonded to the same benzene ring, the plurality of present groups may be bonded to each other via a single bond, an oxygen atom, a sulfur atom, or an optionally substituted methylene group to form a ring;

$L^4$ represents a single bond or a divalent organic group represented by the formulas (B) to (G) presented in the explanation of the general formula (4).

Further, in the present invention, it is preferred that the pyrimidine compound be represented by the following general formula (2a) or general formula (2b);

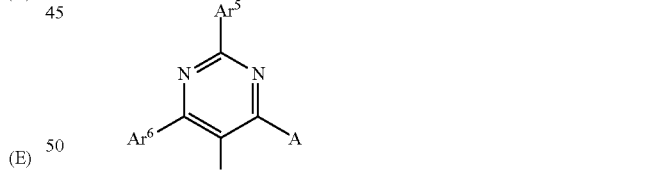

(2a)

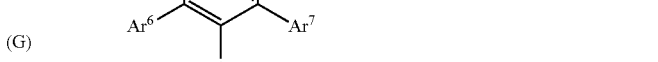

(2b)

in the general formulas (2a) and (2b), $Ar^5$ to $Ar^7$ and A are as defined in the general formula (2).

In the general formula (2) representing the pyrimidine compound, it is preferred that the monovalent organic group A be represented by the following general formula (3a);

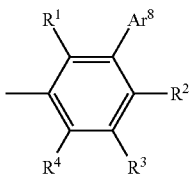

(3a)

in this formula,

Ar$^8$ and R$^1$ to R$^4$ are as defined in the general formula (3).

In the above-described organic EL device of the present invention, it is desirable that:

(1) the luminous layer include a blue luminous dopant;
(2) the blue luminous dopant be a pyrene derivative;
(3) the luminous layer include an anthracene derivative; and
(4) the anthracene derivative be a host material.

Advantageous Effects of Invention

The organic EL device of the present invention has a basic structure having an anode, a first hole transport layer, a second hole transport layer, a luminous layer, an electron transport layer, and a cathode in the order of description, but the arylamine derivative represented by the general formula (1) and included in the second hole transport layer and the pyrimidine compound included in the electron transport layer have the following specific features:

(1) satisfactory hole or electron injection-transport characteristic; and
(2) stability and excellent durability in a thin-film state.

As a result, in the organic EL device of the present invention, holes and electrons can be injected and transported in the luminous layer with satisfactory efficiency, light emission is realized with a high efficiency at a low driving voltage, and the service life of the device is extended.

Further, in the present invention, the first hole transport layer includes an arylamine compound having hole transport property and having a molecular structure different from that of the arylamine derivative included in the second hole transport layer, for example, a poly(triarylamine) compound represented by the general formula (4) or a di(triarylamine) compound represented by the general formula (5). As a result, holes and electrons can be injected and transported in the luminous layer with satisfactory efficiency, a high carrier balance can be ensured, and higher characteristics can be realized.

DESCRIPTION OF EMBODIMENTS

Figure 1:
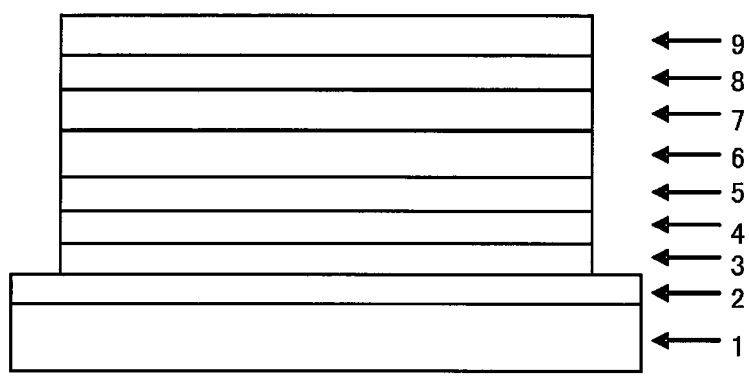
FIG. 1 is a view showing an example of the preferred layer configuration of the organic EL device of the present invention.
Figure 2:
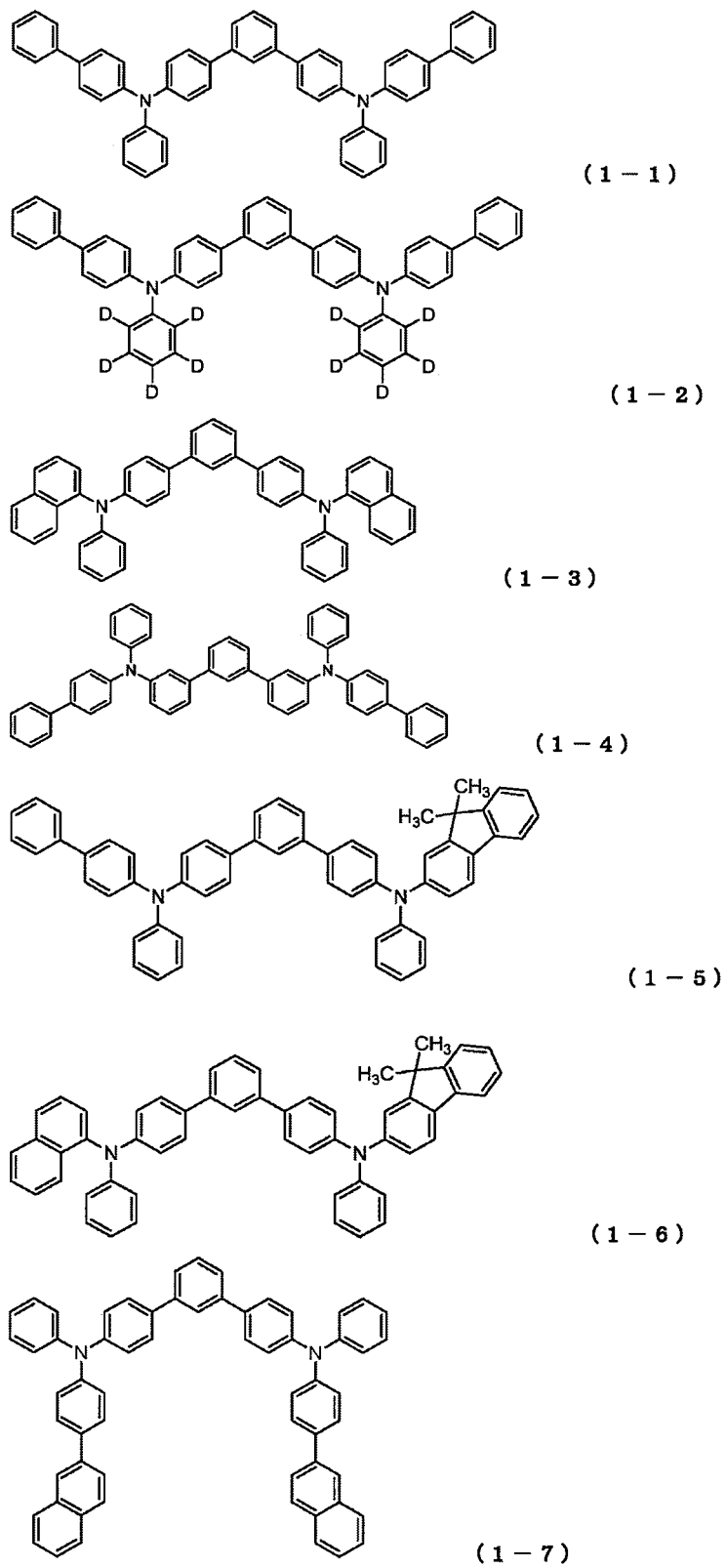
FIG. 2 is a view showing the structural formulas of Compounds No. (1-1) to (1-7) in the arylamine derivative of a general formula (1).
Figure 3:
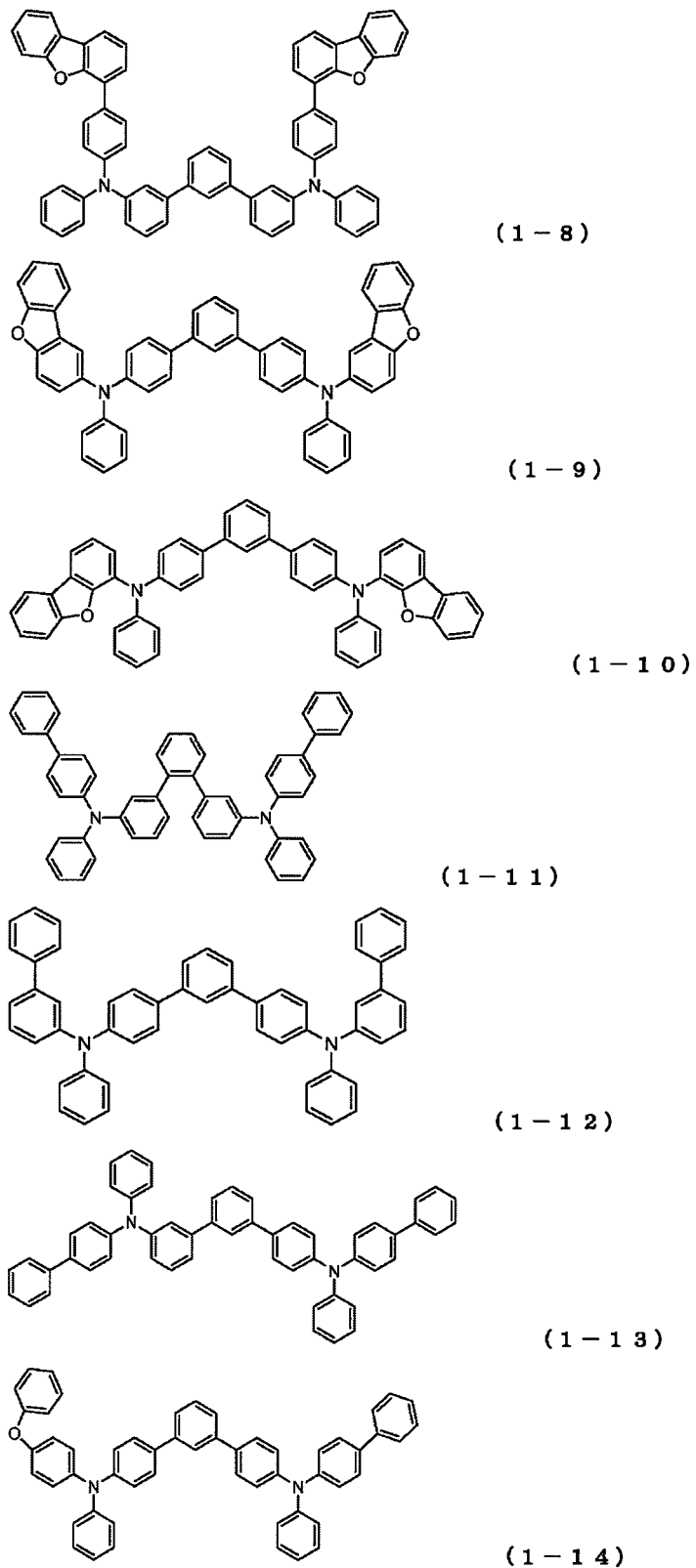
FIG. 3 is a view showing the structural formulas of Compounds No. (1-8) to (1-14) in the arylamine derivative of the general formula (1).
Figure 4:
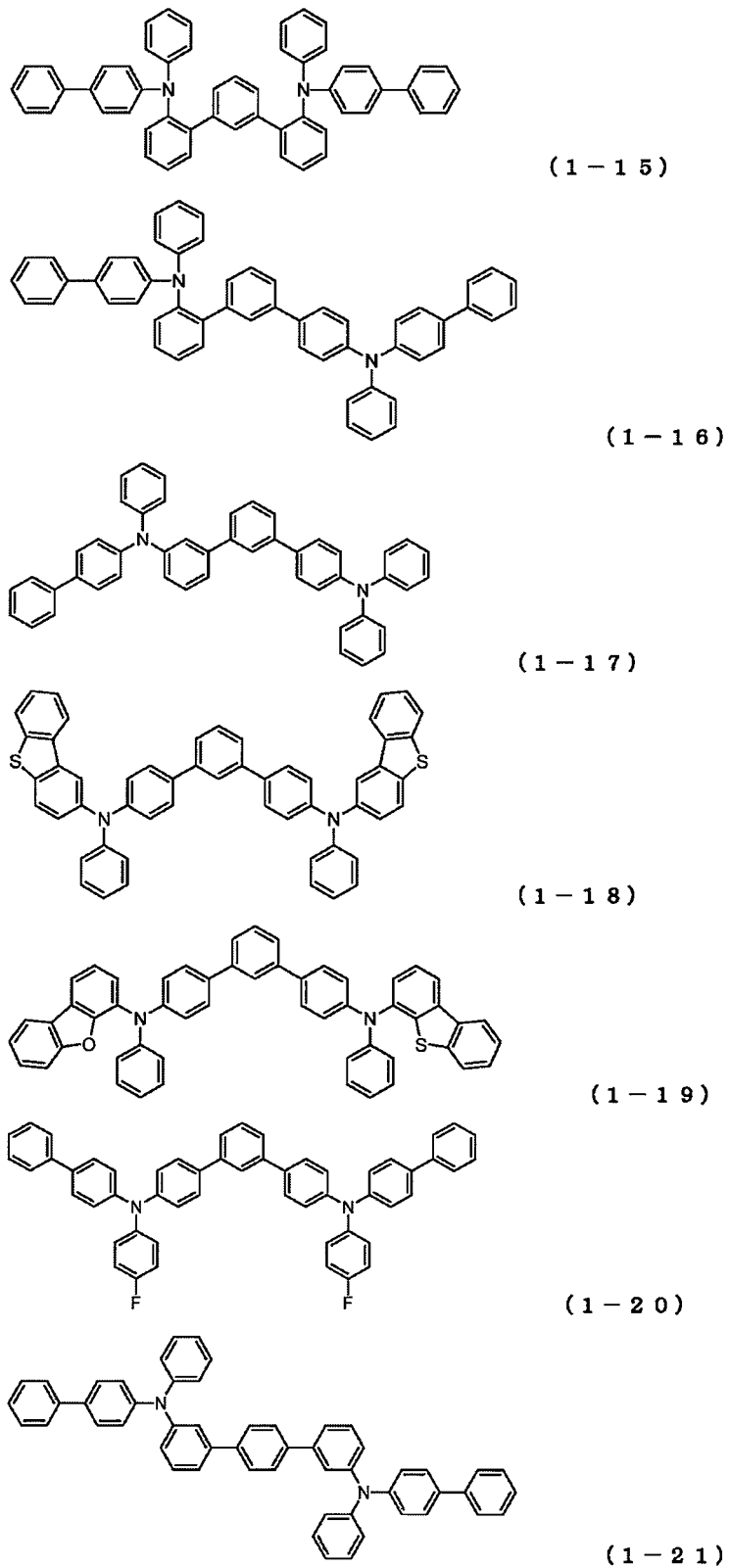
FIG. 4 is a view showing the structural formulas of Compounds No. (1-15) to (1-21) in the arylamine derivative of the general formula (1).
Figure 5:
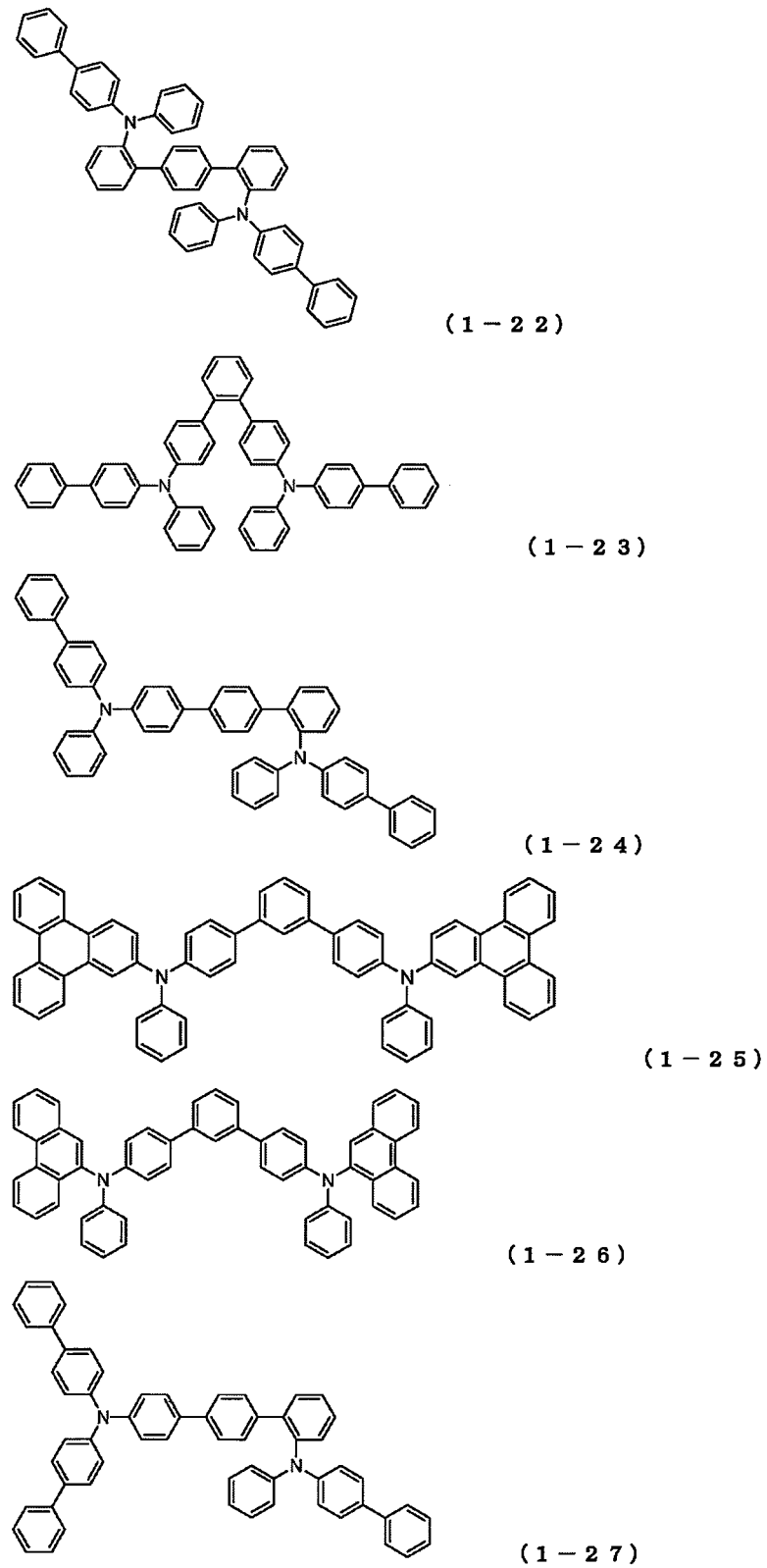
FIG. 5 is a view showing the structural formulas of Compounds No. (1-22) to (1-27) in the arylamine derivative of the general formula (1).
Figure 6:
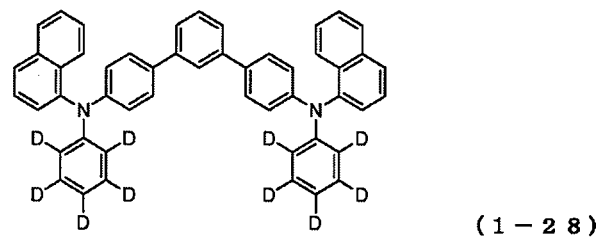
FIG. 6 is a view showing the structural formulas of Compounds No. (1-28) to (1-33) in the arylamine derivative of the general formula (1).
Figure 6:
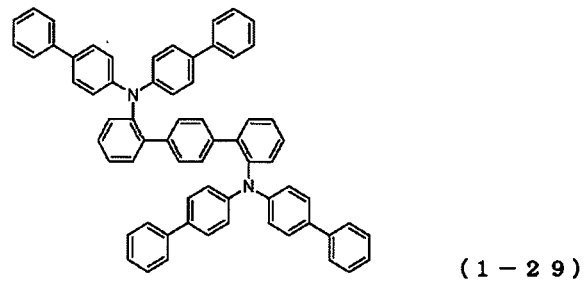
Figure 6:
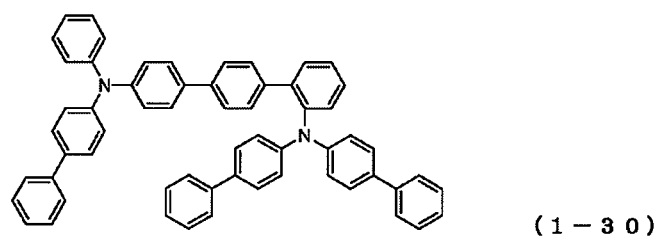
Figure 6:
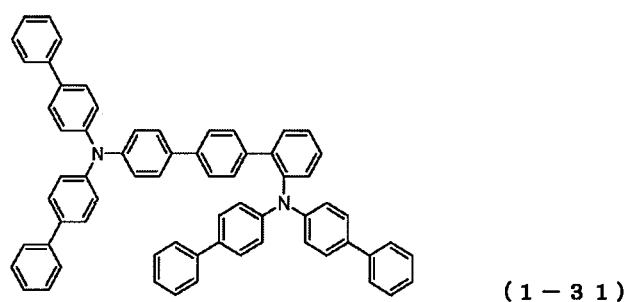
Figure 6:
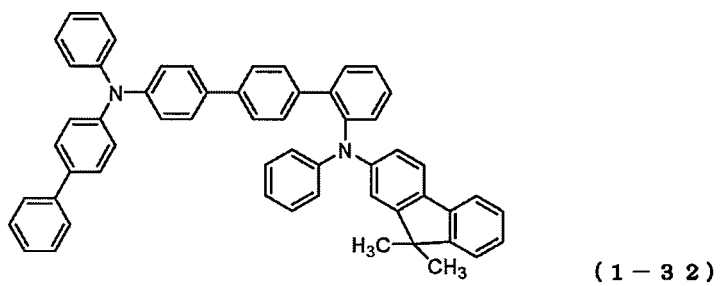
Figure 6:
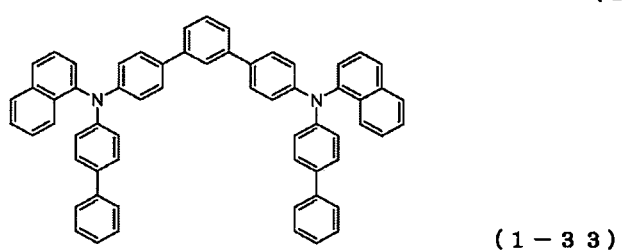
Figure 7:
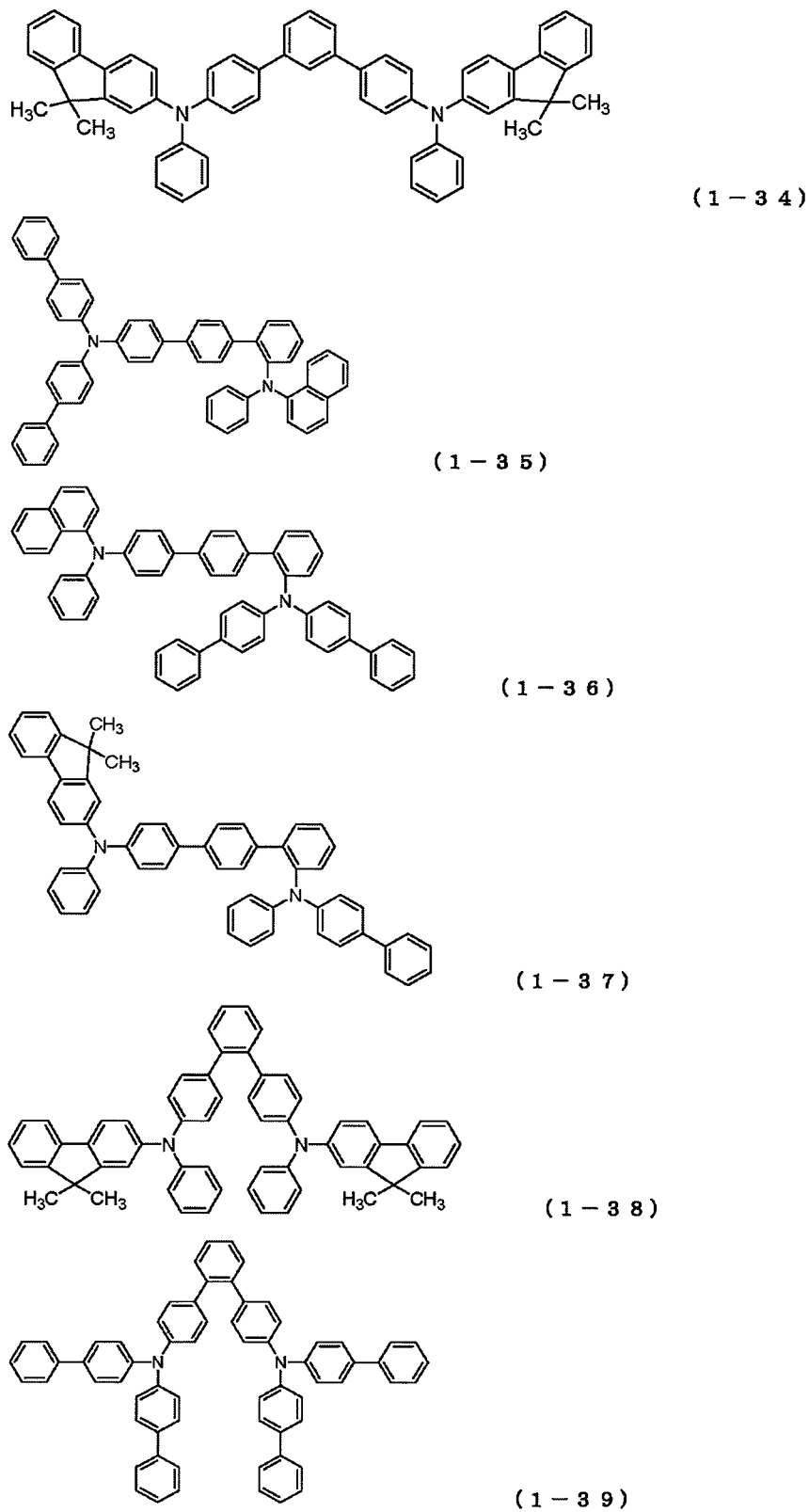
FIG. 7 is a view showing the structural formulas of Compounds No. (1-34) to (1-39) in the arylamine derivative of the general formula (1).
Figure 8:
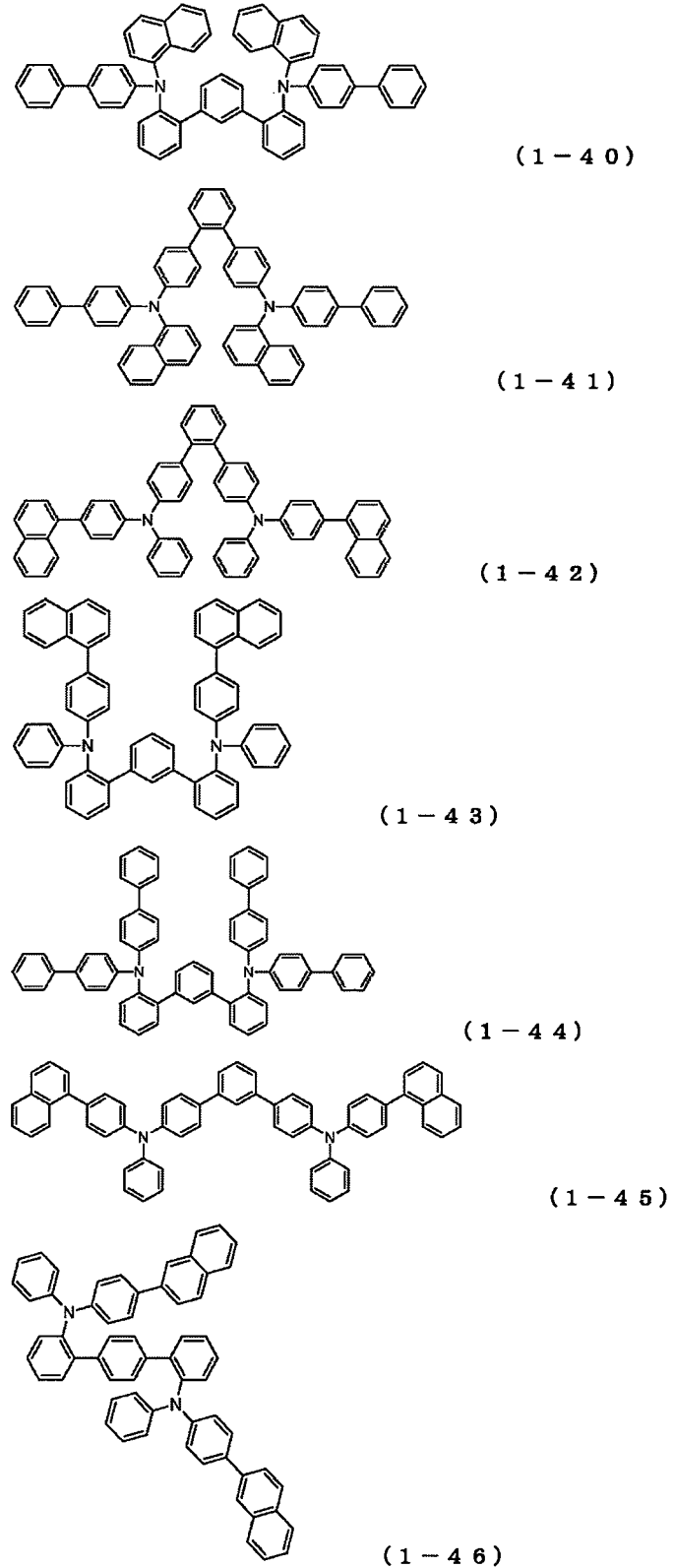
FIG. 8 is a view showing the structural formulas of Compounds No. (1-40) to (1-46) in the arylamine derivative of the general formula (1).
Figure 9:
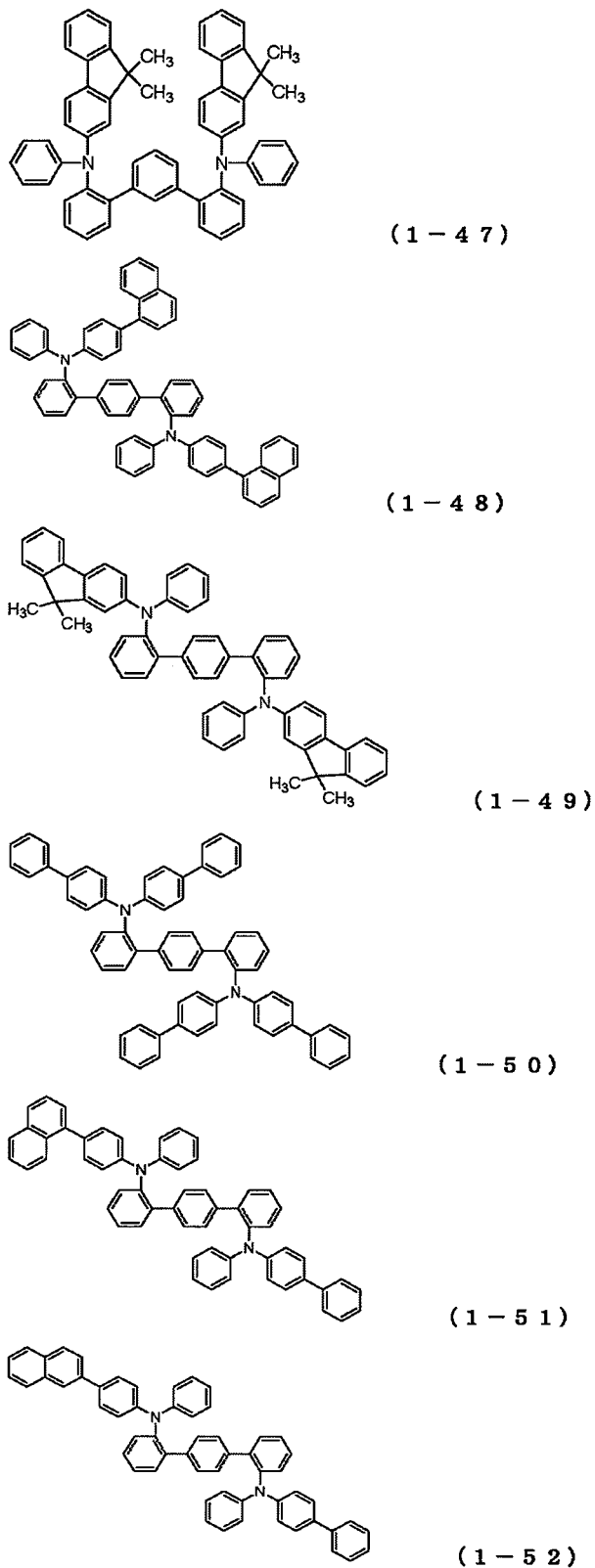
FIG. 9 is a view showing the structural formulas of Compounds No. (1-47) to (1-52) in the arylamine derivative of the general formula (1).
Figure 10:
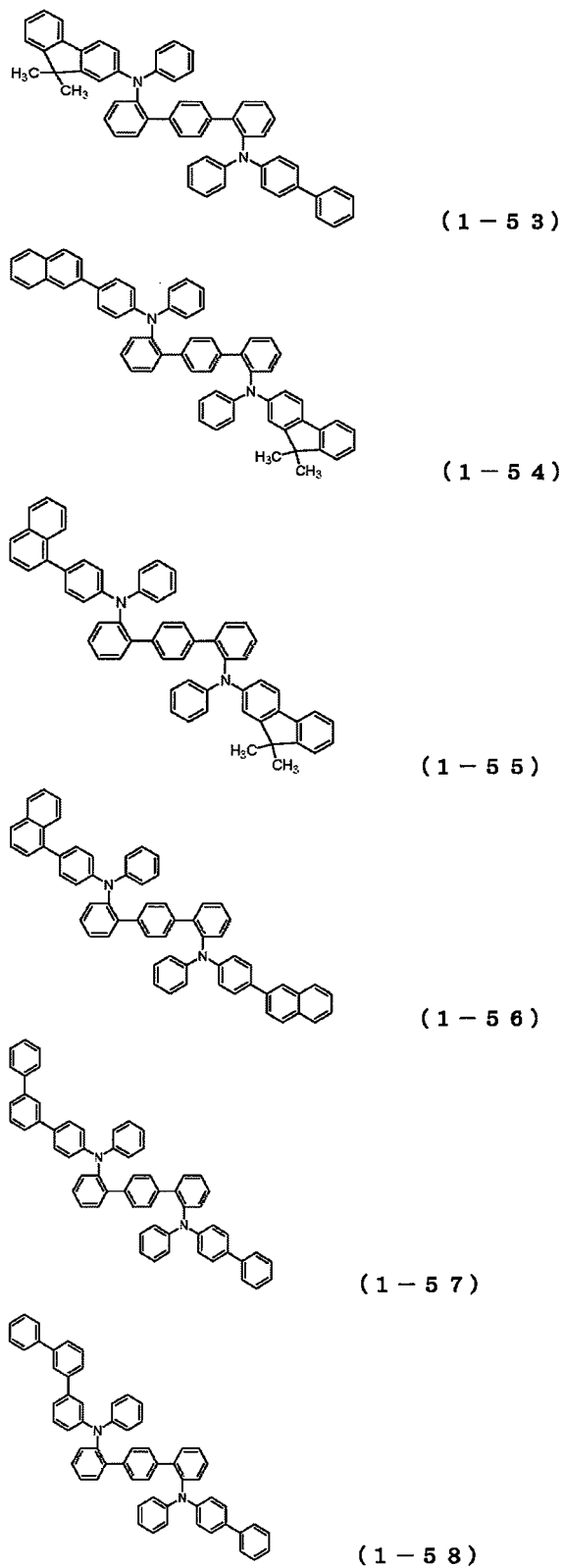
FIG. 10 is a view showing the structural formulas of Compounds No. (1-53) to (1-58) in the arylamine derivative of the general formula (1).
Figure 11:
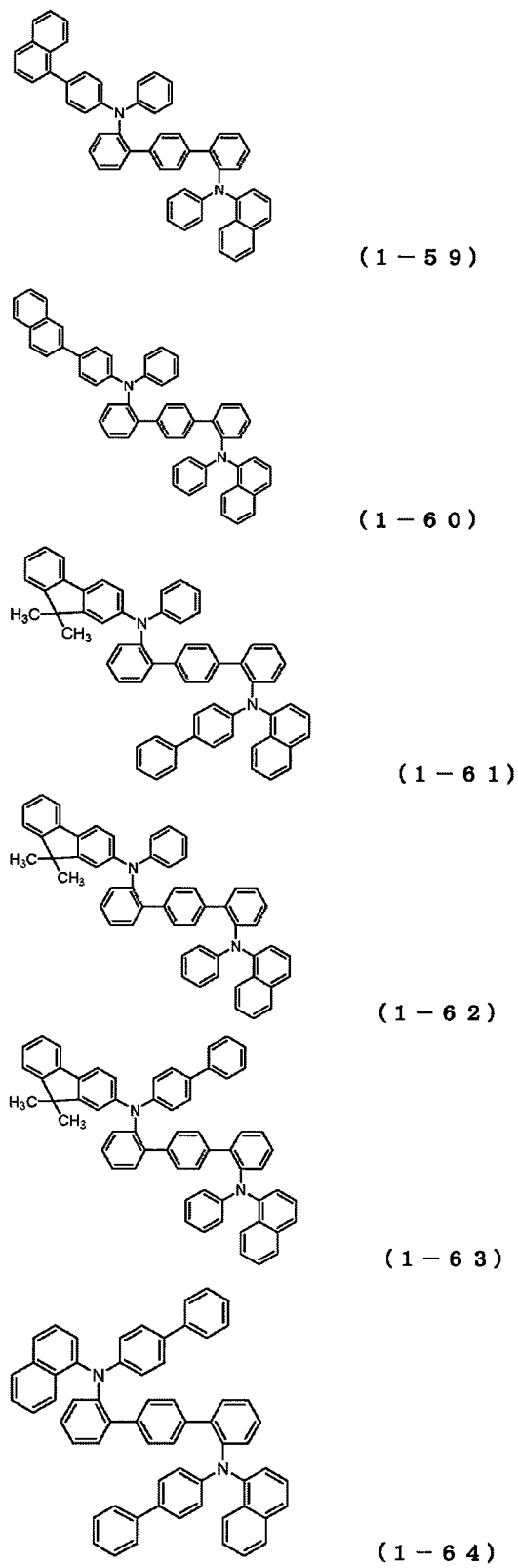
FIG. 11 is a view showing the structural formulas of Compounds No. (1-59) to (1-64) in the arylamine derivative of the general formula (1).
Figure 12:
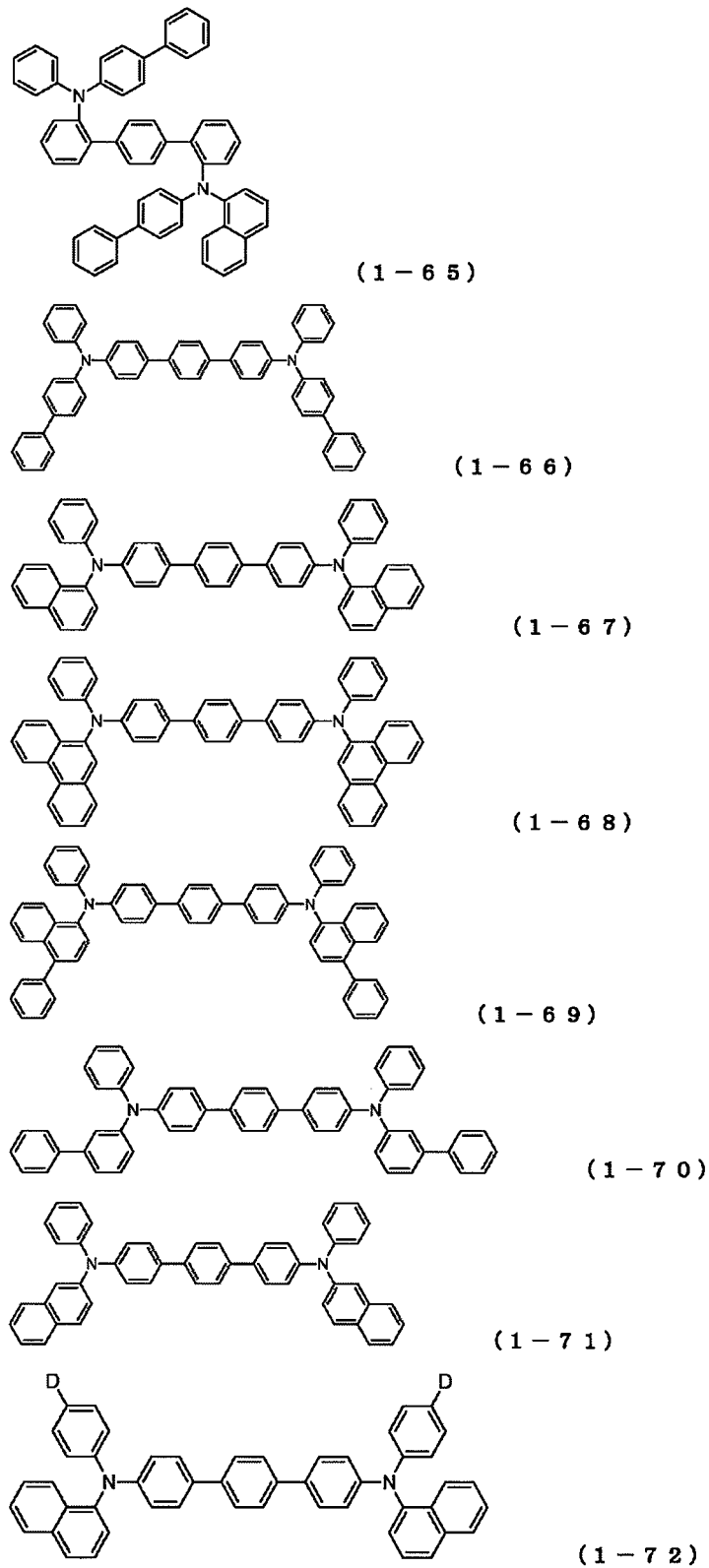
FIG. 12 is a view showing the structural formulas of Compounds No. (1-65) to (1-72) in the arylamine derivative of the general formula (1).
Figure 13:
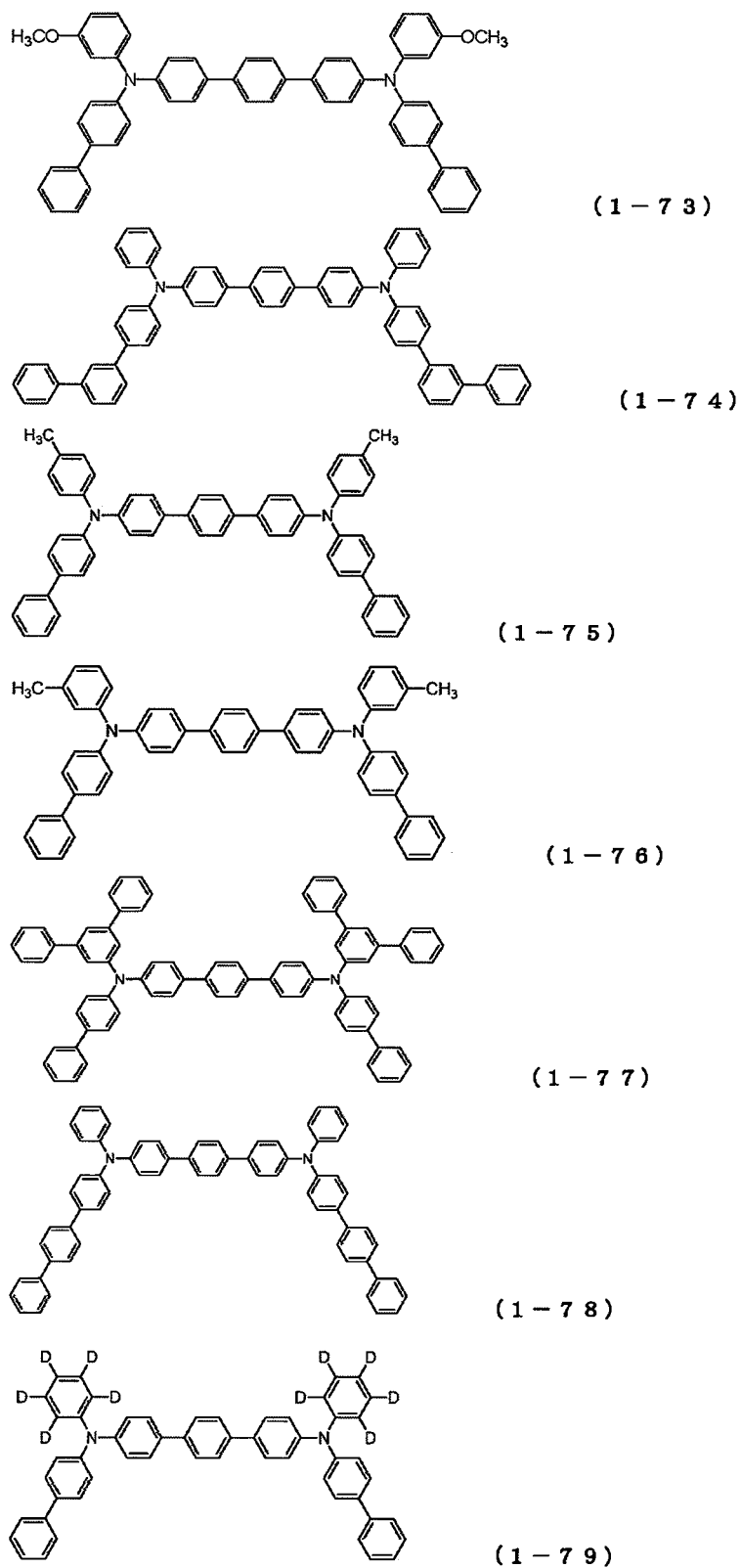
FIG. 13 is a view showing the structural formulas of Compounds No. (1-73) to (1-79) in the arylamine derivative of the general formula (1).
Figure 14:
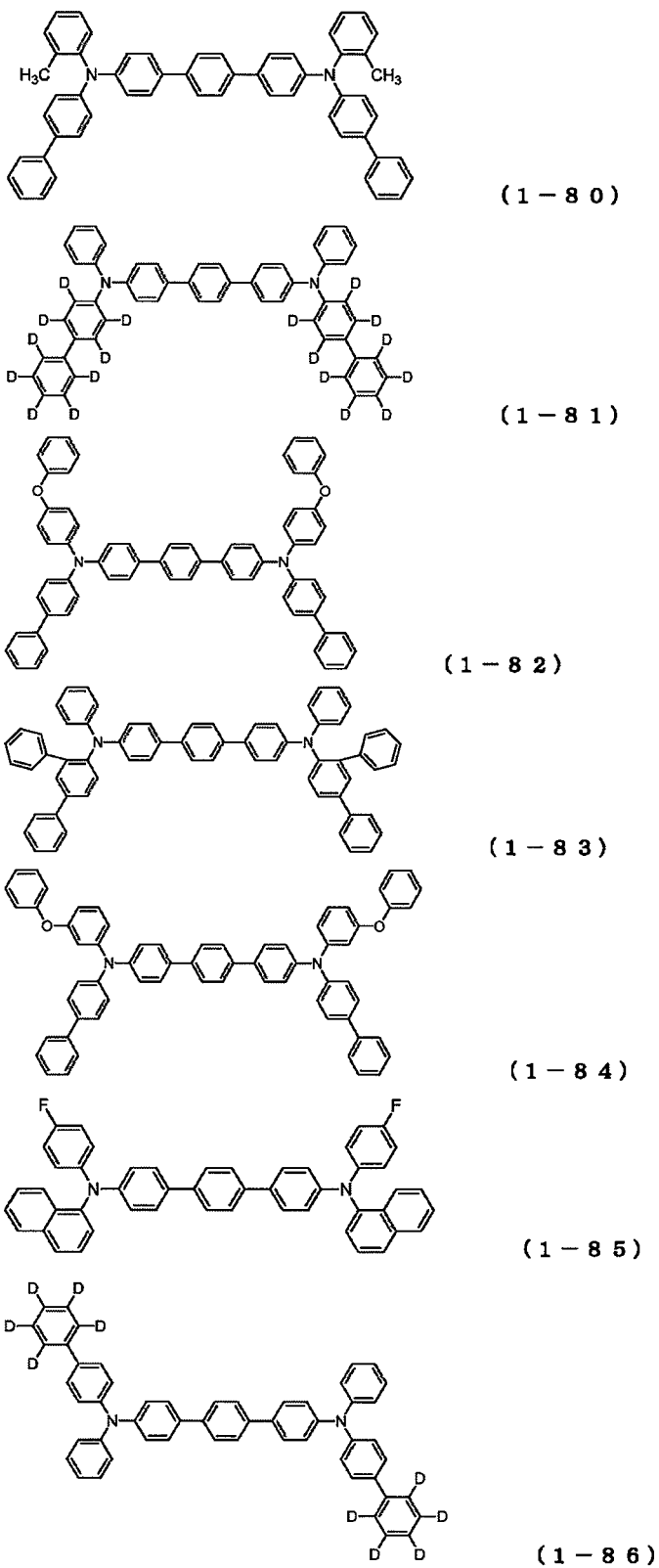
FIG. 14 is a view showing the structural formulas of Compounds No. (1-80) to (1-86) in the arylamine derivative of the general formula (1).
Figure 15:
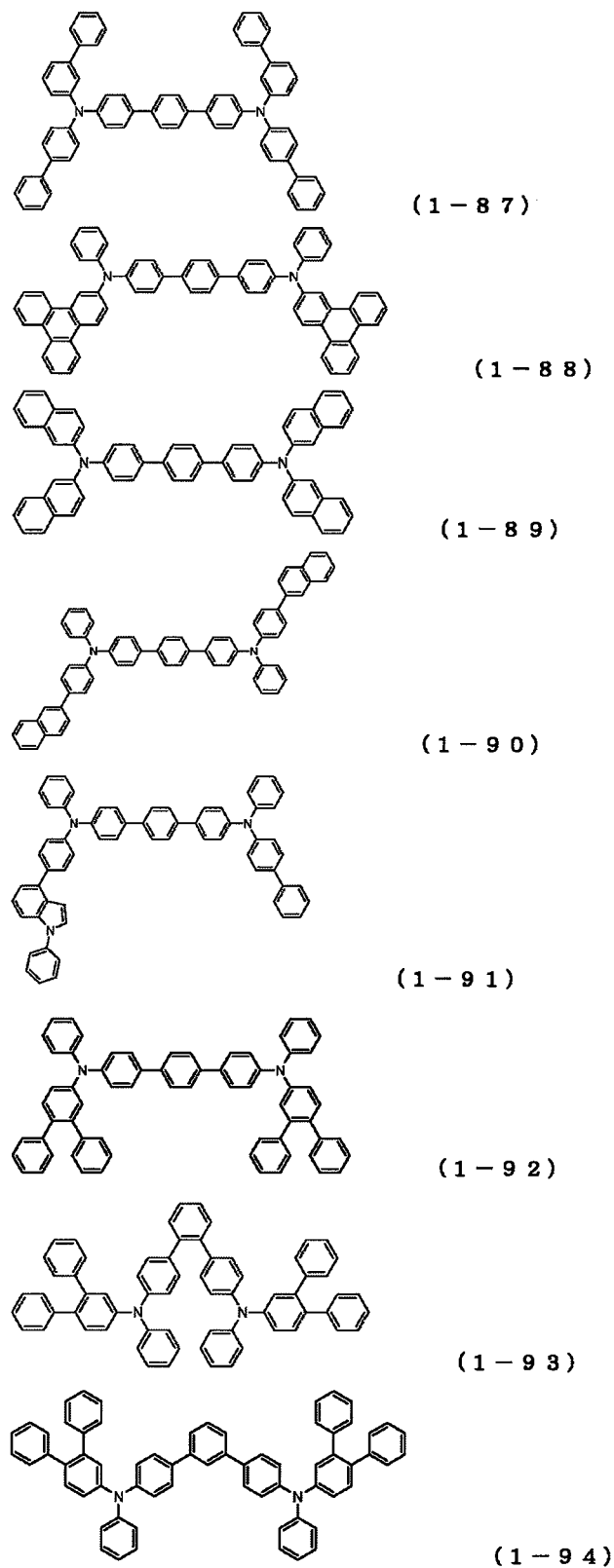
FIG. 15 is a view showing the structural formulas of Compounds No. (1-87) to (1-94) in the arylamine derivative of the general formula (1).
Figure 16:
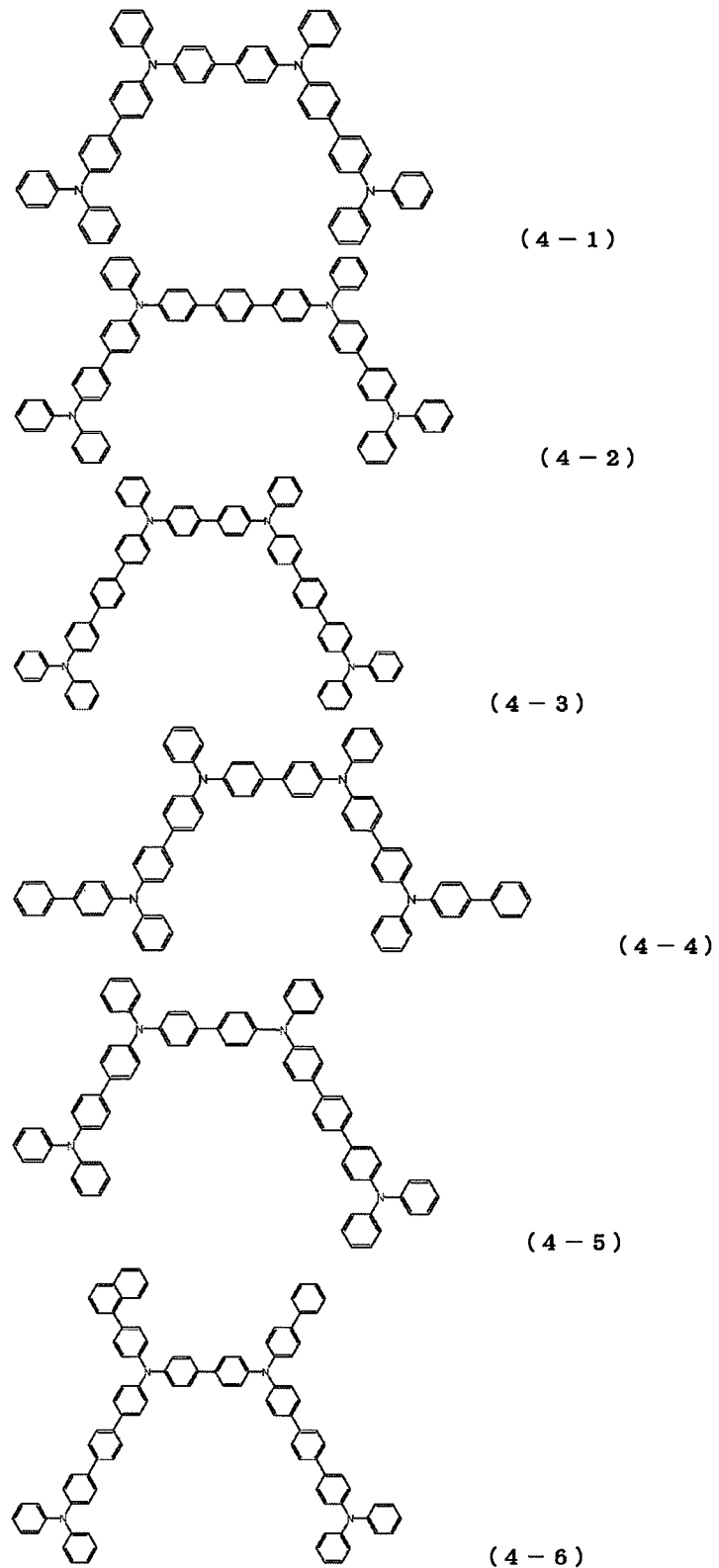
FIG. 16 is a view showing the structural formulas of Compounds No. (4-1) to (4-6) in the poly(triarylamine) compounds of a general formula (4).
Figure 17:
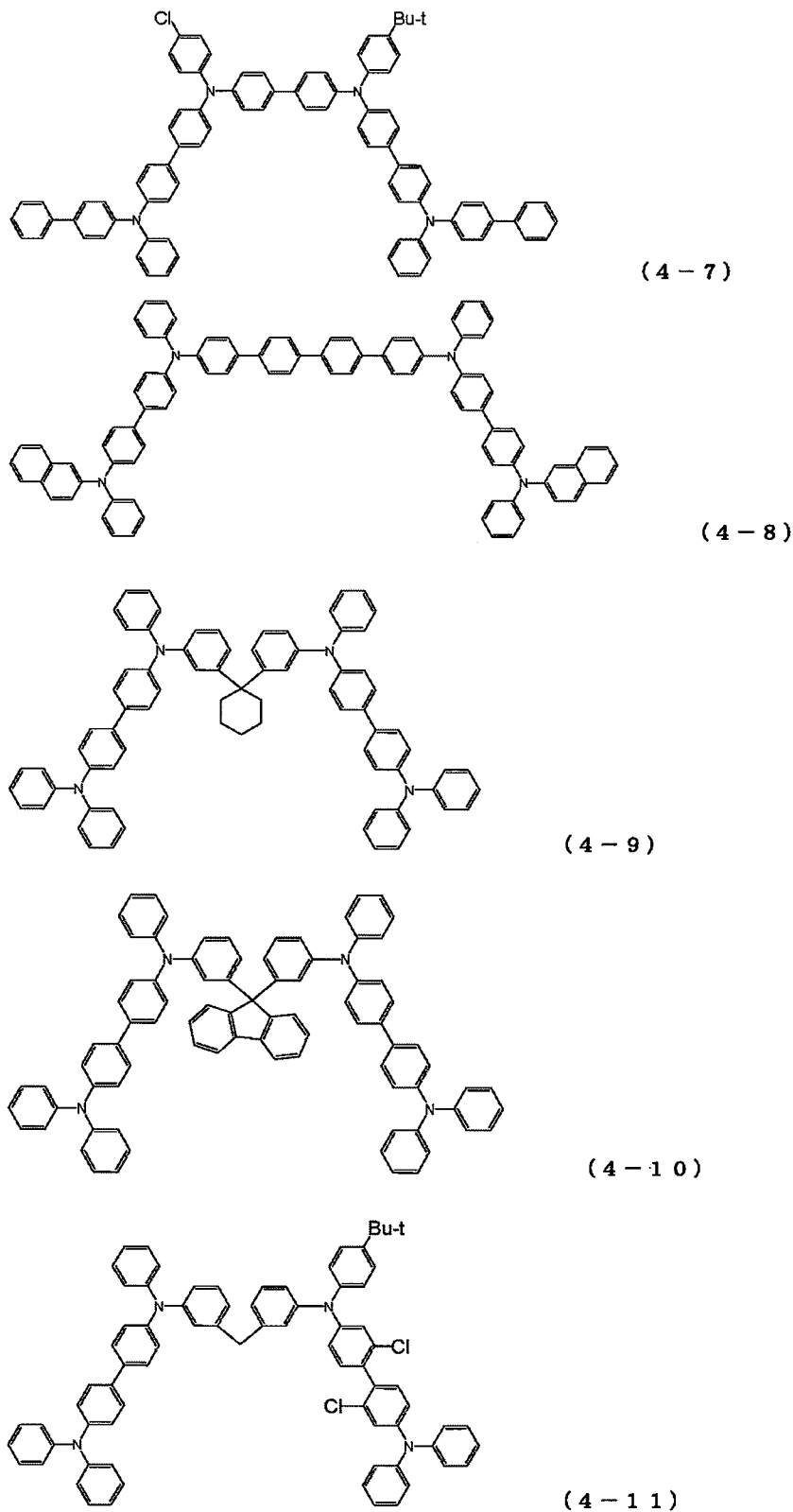
FIG. 17 is a view showing the structural formulas of Compounds No. (4-7) to (4-11) in the poly(triarylamine) compounds of the general formula (4).
Figure 18:
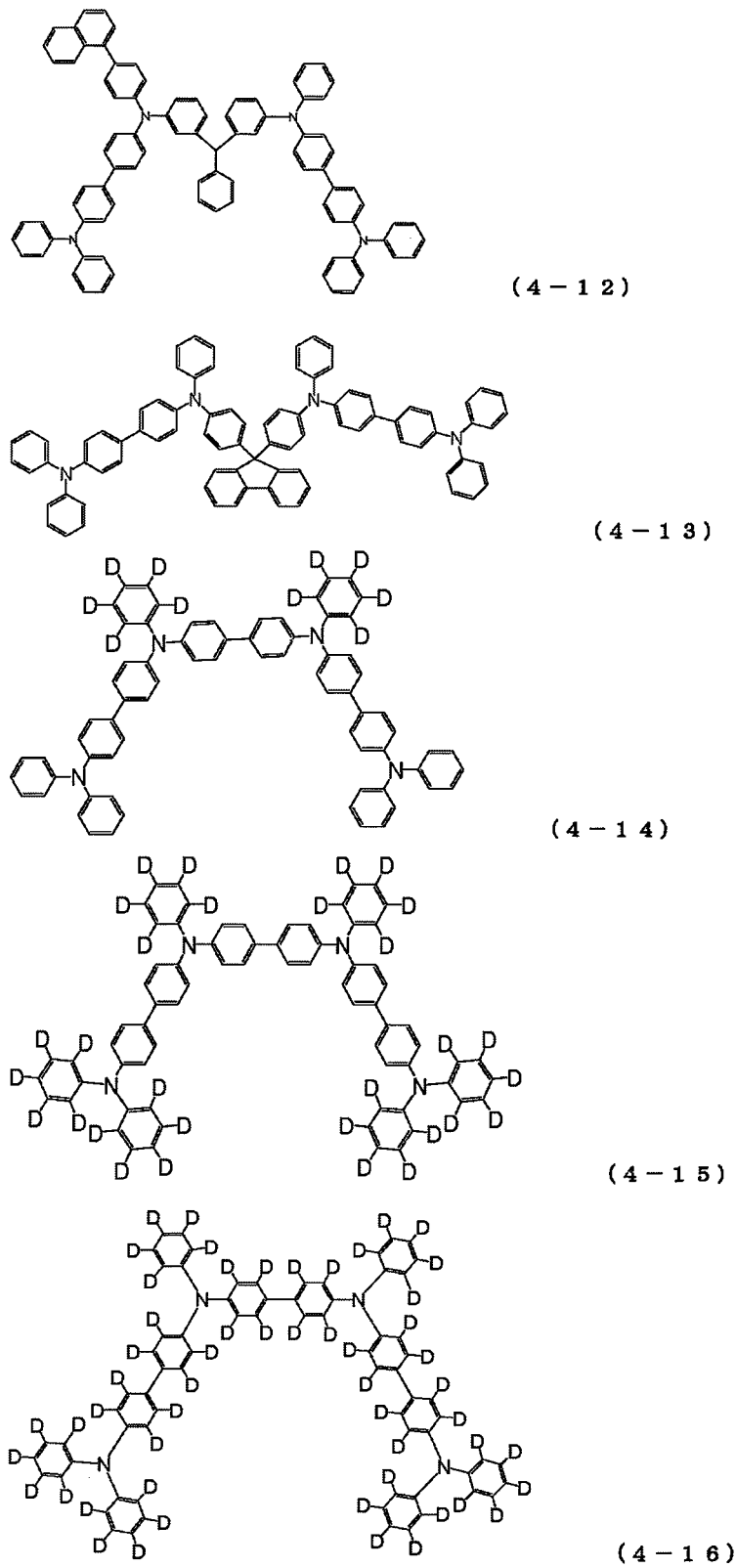
FIG. 18 is a view showing the structural formulas of Compounds No. (4-12) to (4-16) in the poly(triarylamine) compounds of the general formula (4).
Figure 19:
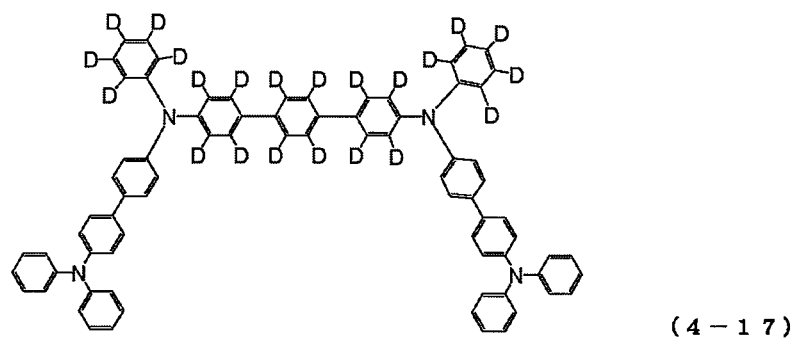
FIG. 19 is a view showing the structural formulas of Compound No. (4-17) in the poly(triarylamine) compounds of the general formula (4).

The organic EL device of the present invention has a basic structure in which an anode, a first hole transport layer, a second hole transport layer, a luminous layer, an electron transport layer, and a cathode are formed, in the order of description, on a transparent substrate such as a glass substrate or a transparent plastic substrate (for example, a polyethylene terephthalate substrate). The layered structure can be in various forms, provided that it has such a basic structure. For example, a hole injection layer can be provided between the anode and the first hole transport layer, and also an electron injection layer can be provided between the electron transport layer and the cathode. For example, FIG. 1 illustrates an example of an advantageous layered structure (used in the below-described Examples) that can be used by the organic EL device of the present invention. In this example, an anode 2, a hole injection layer 3, a first hole transport layer 4, a second hole transport layer 5, a luminous layer 6, an electron transport layer 7, an electron injection layer 8, and a cathode 9 are formed, in the order of description, on a transparent substrate 1.

Each layer constituting the organic EL device of the present invention will be explained hereinbelow with reference to the example shown in FIG. 1.

<Anode 2>

The anode 2 is formed on the transparent substrate 1 by vapor deposition of an electrode material with a large work function, such as ITO or gold.

<Hole Injection Layer 3>

The hole injection layer 3 is optionally provided, as appropriate, between the anode 2 and the first hole transport layer 5. The hole injection layer 3 can be formed using publicly known materials, for example, triphenylamine derivatives of a starburst type and various triphenylamine tetramers; porphyrin compounds represented by copper phthalocyanine; and heterocyclic compounds having acceptor property, such as hexacyanoazatriphenylene, and coating-type polymer materials. Further, a material P-doped with trisbromophenylamine hexachloroantimony, a radialene derivative (see WO 2014/009310), or the like, or a polymer compound having the structure of a benzidine derivative such as TPD in a partial structure thereof can be also used.

<Hole Transport Layer>

The hole transport layer is provided between the anode 2 and the luminous layer 6. In the present invention, as clearly seen in FIG. 1, the hole transport layer has a two-layer structure including the first hole transport layer 4 positioned on the side of the anode 2 and the second hole transport layer 5 positioned on the side of the luminous layer 6.

The Second Hole Transport Layer 5;

In the present invention, the second hole transport layer 5 positioned on the side of the luminous layer 6 includes the arylamine derivative represented by the following general formula (1).

The arylamine derivative;

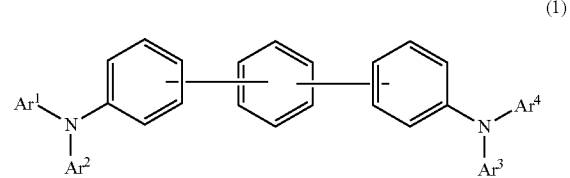

(1)

In the general formula (1), $Ar^1$ to $Ar^4$ each represent an aromatic hydrocarbon group or an aromatic heterocyclic group. These groups may have a substituent.

Further, the $Ar^1$ to $Ar^4$ may be present independently of each other, or $Ar^1$ and $Ar^2$, or $Ar^3$ and $Ar^4$ may be bonded to each other via a single bond, an optionally substituted methylene group, an oxygen atom, or a sulfur atom to form a ring.

The aromatic hydrocarbon group is formed from an aromatic hydrocarbon ring having one bonding hand, and the aromatic heterocyclic group is formed from an aromatic heterocycle having one bonding hand, and any of these may have a condensed polycyclic structure. Examples thereof are presented below.

The Aromatic Hydrocarbon Group;

a phenyl group, a biphenyl group, a terphenyl group, a tetrakisphenyl group, a styryl group, a naphthyl group, an anthracenyl group, a phenanthrenyl group, a fluorenyl group, an indenyl group, a pyrenyl group, a perylenyl group, a fluoranthenyl group, a triphenylenyl group, etc.

The Aromatic Heterocyclic Group;

a pyridyl group, a pyrimidinyl group, a triazinyl group, a furyl group, a pyrrolyl group, a thienyl group, a quinolyl group, an isoquinolyl group, a benzofuranyl group, a benzothienyl group, an indolyl group, a carbazolyl group, a quinazolinyl group, a benzoxazolyl group, a benzothiazolyl group, a quinoxalinyl group, a benzimidazolyl group, a benzoquinazolinyl group, a pyridopyrimidinyl group, a pyrazolyl group, a naphthopyrimidinyl group, a dibenzofuranyl group, a dibenzothienyl group, a naphthylidinyl group, a phenanthrolinyl group, an acridinyl group, a carbolinyl group, etc.

Further, the following groups, in addition to a deuterium atom, a cyano group, a nitro group and the like, can exemplify the substituents that may be possessed by the aromatic hydrocarbon group and the aromatic heterocyclic group.

A halogen atom, for example, a fluorine atom, a chlorine atom, a bromine atom, and an iodine atom;

an alkyl group having 1 to 6 carbon atoms, for example, a methyl group, an ethyl group, an n-propyl group, an isopropyl group, an n-butyl group, an isobutyl group, a tert-butyl group, an n-pentyl group, an isopentyl group, a neopentyl group, an n-hexyl group, etc.;

an alkyloxy group having 1 to 6 carbon atoms, for example, a methyloxy group, an ethyloxy group, a propyloxy group, etc.;

an alkenyl group, for example, a vinyl group, an allyl group, etc.;

an aryl group, for example, a phenyl group, a biphenyl group, a terphenyl group, a tetrakisphenyl group, a styryl group, a naphthyl group, an anthracenyl group, a phenanthrenyl group, a fluorenyl group, an indenyl group, a pyrenyl group, a perylenyl group, a fluoranthenyl group, a triphenylenyl group, a spirobifluorenyl group, etc.;

an aryloxy group, for example, a phenyloxy group, a tolyloxy group, etc.;

an aralkyl group, for example, a benzyl group, a phenethyl group, etc.;

an arylalkyloxy group, for example, a benzyloxy group, a phenethyloxy group, etc.;

an aromatic heterocyclic group, for example, a pyridyl group, a pyrimidinyl group, a triazinyl group, a thienyl group, a furyl group, a pyrrolyl group, a quinolyl group, an isoquinolyl group, a benzofuranyl group, a benzothienyl group, an indolyl group, a carbazolyl group, a quinazolinyl group, a benzoxazolyl group, a benzothiazolyl group, a quinoxalinyl group, a benzimidazolyl group, a benzoquinazolinyl group, a pyrazolyl group a dibenzofuranyl group, a dibenzothienyl group, a carbolinyl group, an azafluorenyl group, a diazafluorenyl group, an azaspirobifluorenyl group, a diazaspirobifluorenyl group, etc.;

an arylvinyl group, for example, a styryl group, a naphthylvinyl group, etc.; and an acyl group, for example, an acetyl group, a benzoyl group, etc.

These substituents may further have the substituents exemplified hereinabove.

Further, the substituents exemplified hereinabove may be bonded to each other via a single bond, a substituted or unsubstituted methylene group, an oxygen atom, or a sulfur atom to form a ring.

In the present invention, as will also be understood from the below-described Examples, the arylamine derivative represented by the above-described general formula (1) has a high glass transition temperature Tg (for example, 110° C. or higher), and therefore is stable in a thin-film state and excellent in heat resistance. Further, this arylamine derivative has a high work function as compared with the work function (about 5.4 eV) of a general hole transport material. Therefore, such an arylamine derivative excels in hole transport property and has high hole mobility and a satisfactory hole injection characteristic. This arylamine derivative also excels in electron blocking property.

In the general formula (1) representing the arylamine derivative, a phenyl group, a biphenyl group, a terphenyl group, a naphthyl group, a phenanthrolyl group, a triphenylenyl group, and a fluorenyl group are preferred as the aromatic hydrocarbon group.

Further, among the aromatic heterocyclic groups, sulfur-containing aromatic heterocyclic groups such as a thienyl group, a benzothienyl group, a benzothiazolyl group, and a dibenzothienyl group; oxygen-containing aromatic heterocyclic groups such as a furyl group, a pyrrolyl group, a benzofuranyl group, a benzoxazolyl group, and a dibenzofuranyl group; and N-substituted carbazolyl group are preferred, and a dibenzofuranyl group is more preferred.

Further, a deuterium atom, an alkyl group, a phenyl group, a biphenyl group, a naphthyl group, a dibenzofuranyl group, and a vinyl group are more preferred as the substituents that may be possessed by the hydrocarbon groups or aromatic heterocyclic groups. It is also preferred that these groups be bonded to each other via a single bond to form a condensed aromatic ring.

From the viewpoint of stability of a thin film and heat resistance which affect the device life, it is desirable that the molecule of such an arylamine derivative represented by the general formula (1) have an asymmetrical structure. For example, it is preferred that $Ar^1$ and $Ar^2$ be different groups or that $Ar^3$ and $Ar^4$ be different groups, and it is more preferred that $Ar^1$ and $Ar^2$ be different groups and $Ar^3$ and $Ar^4$ be different groups.

Further, from the viewpoint of stability of a thin film, it is desirable that the molecule of the arylamine derivative be nonlinear. For example, a molecular structure in which the bonding mode of the phenylene group positioned in the center of the molecule and phenyl groups including aromatic amino groups at both ends becomes a 4,4"-diamino-[1,1':4', 1"]terphenyl skeleton (the structure in which all bonds are 1,4-bonds) is not preferable, and it is preferred that 1,2-bonds or 1,3-bonds be admixed.

Thus, it is preferred that the molecule of the arylamine derivative have a nonlinear structure such as with a 4,4"-diamino-[1,1':3'1"]terphenyl skeleton; a 3,3"-diamino-[1,1':

3',1"]terphenyl skeleton; a 2,2"-diamino-[1,1':3',1"]terphenyl skeleton; a 4,4"-diamino-[1,1':2',1"]terphenyl skeleton; a 3,3"-diamino-[1,1':2',1"]terphenyl skeleton; a 2,2"-diamino-[1,1':2',1"]terphenyl skeleton; a 2,4"-diamino-[1,1':4',1"]terphenyl skeleton; a 2,2"-diamino-[1,1':4',1"]terphenyl skeleton; and a 3,3"-diamino-[1,1':4',1"]terphenyl skeleton.

The arylamine derivative having such a nonlinear structure is represented, for example, by the following general formulas (1a-a), (1a-b), (1b-a), (1c-a), (1c-b), or (1c-c).

In these general formulas, $Ar^1$ to $Ar^4$ are the groups described in reference to the general formula (1).

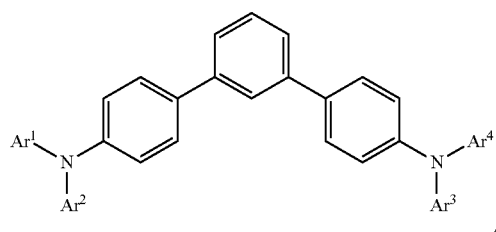
(1a-a)

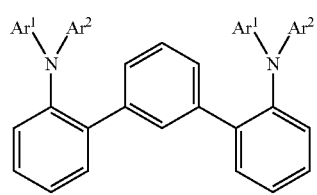
(1a-b)

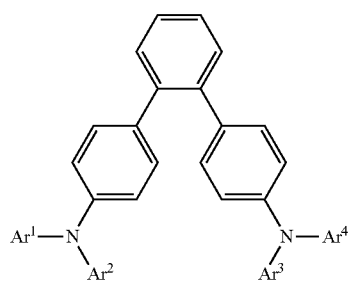
(1b-a)

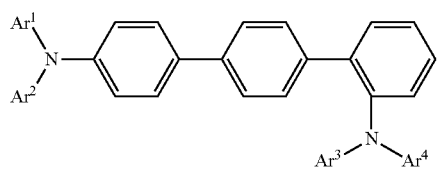
(1c-a)

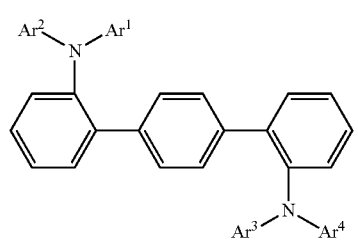
(1c-b)

-continued

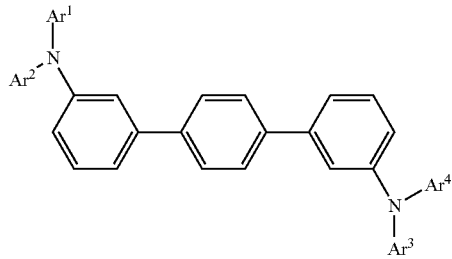
(1c-c)

The arylamine derivatives represented by the above-described general formula (1) can be exemplified by Compounds No. (1-1) to No. (1-94) having the structural formulas shown in FIGS. 2 to 15, but the arylamine derivatives are not limited to these compounds.

Such arylamine derivatives demonstrate high electron blocking property in addition to hole transport property. Therefore, because the second hole transport layer 5 on the side of the luminous layer 6 includes the arylamine derivative, a higher carrier balance in the luminous layer 6 can be maintained and this is very advantageous for improving the characteristics of the organic EL device.

The above-described arylamine derivatives can be used singly or in a mixture of two or more thereof. Furthermore, the second hole transport layer 5 can be also formed by using the arylamine derivatives in combination with publicly known hole transport materials within a range in which the excellent properties of such arylamine derivatives are not impaired.

Specific publicly known hole transport materials include benzidine derivatives, for example, N,N'-diphenyl-N,N'-di (m-tolyl)benzidine (TPD), N,N'-diphenyl-N,N'-di(α-naphthyl)benzidine (NPD), and N,N,N',N'-tetrabiphenylbenzidine; 1,1-bis[4-(di-4-tolylamino)phenyl]cyclohexane (TAPC); triarylamine compounds represented by the below-described general formula (4) or general formula (5); and also various triphenylamine trimers.

Further, for example, a material P-doped with trisbromophenylamine hexachloroantimony, a radialene derivative (see, for example, WO 2014/009310), or the like, or a polymer compound having the molecular structure of a benzidine derivative such as TPD can be used in combination with the above-described materials in the second hole transport layer 5.

The First Hole Transport Layer 4;

In the present invention, the second hole transport layer 5 is formed of the arylamine derivative represented by the general formula (1), but the first hole transport layer 4 located on the side of the anode 2 is formed using a hole transport material which is different from the arylamine derivative used for forming the second hole transport layer 5.

This hole transport material may be the arylamine derivative represented by the general formula (1) as long as it is different from that used for forming the second hole transport layer 5, but in general it is desirable that the first hole transport layer be formed using a triarylamine compound having a triarylamine skeleton. This is because from the viewpoint of the electron blocking property, such a triarylamine compound is inferior to the above-mentioned arylamine derivatives, but from the viewpoint of the hole transport property, the triarylamine compound exhibits performance equal to or higher than that of the arylamine derivatives and, furthermore, the electron blocking property is not so required for the first hole transport layer 4 which is not in direct contact with the luminous layer 6.

From the viewpoint of hole transport property, stability of a thin film and heat resistance and also easiness of synthesis, it is preferred that such a triarylamine derivative be:
(1) a poly(triarylamine) compound having a structure which has 3 to 6 triarylamine skeletons, the triarylamine skeletons being linked to each other via a single bond or a divalent group having no heteroatom; or
(2) a di(triarylamine) compound having a structure which has two triarylamine skeletons in a molecule, the triarylamine skeletons being linked to each other via a single bond or a divalent group having no heteroatom.

Such triarylamine compounds can be used singly or in a mixture of two or more thereof, and also in combination with publicly known hole transport materials which are mentioned in reference to the aforementioned second hole transport layer 5.

The Poly(Triarylamine) Compounds;

The above-mentioned poly(triarylamine) compound is represented, for example, by the general formula (4).

(n1 represents an integer of 1 to 3)

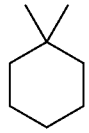  (C)

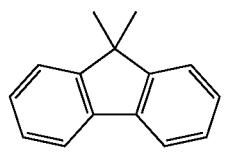  (D)

  (E)
—$CH_2$—

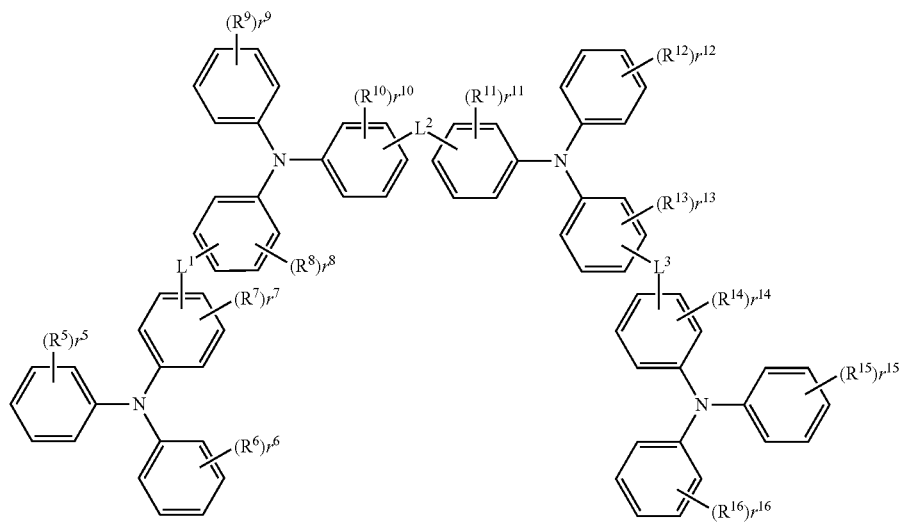

(4)

The poly(triarylamine) compound represented by the general formula (4) has 4 triarylamine structures.

In the general formula (4), $r^5$ to $r^{16}$ each represent an integer indicating the number of substituents $R^5$ to $R^{16}$ bonded to aromatic rings. $r^5$, $r^6$, $r^9$, $r^{12}$, $r^{15}$, and $r^{16}$ each represent an integer of 0 to 5. Further, $r^7$, $r^8$, $r^{10}$, $r^{11}$, $r^{13}$, and $r^{14}$ each represent an integer of 0 to 4.

These $r^5$ to $r^{16}$ are preferably integers of 0 to 3, and more preferably integers of 0 to 2.

Further, $L^1$, $L^2$, and $L^3$ are bridging groups that bond the triarylamine skeletons, and each represents a single bond or a divalent organic group represented by the following formulas (B) to (G).

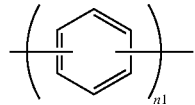  (B)

-continued

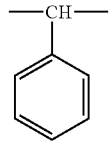  (F)

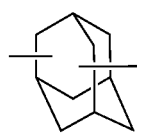  (G)

A single bond and a divalent organic group represented by the formula (B) or (D) is preferred, and a single bond and a divalent organic group represented by the formula (B) is more preferred as the $L^1$, $L^2$, and $L^3$. Further, n1 in the formula (B) is preferably 1 or 2, and more preferably 1.

Further, in the general formula (4), substituents $R^5$ to $R^{16}$ bonded to aromatic rings each represent a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, an aromatic hydrocarbon group, an aromatic heterocyclic group, an aralkyl group, or an aryloxy group.

When a plurality of such substituents $R^5$ to $R^{16}$ is bonded to the same benzene ring, the plurality of present groups may be bonded to each other via a single bond, an oxygen atom, a sulfur atom, or an optionally substituted methylene group to form a ring.

The alkyl group having 1 to 6 carbon atoms can be exemplified by a methyl group, an ethyl group, an n-propyl group, an isopropyl group, an n-butyl group, an isobutyl group, a tert-butyl group, an n-pentyl group, an isopentyl group, a neopentyl group, and an n-hexyl group.

The cycloalkyl group having 5 to 10 carbon atoms can be exemplified by a cyclopentyl group, a cyclohexyl group, a 1-adamantyl group, and a 2-adamantyl group.

The alkenyl group having 2 to 6 carbon atoms can be exemplified by a vinyl group, an allyl group, an isopropenyl group, and a 2-butenyl group.

The alkyloxy group having 1 to 6 carbon atoms can be exemplified by a methyloxy group, an ethyloxy group, an n-propyloxy group, an isopropyloxy group, an n-butyloxy group, a tert-butyloxy group, an n-pentyloxy group, and an n-hexyloxy group.

The cycloalkyloxy group having 5 to 10 carbon atoms can be exemplified by a cyclopentyloxy group, a cyclohexyloxy group, a cycloheptyloxy group, a cyclooctyloxy group, a 1-adamantyloxy group, and a 2-adamantyloxy group.

The aromatic hydrocarbon group and aromatic heterocyclic group can be exemplified by the same ones as those illustrated in relation to groups $Ar^1$ to $Ar^4$ in the general formula (1).

The aralkyl group can be exemplified by a benzyl group and a phenethyl group.

The aryloxy group can be exemplified by a phenyloxy group, a biphenylyloxy group, a terphenylyloxy group, a naphthyloxy group, an anthracenyloxy group, a phenanthrenyloxy group, a fluorenyloxy group, an indenyloxy group, a pyrenyloxy group, and a perylenyloxy group.

Groups represented by the above-described $R^5$ to $R^{16}$ may have a substituent. The substituents can be exemplified by the same ones as those illustrated as the substituents possessed by the aromatic hydrocarbon group and the aromatic heterocyclic group represented by groups $Ar^1$ to $Ar^4$ in the general formula (1), within ranges in which the conditions reflating to the number of carbon atoms are satisfied.

Further, these substituents may be present independently of each other, or these substituents may be bonded to each other via a single bond, an optionally substituted methylene group, an oxygen atom, or a sulfur atom to form a ring.

The preferred groups represented by the above-described $R^5$ to $R^{16}$ are a deuterium atom, an alkyl group, an alkenyl group, and an aromatic hydrocarbon group, and the particularly preferred groups are a deuterium atom, a phenyl group, a biphenyl group, a naphthyl group, and a vinyl group. It is also preferred that these groups be bonded to each other via a single bond to form a condensed aromatic ring.

The poly(triarylamine) compound represented by the above-described general formula (4) can be specifically exemplified by Compounds (4-1) to (4-17) having structural formulas shown in FIGS. 16 to 19.

Figure 20:
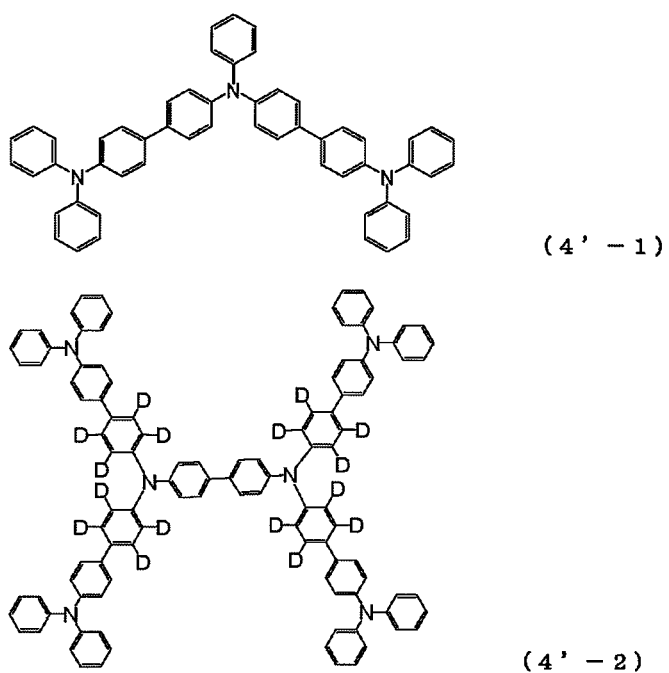
FIG. 20 is a view showing the structural formulas of Compounds No. (4'-1) and (4'-2) in the poly(triarylamine) compounds.
Figure 21:
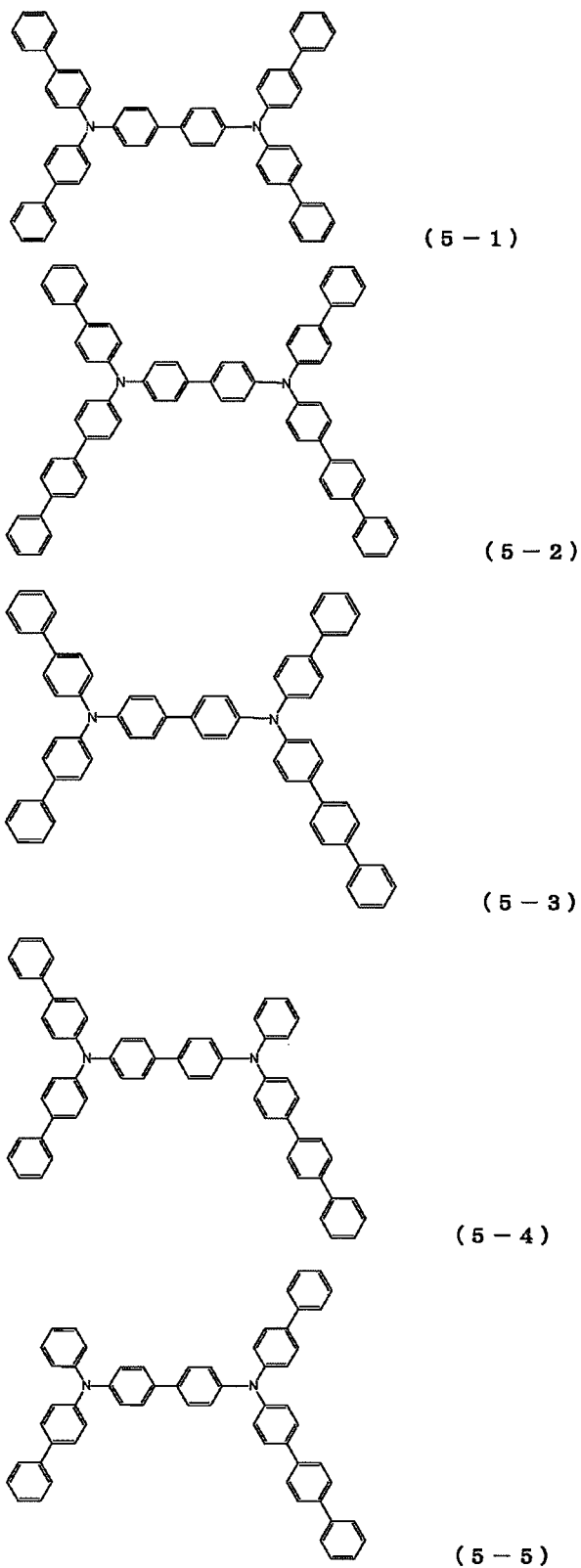
FIG. 21 is a view showing the structural formulas of Compounds No. (5-1) to (5-5) in the di(triarylamine) compounds of a general formula (5).
Figure 22:
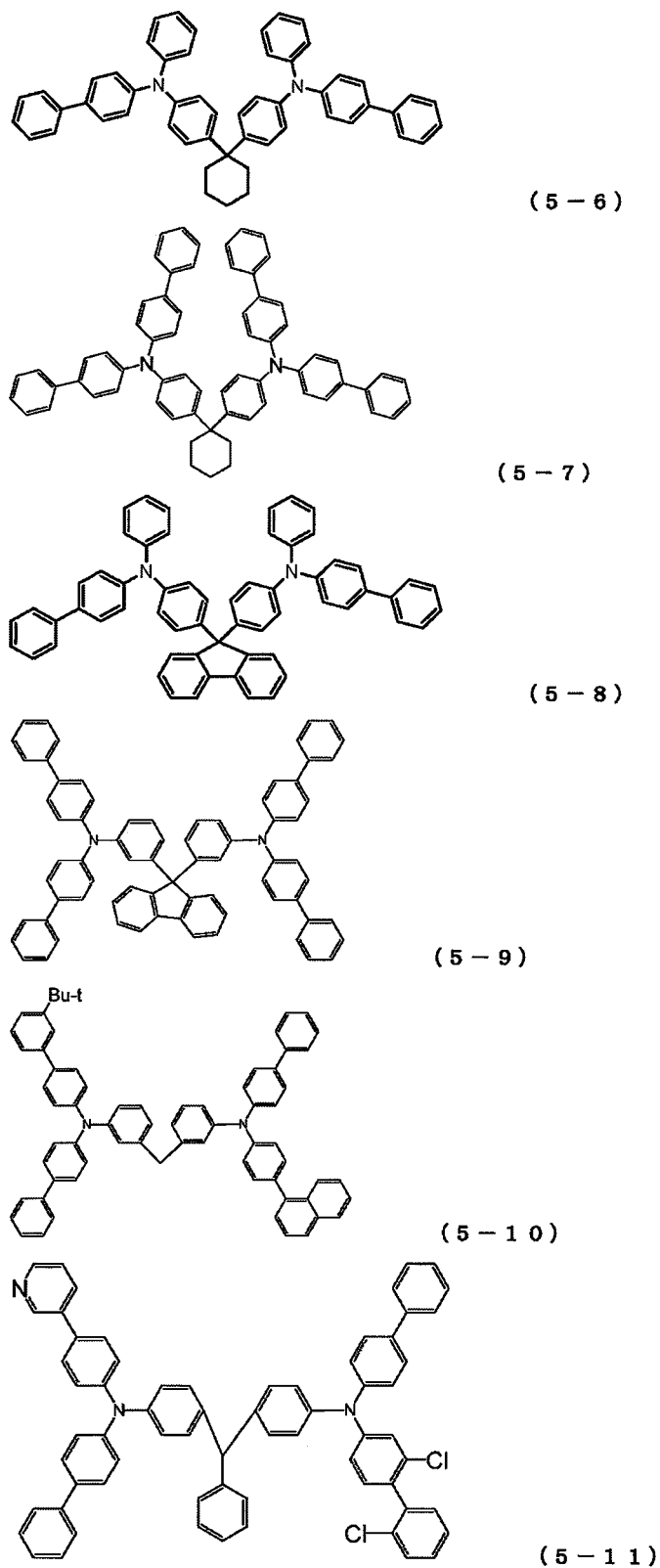
FIG. 22 is a view showing the structural formulas of Compounds No. (5-6) to (5-11) in the di(triarylamine) compounds of the general formula (5).
Figure 23:
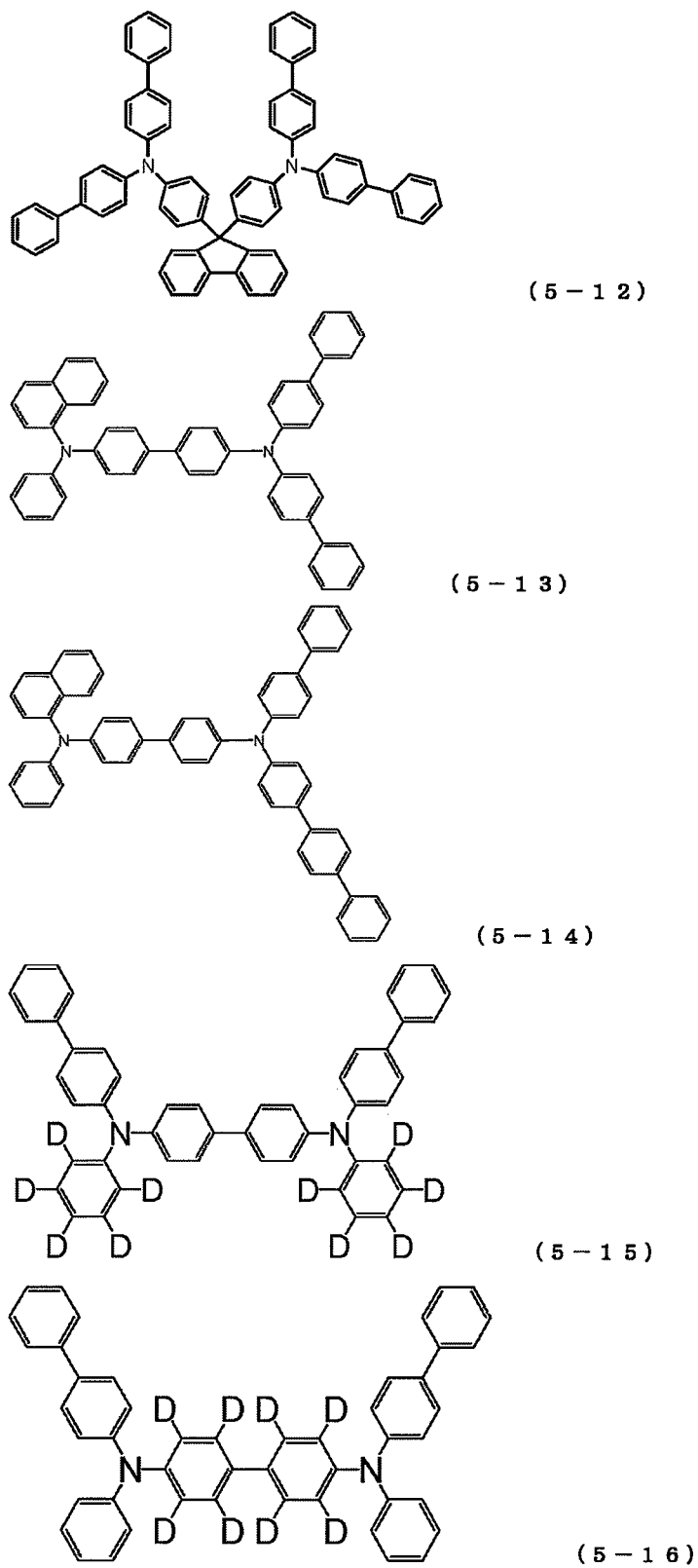
FIG. 23 is a view showing the structural formulas of Compounds No. (5-12) to (5-16) in the di(triarylamine) compounds of the general formula (5).
Figure 24:
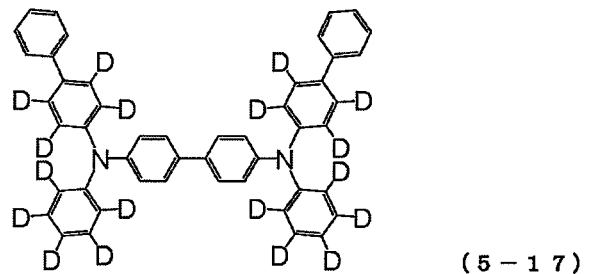
FIG. 24 is a view showing the structural formulas of Compounds No. (5-17) to (5-21) in the di(triarylamine) compounds of the general formula (5).
Figure 24:
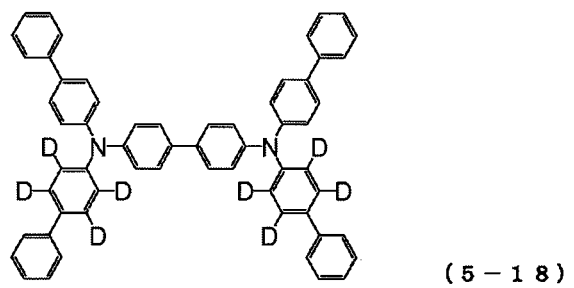
Figure 24:
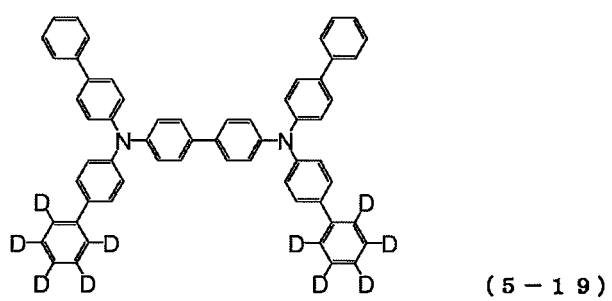
Figure 24:
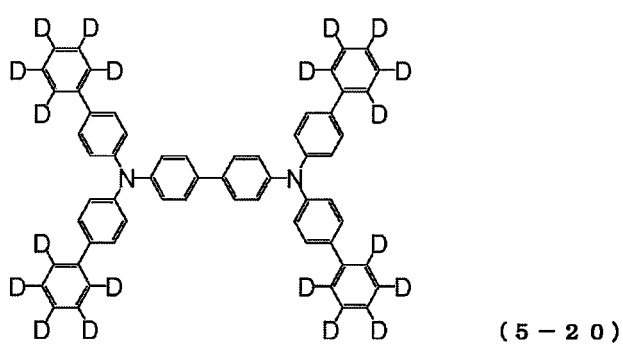
Figure 24:
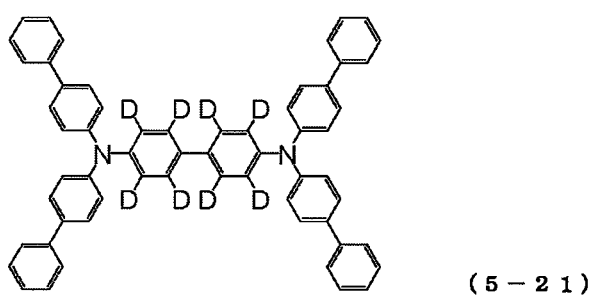
Figure 25:
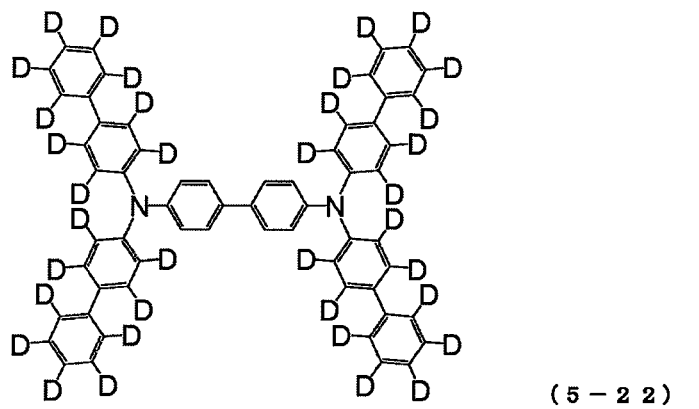
FIG. 25 is a view showing the structural formulas of Compounds No. (5-22) and (5-23) in the di(triarylamine) compounds of the general formula (5).
Figure 25:
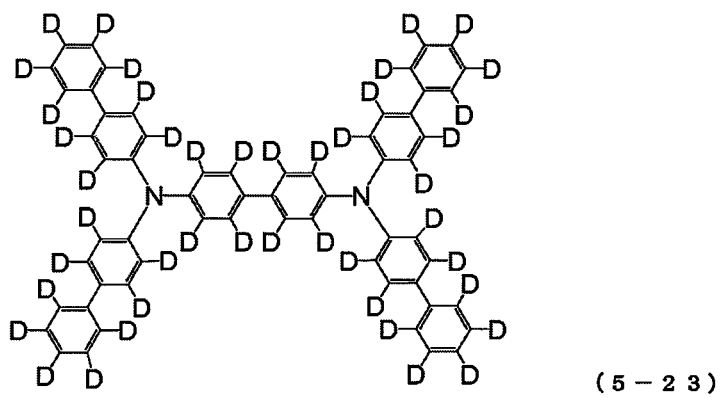

Further, Compounds (4'-1) and (4'-2) which have the structural formulas shown in FIG. 20 and have three or six triarylamine skeletons are not the poly(triarylamine) compounds represented by the general formula (4), but can be advantageously used for forming the first hole transport layer 4.

The Di(Triarylamine) Compounds;

The di(triarylamine) compounds have two triarylamine skeletons in a molecule and are represented, for example, by the general formula (5).

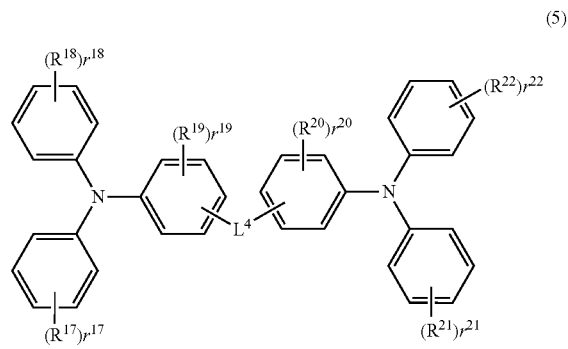

(5)

In the general formula (5), $r^{17}$ to $r^{22}$ each are an integer representing the number of substituents $R^{17}$ to $R^{22}$ bonded to aromatic rings. $r^{17}$, $r^{18}$, $r^{21}$, and $r^{22}$ each represent an integer of 0 to 5. $r^{19}$ and $r^{20}$ each represent an integer of 0 to 4.

These $r^{17}$ to $r^{22}$ are preferably integers of 0 to 3, and more preferably integers of 0 to 2.

Further, $L^4$ is a bridging group that bonds the triarylamine skeletons and represents a single bond or a divalent organic group represented by the formulas (B) to (G) presented in the explanation of the general formula (4).

The $L^4$ is preferably a single bond or a divalent organic group represented by the formula (B), (D), or (G), and more preferably a single bond or a divalent organic group represented by the formula (D), or (G). Further, n1 in the formula (B) is preferably 1 or 2.

Further, in the general formula (5), $R^{17}$ to $R^{22}$ each represent a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, an aromatic hydrocarbon group, an aromatic heterocyclic group, an aralkyl group, or an aryloxy group. When a plurality of $R^{17}$ to $R^{22}$ is bonded to the same benzene ring, the plurality of present groups may be bonded to each other via a single bond, an oxygen atom, a sulfur atom, or an optionally substituted methylene group to form a ring.

The alkyl group, cycloalkyl group, alkenyl group, alkyloxy group, cycloalkyloxy group, aromatic hydrocarbon group, aromatic heterocyclic group, aralkyl group, or aryloxy group can be specifically exemplified by the same ones as those illustrated in relation to the aforementioned groups $R^5$ to $R^{16}$.

Similarly to the groups represented by $R^5$ to $R^{16}$, the groups represented by the above-described $R^{17}$ to $R^{22}$ may have a substituent. The substituents can be exemplified by the same ones as those illustrated in relation to the aforementioned groups $R^5$ to $R^{16}$. These substituents may be present independently of each other, or these substituents may be bonded to each other via a single bond, an optionally substituted methylene group, an oxygen atom, or a sulfur atom to form a ring.

The preferred groups represented by the above-described $R^{17}$ to $R^{22}$ are a deuterium atom, an alkyl group, an alkenyl group, and an aromatic hydrocarbon group, and the particularly preferred groups are a deuterium atom, a phenyl group, and a biphenyl group. It is also preferred that these groups be bonded to each other via a single bond to form a condensed aromatic ring.

The di(triarylamine) compound represented by the above-described general formula (5) can be specifically exemplified by Compounds (5-1) to (5-23) having structural formulas shown in FIGS. 21 to 25.

Figure 26:
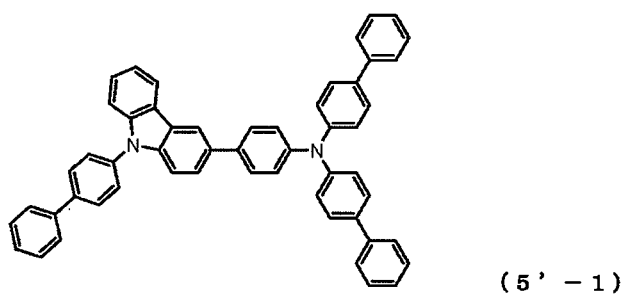
FIG. 26 is a view showing the structural formulas of Compounds No. (5'-1) and (5'-2) in the di(triarylamine) compounds.
Figure 26:
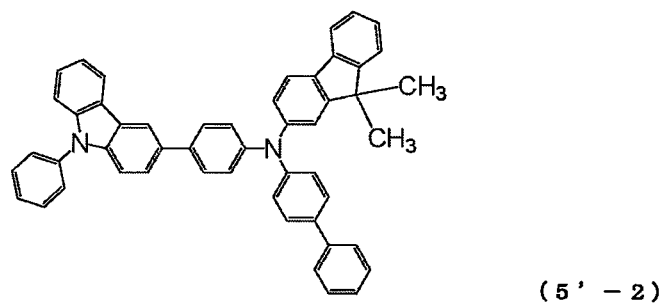
Figure 27:
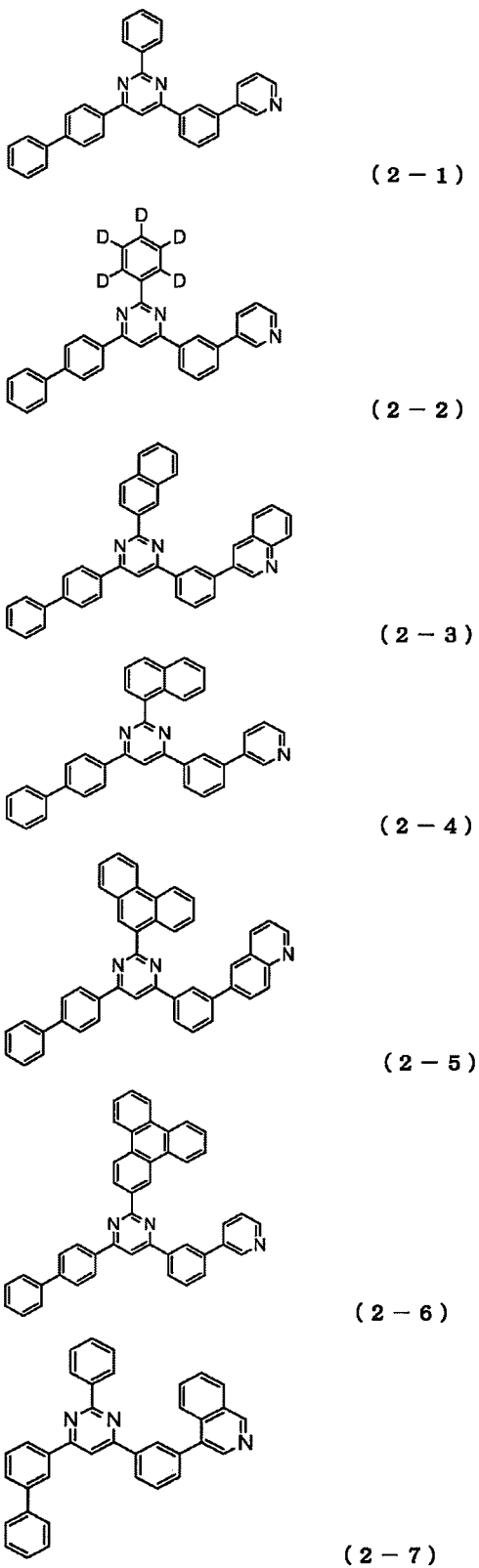
FIG. 27 is a view showing the structural formulas of Compounds No. (2-1) to (2-7) in the pyrimidine compound of a general formula (2).
Figure 28:
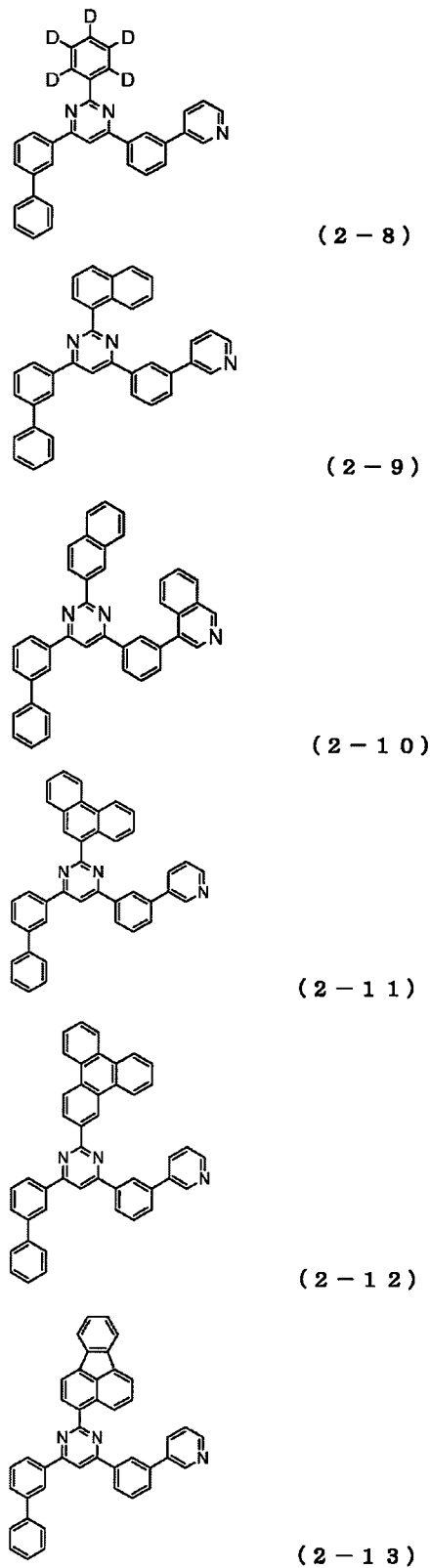
FIG. 28 is a view showing the structural formulas of Compounds No. (2-8) to (2-13) in the pyrimidine compound of the general formula (2).
Figure 29:
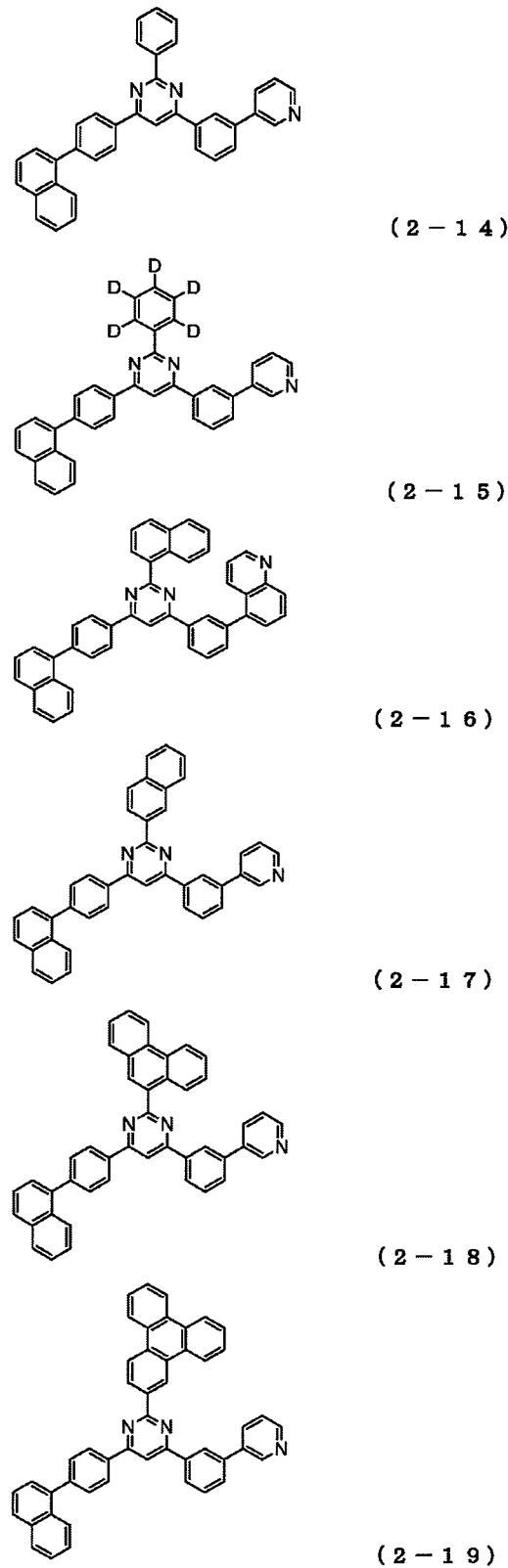
FIG. 29 is a view showing the structural formulas of Compounds No. (2-14) to (2-19) in the pyrimidine compound of the general formula (2).
Figure 30:
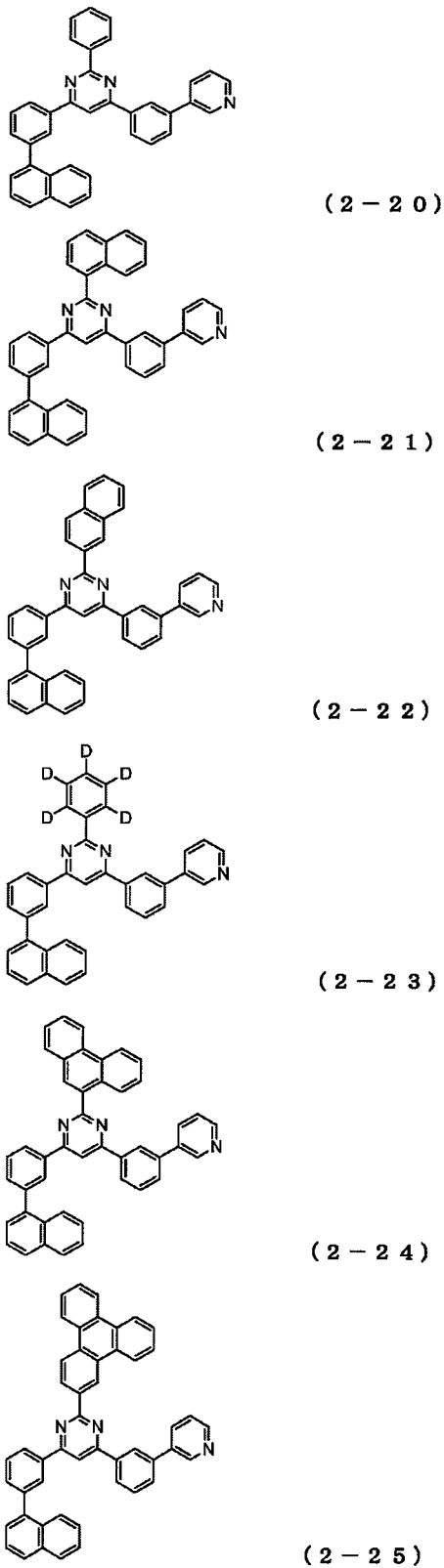
FIG. 30 is a view showing the structural formulas of Compounds No. (2-20) to (2-25) in the pyrimidine compound of the general formula (2).
Figure 31:
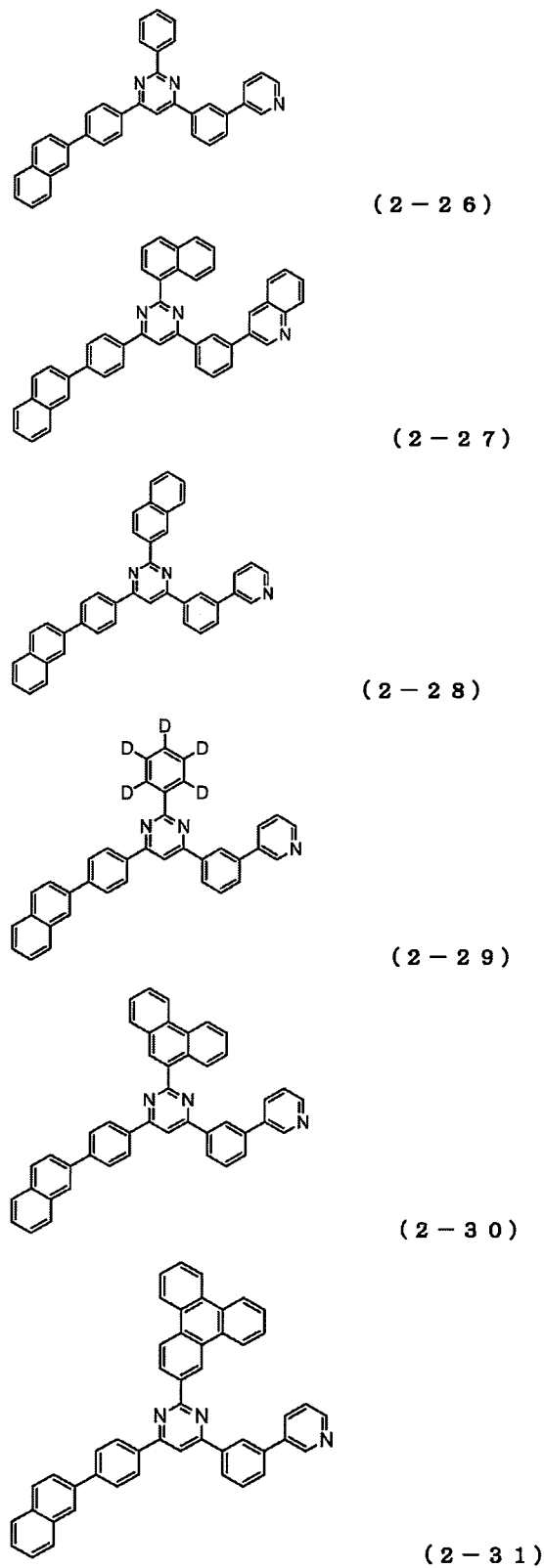
FIG. 31 is a view showing the structural formulas of Compounds No. (2-26) to (2-31) in the pyrimidine compound of the general formula (2).
Figure 32:
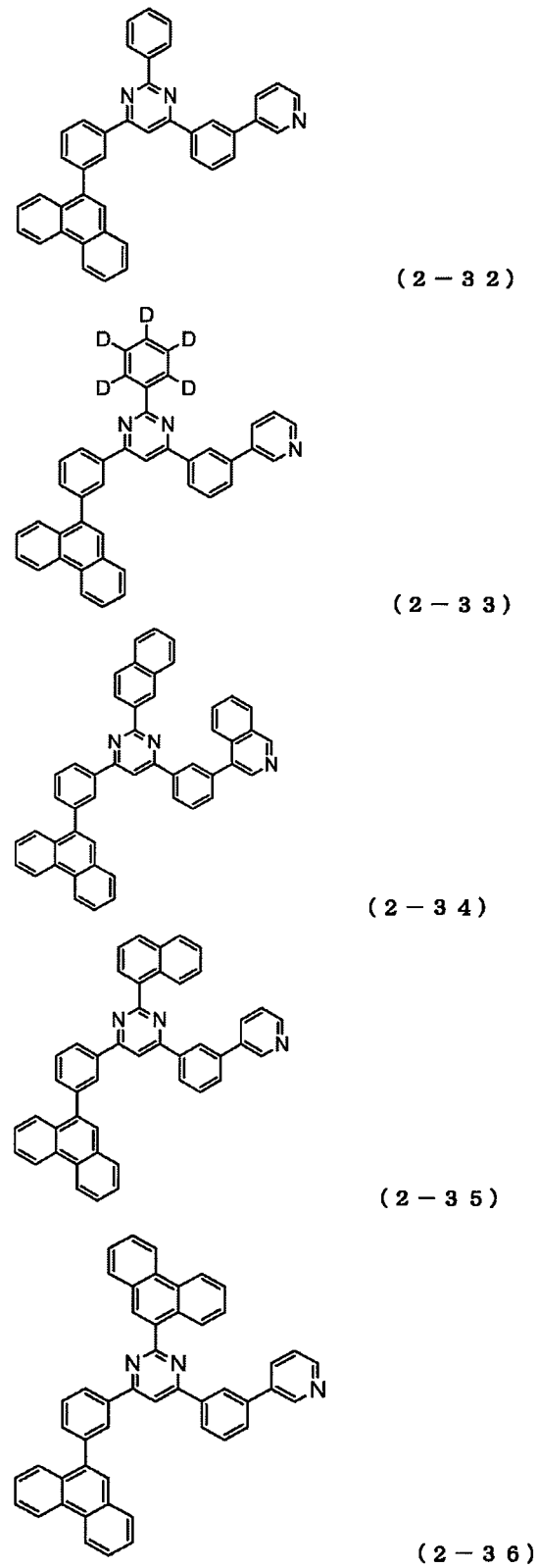
FIG. 32 is a view showing the structural formulas of Compounds No. (2-32) to (2-36) in the pyrimidine compound of the general formula (2).
Figure 33:
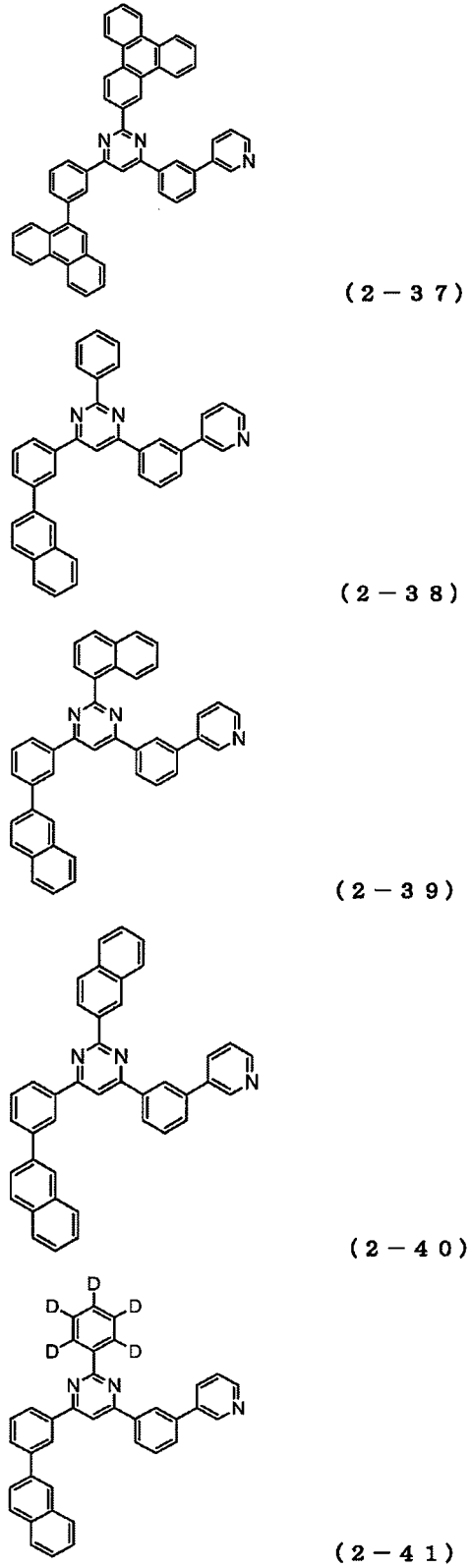
FIG. 33 is a view showing the structural formulas of Compounds No. (2-37) to (2-41) in the pyrimidine compound of the general formula (2).
Figure 34:
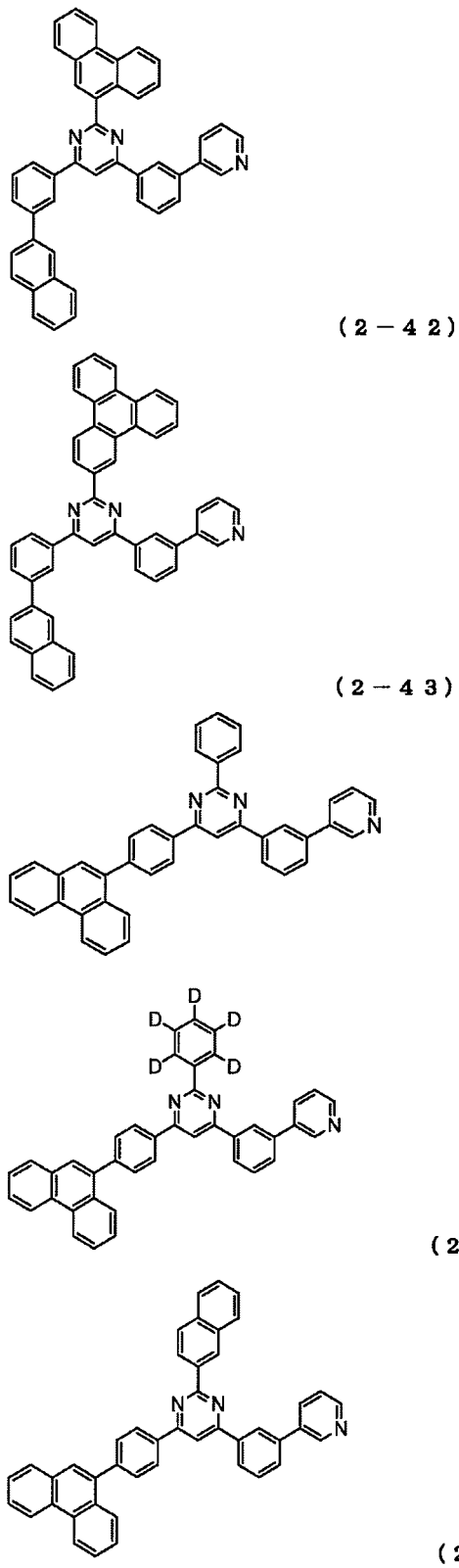
FIG. 34 is a view showing the structural formulas of Compounds No. (2-42) to (2-46) in the pyrimidine compound of the general formula (2).
Figure 35:
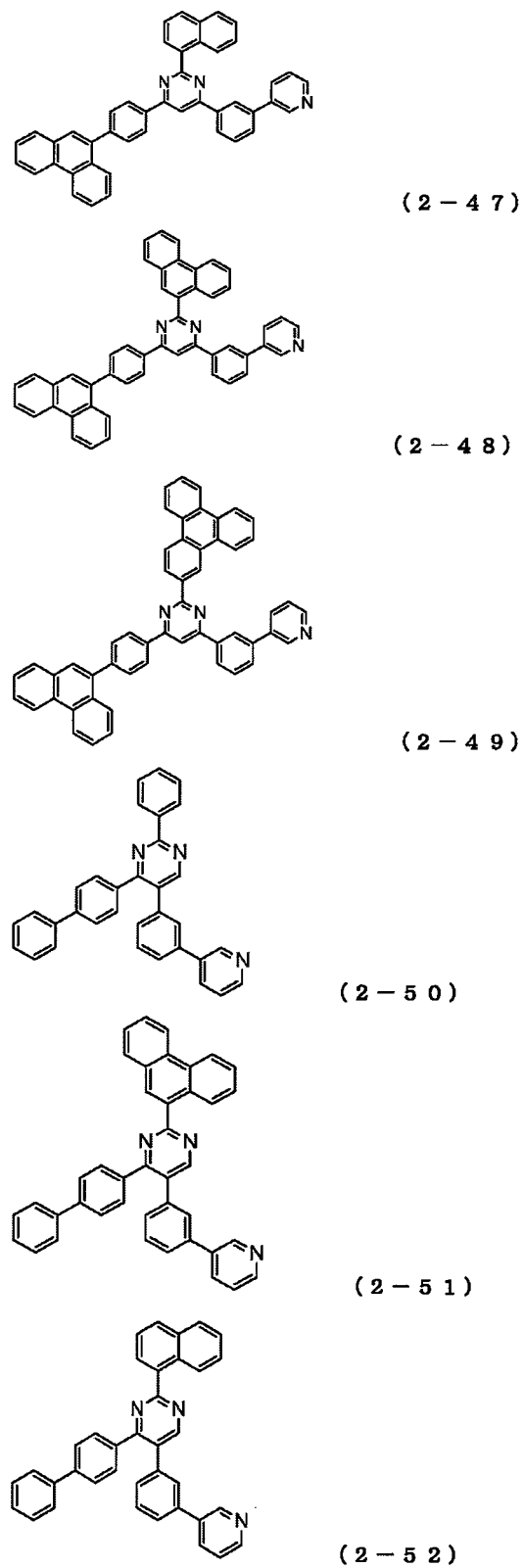
FIG. 35 is a view showing the structural formulas of Compounds No. (2-47) to (2-52) in the pyrimidine compound of the general formula (2).
Figure 36:
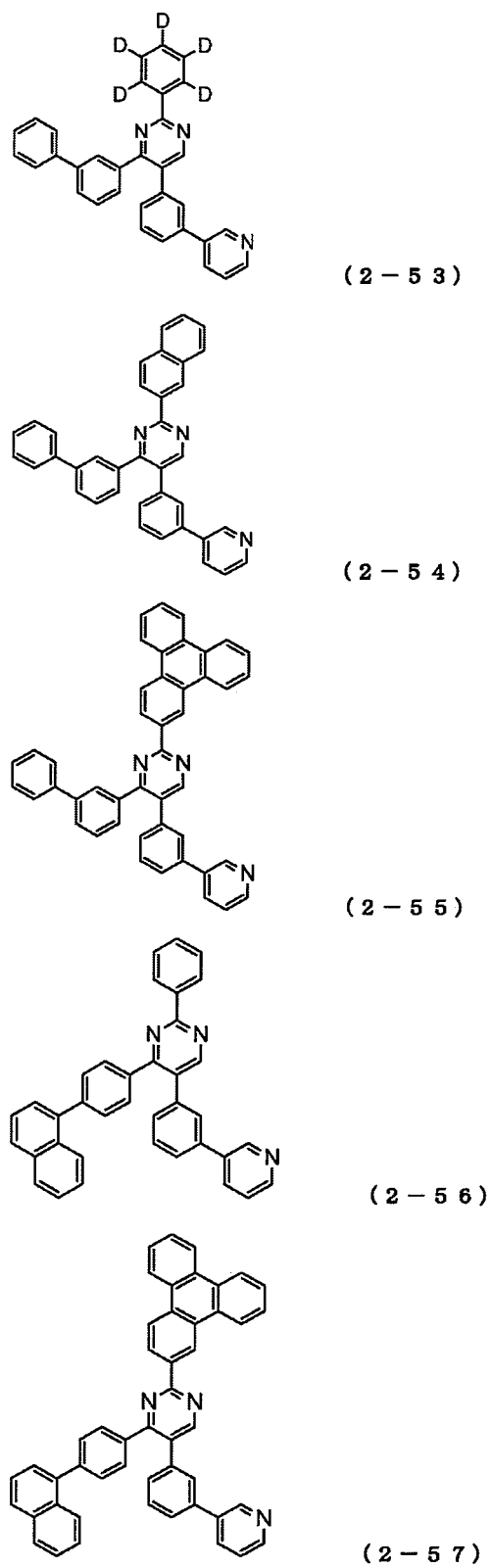
FIG. 36 is a view showing the structural formulas of Compounds No. (2-53) to (2-57) in the pyrimidine compound of the general formula (2).
Figure 37:
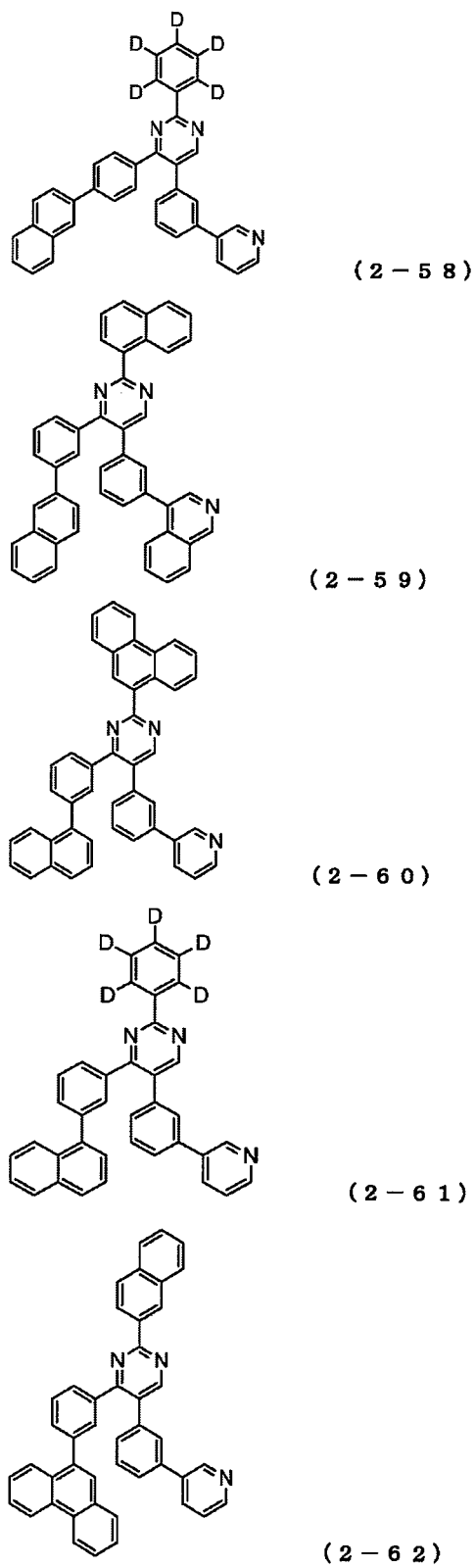
FIG. 37 is a view showing the structural formulas of Compounds No. (2-58) to (2-62) in the pyrimidine compound of the general formula (2).
Figure 38:
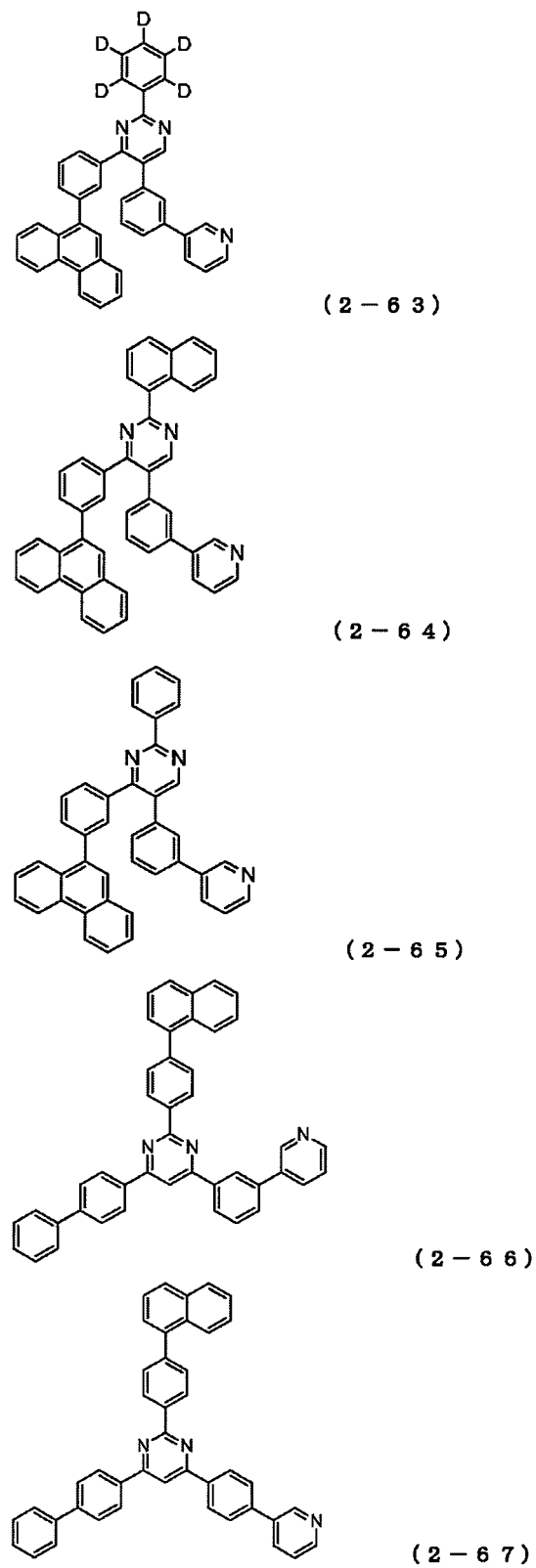
FIG. 38 is a view showing the structural formulas of Compounds No. (2-63) to (2-67) in the pyrimidine compound of the general formula (2).
Figure 39:
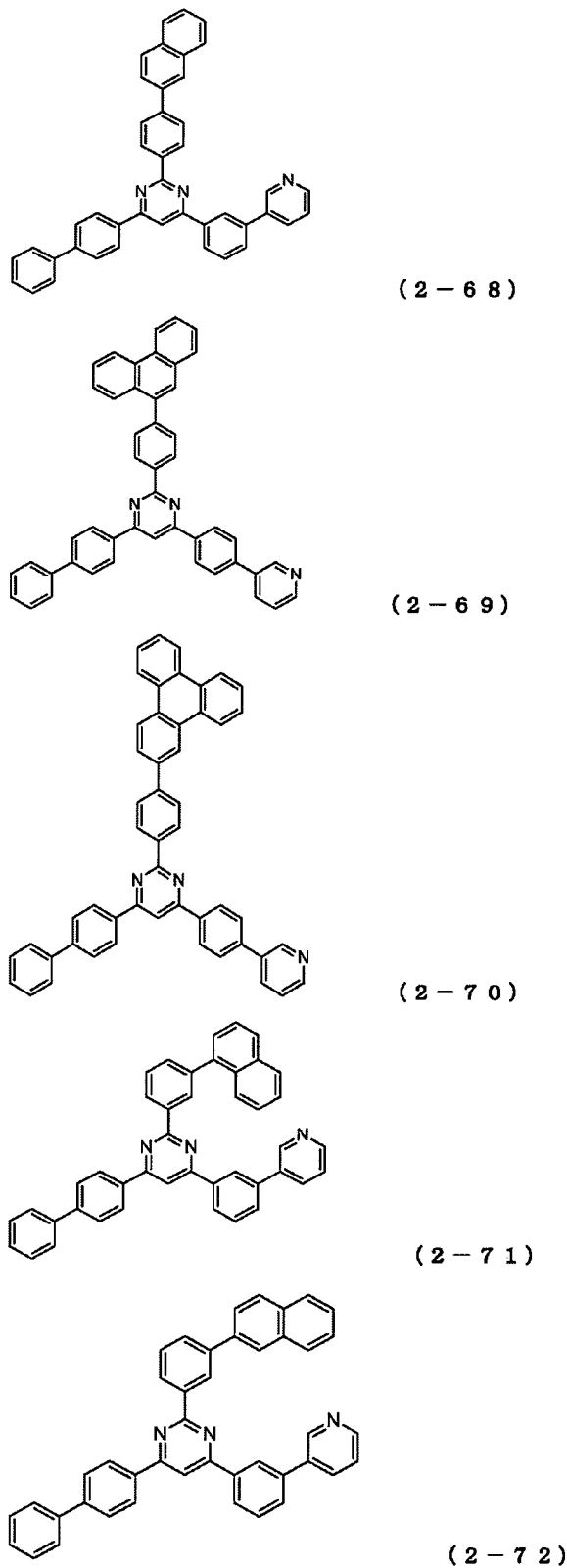
FIG. 39 is a view showing the structural formulas of Compounds No. (2-68) to (2-72) in the pyrimidine compound of the general formula (2).
Figure 40:
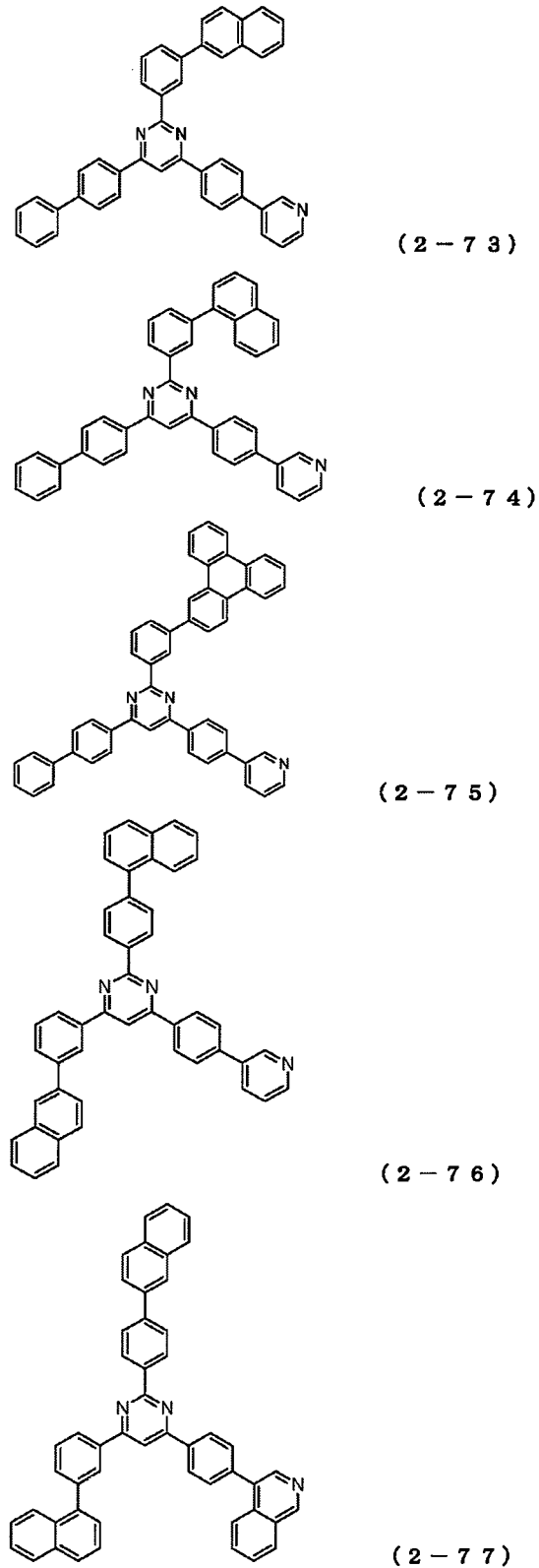
FIG. 40 is a view showing the structural formulas of Compounds No. (2-73) to (2-77) in the pyrimidine compound of the general formula (2).
Figure 41:
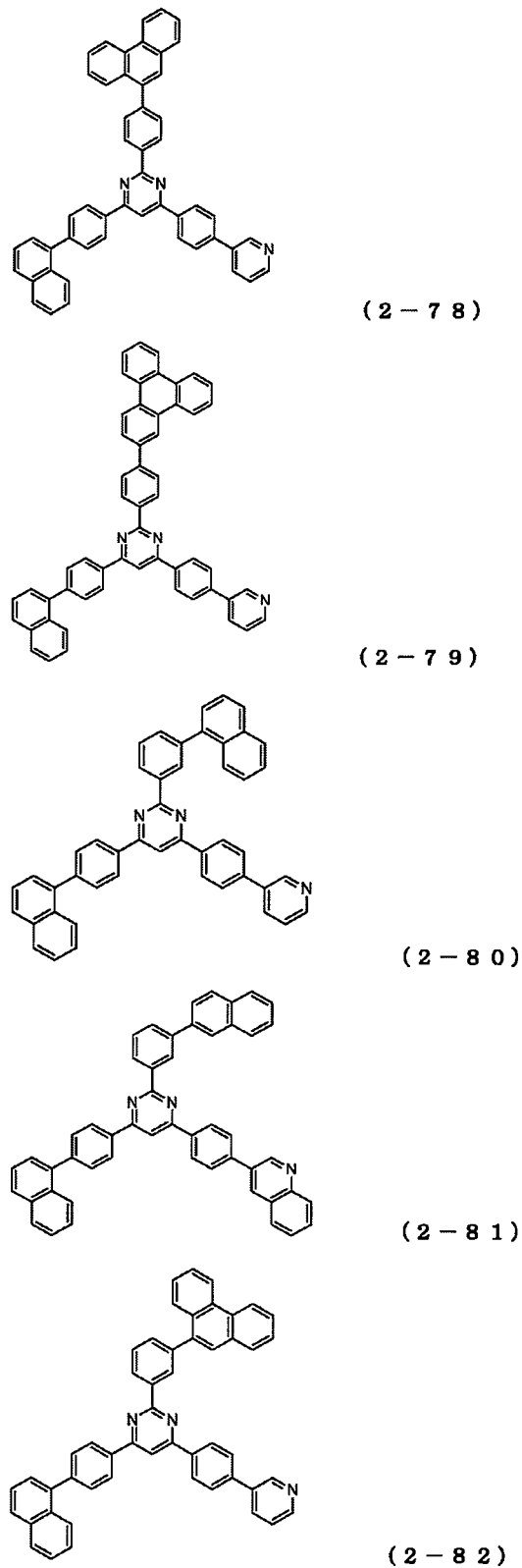
FIG. 41 is a view showing the structural formulas of Compounds No. (2-78) to (2-82) in the pyrimidine compound of the general formula (2).
Figure 42:
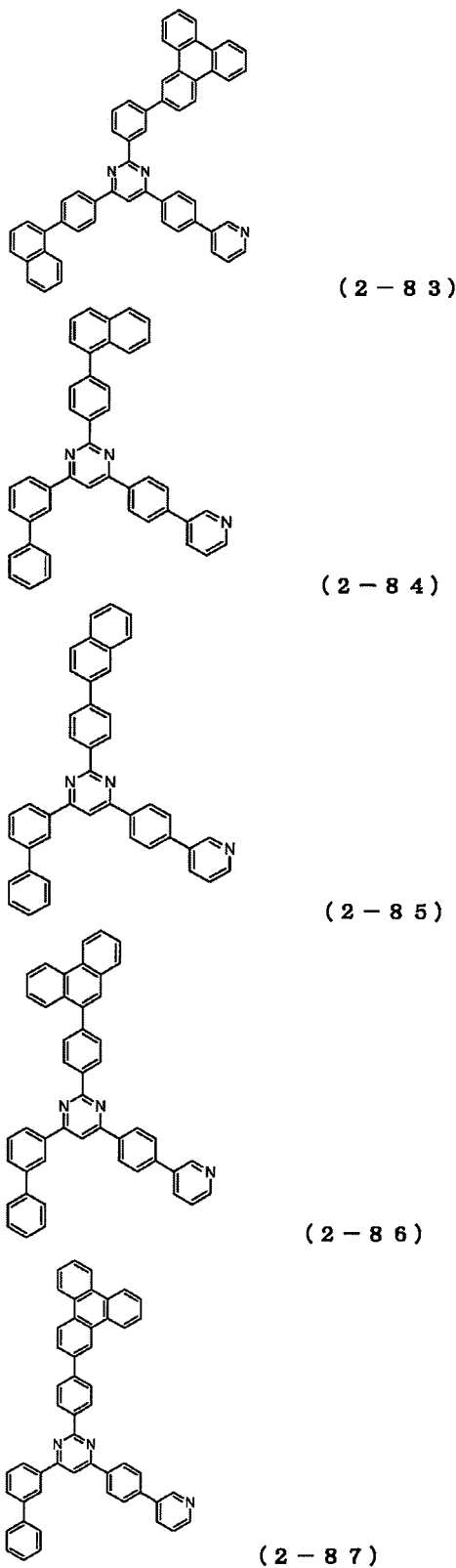
FIG. 42 is a view showing the structural formulas of Compounds No. (2-83) to (2-87) in the pyrimidine compound of the general formula (2).
Figure 43:
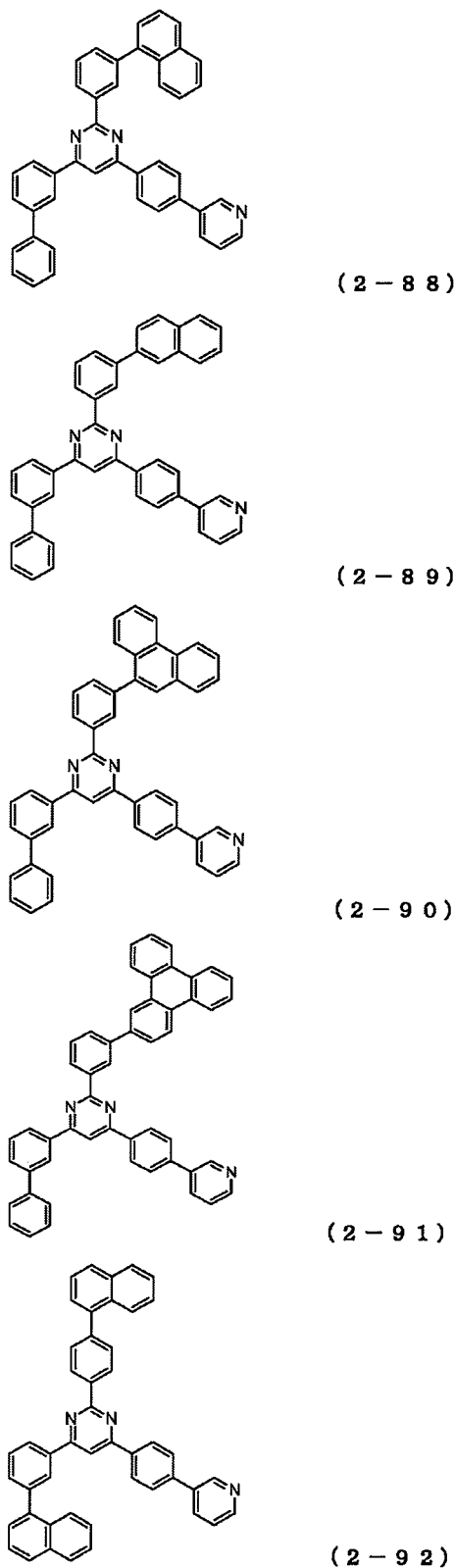
FIG. 43 is a view showing the structural formulas of Compounds No. (2-88) to (2-92) in the pyrimidine compound of the general formula (2).
Figure 44:
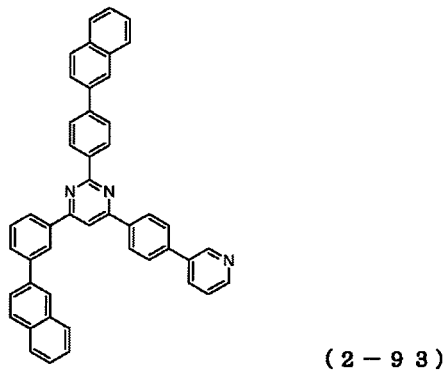
FIG. 44 is a view showing the structural formulas of Compounds No. (2-93) to (2-96) in the pyrimidine compound of the general formula (2).
Figure 44:
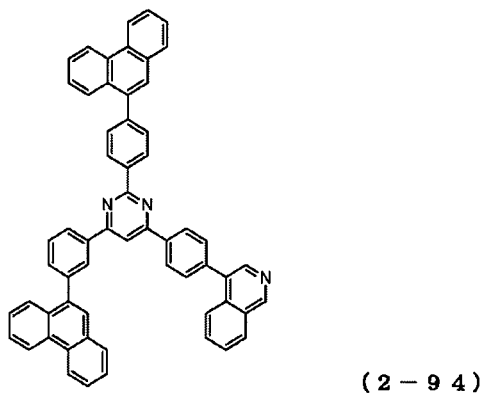
Figure 44:
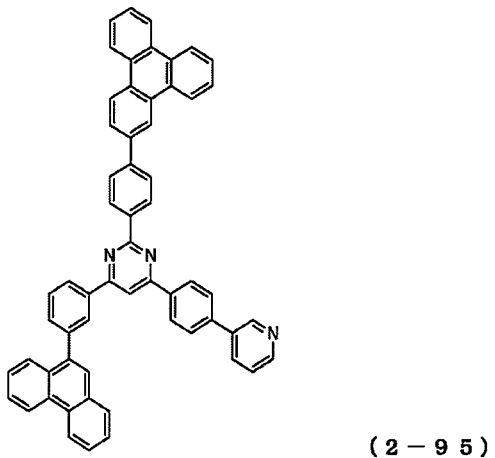
Figure 44:
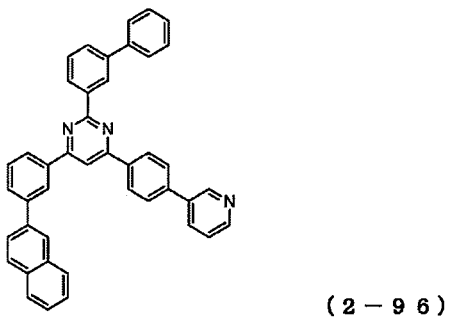
Figure 45:
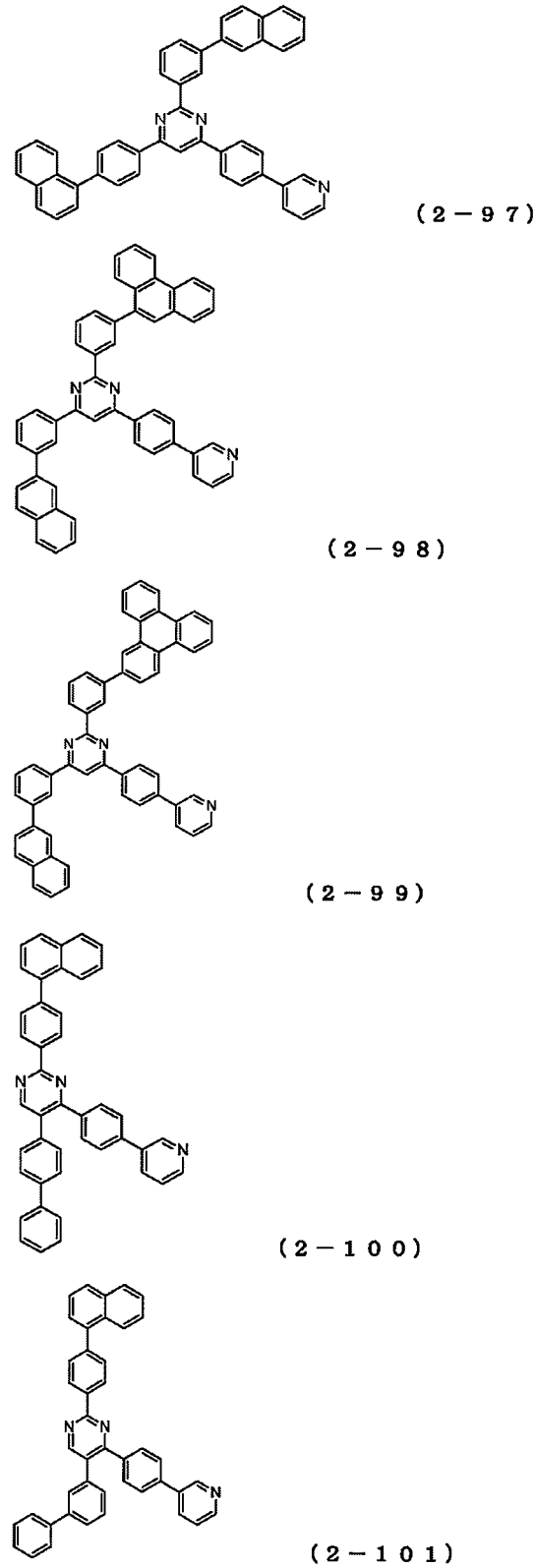
FIG. 45 is a view showing the structural formulas of Compounds No. (2-97) to (2-101) in the pyrimidine compound of the general formula (2).
Figure 46:
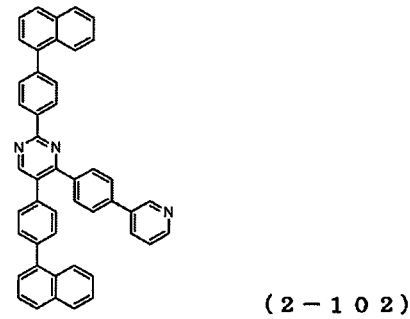
FIG. 46 is a view showing the structural formulas of Compounds No. (2-102) to (2-106) in the pyrimidine compound of the general formula (2).
Figure 46:
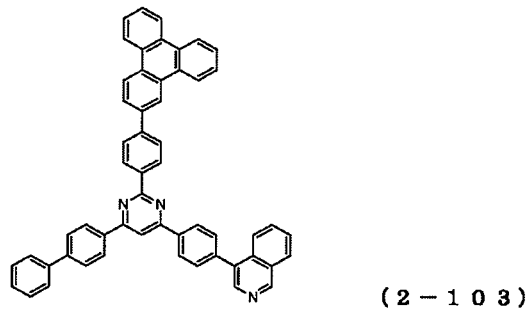
Figure 46:
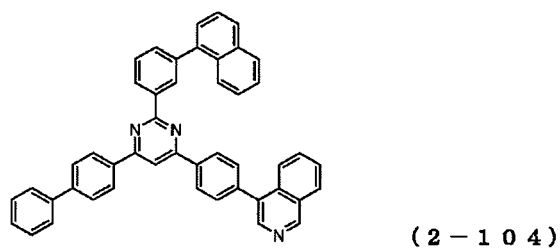
Figure 46:
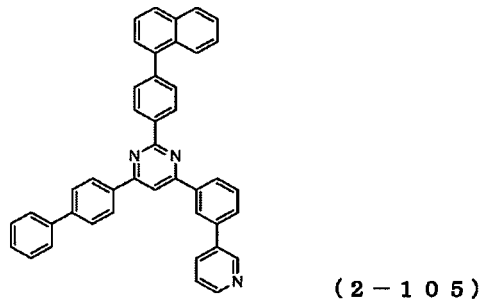
Figure 46:
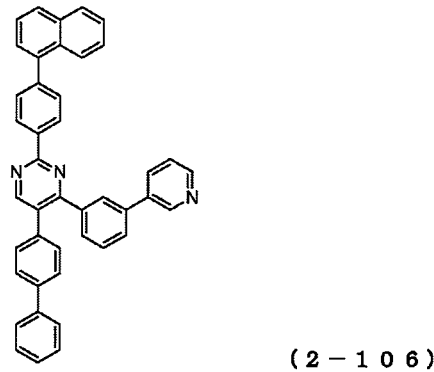
Figure 47:
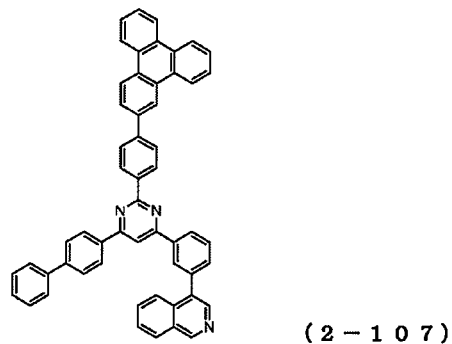
FIG. 47 is a view showing the structural formulas of Compounds No. (2-107) to (2-111) in the pyrimidine compound of the general formula (2).
Figure 47:
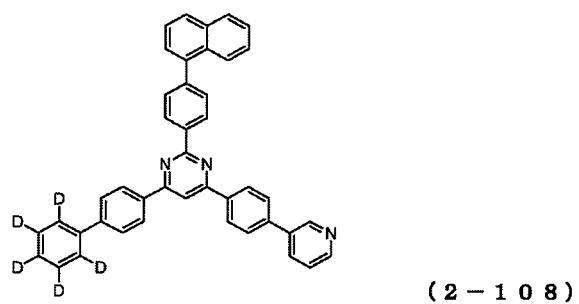
Figure 47:
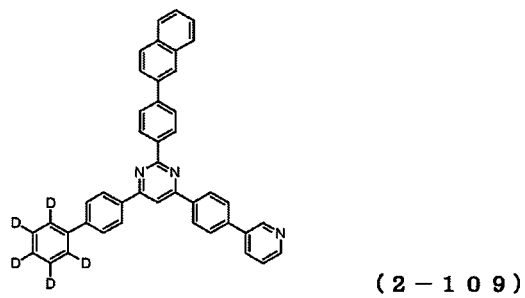
Figure 47:
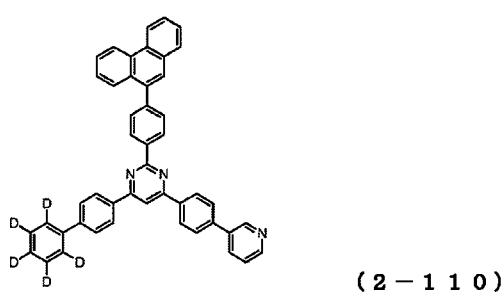
Figure 47:
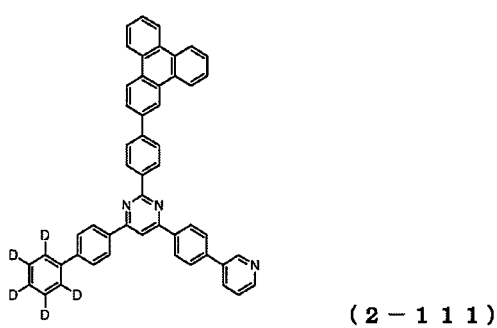
Figure 48:
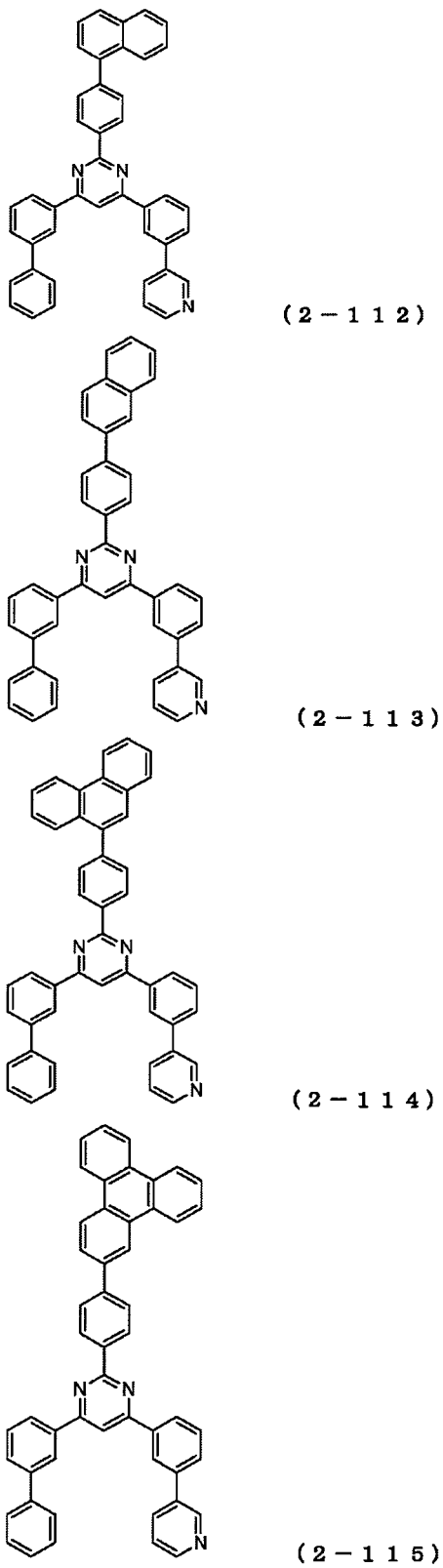
FIG. 48 is a view showing the structural formulas of Compounds No. (2-112) to (2-115) in the pyrimidine compound of the general formula (2).
Figure 49:
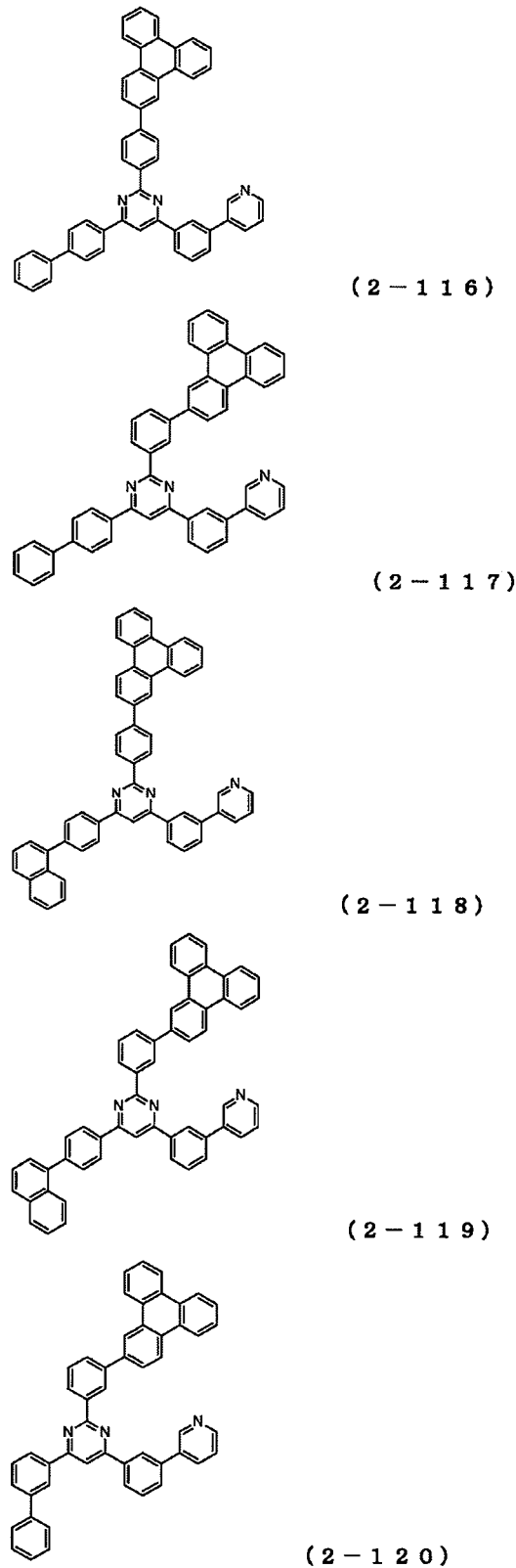
FIG. 49 is a view showing the structural formulas of Compounds No. (2-116) to (2-120) in the pyrimidine compound of the general formula (2).
Figure 50:
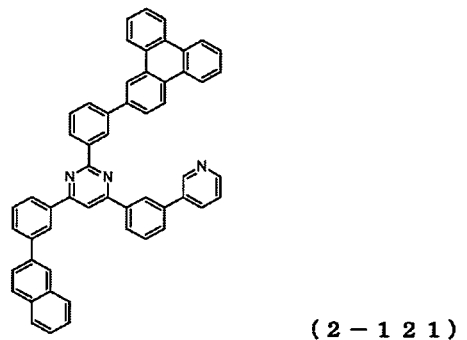
FIG. 50 is a view showing the structural formulas of Compounds No. (2-121) to (2-125) in the pyrimidine compound of the general formula (2).
Figure 50:
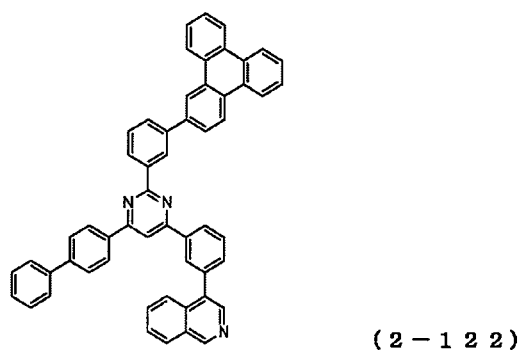
Figure 50:
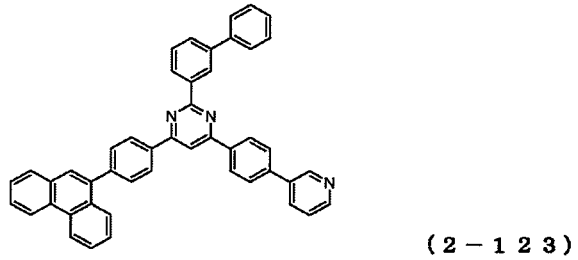
Figure 50:
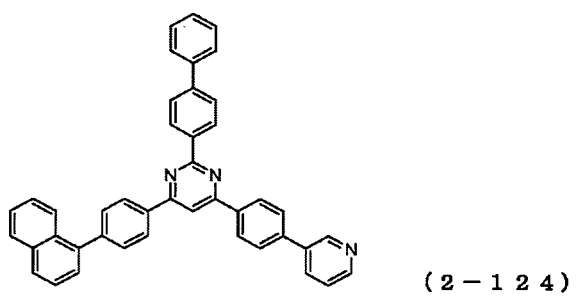
Figure 50:
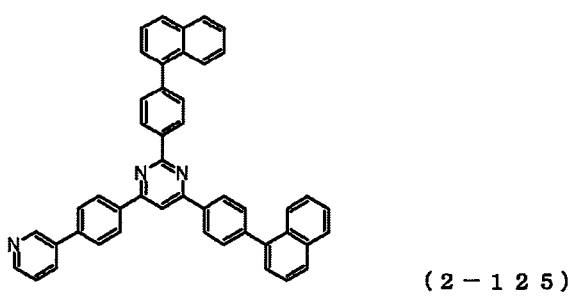

Further, Compounds (5'-1) and (5'-2) which have the structural formulas shown in FIG. 26 and have two triarylamine skeletons are not the di(triarylamine) compounds represented by the general formula (5), but can be advantageously used for forming the first hole transport layer 4.

The thickness of the second hole transport layer 5 formed using the arylamine derivative of the above-described general formula (1) and the thickness of the first hole transport layer 4 formed using another triarylamine compound are not particularly limited, but in order to maximize the characteristics of these layers, the total thickness (t1+t2) of the thickness t1 of the first hole transport layer 4 and the thickness t2 of the second hole transport layer 5 is usually within a range of 20 nm to 300 nm, preferably within a range of 50 nm to 200 nm, particularly within a range of 50 nm to 150 nm, these ranges ensuring light emission at a low driving voltage.

In the present invention, various arylamine derivatives and triarylamine compounds exemplified hereinabove can be synthesized by publicly known methods (see, for example, Japanese Patent Application Publication No. H7-126615, Japanese Patent Application Publication No. H8-048656, and Japanese Patent Application Publication No. 2005-108804).

Further, the above-described first hole transport layer 4 and second hole transport layer 5 are preferably formed by vapor deposition or vapor co-deposition of a gas including a predetermined triarylamine compound or arylamine derivative, but they can be also formed by a publicly known method such as a spin coating method and an ink jet method.
<Luminous Layer 6>

The luminous layer 6 is the same as that used in the conventional publicly known organic EL devices and can be formed by a publicly known method such as a vapor deposition method, a spin coating method, and an ink jet method selected according to the type of the material used.

For example, metal complexes of a quinolinol derivative such as $Alq_3$, various metal complexes, anthracene derivatives, bis-styrylbenzene derivatives, pyrene derivatives, oxazole derivatives, polyparaphenylene vinylene derivatives, thiazole derivatives, benzimidazole derivatives, polydialkylfluorene derivatives, quinazoline derivatives and the like can be used singly or in combinations of two or more thereof as the luminous material for forming the luminous layer 6. Further, compounds having electron transport property, for example, p-bis(triphenylsilyl)benzene (UGH2) and 2,2'2"-(1,3,5-phenylene)-tris(1-phenyl-1H-benzimidazole) (TPBI) can also be used.

Further, the luminous layer 6 can be composed of a host material and a dopant.

In this case, anthracene derivatives are preferably used as the host material, but thiazole derivatives, benzimidazole derivatives, polydialkylfluorene derivatives and the like can also be used.

Further, pyrene derivatives with blue luminous property can be most advantageously used as the dopant, but quinacridone, coumarin, rubrene, perylene, and derivatives thereof; benzopyran derivatives; rhodamine derivatives; aminostyrene derivatives; and the like can be also used.

A phosphorescent luminous body can be also used as the luminous material. Metal complexes including iridium, platinum, or the like are typical representative of such phosphorescent luminous bodies, and phosphorescent luminous bodies of such metal complexes are exemplified by red phosphorescent luminous bodies such as bis(3-methyl-2-phenylquinoline)iridium (III) acetyl acetonate (Ir(3'-Mepq)$_2$(acac)), Ir(piq)$_3$, and Btp$_2$Ir(acac), green phosphorescent luminous bodies such as Ir(ppy)$_3$, and blue phosphorescent luminous bodies such as FIrpic and FIr6.

A carbazole derivative such as 4,4'-di(N-carbazolyl)biphenyl (CBP), TCTA, and mCP can be used as a hole injection/transport host material when such phosphorescent luminous bodies are used. Further, p-bis(triphenylsilyl)benzene (UGH2), 2,2'2"-(1,3,5-phenylene)-tris(1-phenyl-1H-benzimidazole) (TPBI) and the like can be used as an electron transport host material.

The host material is preferably doped with the phosphorescent luminous material in an amount in a range of 1% by weight to 30% by weight relative to the whole luminous layer by co-deposition to avoid concentration quenching.

A material which emits delayed fluorescence, such as a CDCB derivative, for example, PIC-TRZ, CC2TA, PXZ-TRZ, and 4CzIPN, can be used as the luminous material (see, for example, Appl. Phys. Let., 98, 0833302).

In the present invention, the most advantageous luminous layer 6 uses a pyrene derivative with blue luminous property as a dopant.
<Electron Transport Layer 7>

In the present invention, the electron transport layer 7 provided on the above-described luminous layer 6 is formed by a publicly known method such as a vapor deposition method, a spin coating method, and an ink jet method by using an electron transport material, but it is important that the pyrimidine compound represented by the following general formula (2) be used as the electron transport material.

Thus, this pyrimidine compound excels in electron injection/transport performance and also excels in durability and stability in a thin-film state. Therefore, by using such a pyrimidine compound to form the electron transport layer 7, in combination with the hole transport layer having the aforementioned two-layer structure (the first and second hole transport layers 4 and 5), it is possible to obtain an organic EL device in which excellent carrier balance can be ensured and the performance of these layers is effectively exhibited, which has high efficiency and a low driving voltage, and in which particularly long life is realized.

The Pyrimidine Compound;

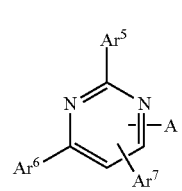

(2)

In the general formula (2), $Ar^5$ represents an aromatic hydrocarbon group or an aromatic heterocyclic group. The aromatic hydrocarbon group and the aromatic heterocyclic group may each have a condensed polycyclic structure.

Such aromatic hydrocarbon group and aromatic heterocyclic group can be exemplified by the following groups.
The Aromatic Hydrocarbon Group (Ar⁵);
  a phenyl group, a biphenyl group, a terphenyl group, a tetrakisphenyl group, a styryl group, a naphthyl group, an anthracenyl group, a phenanthrenyl group, a fluorenyl group, an indenyl group, a pyrenyl group, a perylenyl group, a fluoranthenyl group, a triphenylenyl group, a spirobifluorenyl group, etc.
  Among these aromatic hydrocarbon groups, a phenyl group, a biphenyl group, a naphthyl group, an anthracenyl group, a phenanthrenyl group, a fluorenyl group, an indenyl group, a pyrenyl group, a perylenyl group, a fluoranthenyl group, and a triphenylenyl group are preferred, and a phenyl group, a biphenyl group, a naphthyl group, a phenanthrenyl group, a fluorenyl group, a pyrenyl group, a perylenyl group, a fluoranthenyl group, a triphenylenyl group, and a spirobifluorenyl group are most preferred.
The aromatic heterocyclic group (Ar⁵);
  oxygen-containing or sulphur-containing heterocyclic groups such as a furyl group, a thienyl group, a benzofuranyl group, a benzothienyl group, a dibenzofuranyl group, a dibenzothienyl group, etc.
  Among these aromatic heterocyclic groups, a dibenzofuranyl group and a dibenzothienyl group are preferred.
  The aromatic hydrocarbon groups and the aromatic heterocyclic groups may have a substituent. The substituents can be exemplified by the same ones as those illustrated as the substituents optionally possessed by the groups Ar¹ to Ar⁴ (aromatic hydrocarbon groups or aromatic heterocyclic groups) in the general formula (1).
  In particular, when the aromatic hydrocarbon group is a phenyl group, it is preferred that the phenyl group have a substituent. A phenyl group, a naphthyl group, a phenanthrenyl group, a pyrenyl group, a fluoranthenyl group, a triphenylenyl group, and a spirobifluorenyl group are preferred as the substituent possessed by the phenyl group.
  Ar⁶ and Ar⁷ in the general formula (2) each represent a hydrogen atom, an aromatic hydrocarbon group, or an aromatic heterocyclic group; Ar⁶ and Ar⁷ may not each be a hydrogen atom at the same time.
  The aromatic hydrocarbon groups and the aromatic heterocyclic groups in the Ar⁶ and Ar⁷ can be exemplified by the same ones as those illustrated with respect to the group Ar⁵. Further, the aromatic hydrocarbon groups and the aromatic heterocyclic groups may further have a substituent and the types of the substituent are exactly the same as those illustrated with respect to the group Ar⁵.
  Further, A in the general formula (2) is a monovalent organic group represented by the following general formula (3).

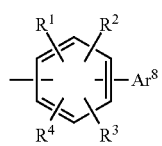

(3)

In the formula,
Ar⁸ represents an aromatic heterocyclic group;
R¹ to R⁴ each represent a hydrogen atom, a deuterium atom, a fluorine atom, a chlorine atom, a cyano group, a trifluoromethyl group, an alkyl group having 1 to 6 carbon atoms, an aromatic hydrocarbon group, or an aromatic heterocyclic group.
  The aromatic heterocyclic group represented by the Ar⁸ also may have a condensed polycyclic structure.
  The aromatic heterocyclic group represented by the Ar⁸ can be exemplified by the following groups.
The Aromatic Heterocyclic Group (Ar⁸);
  a triazinyl group, a pyridyl group, a pyrimidinyl group, a furyl group, a pyrrolyl group, a thienyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzimidazolyl group, a pyrazolyl group, a dibenzofuranyl group, a dibenzothienyl group, an azafluorenyl group, a diazafluorenyl group, a naphthyridinyl group, a phenanthrolinyl group, an acridinyl group, a carbolinyl group, an azaspirobifluorenyl group, a diazaspirobifluorenyl group, etc.
  Among the aromatic heterocyclic groups, nitrogen-containing aromatic heterocyclic groups, for example, a triazinyl group, a pyridyl group, a pyrimidinyl group, a pyrrolyl group, a quinolyl group, an isoquinolyl group, an indolyl group, a carbazolyl group, a benzoxazolyl group, a benzothiazolyl group, a quinoxalinyl group, a benzimidazolyl group, a pyrazolyl group, an azafluorenyl group, a diazafluorenyl group, a naphthyridinyl group, a phenanthrolinyl group, an acridinyl group, a carbolinyl group, an azaspirobifluorenyl group, and a diazaspirobifluorenyl group are preferred.
  More preferred aromatic heterocyclic groups are a triazinyl group, a pyridyl group, a pyrimidinyl group, a quinolyl group, an isoquinolyl group, an indolyl group, a carbazolyl group, a quinoxalinyl group, a benzimidazolyl group, an azafluorenyl group, a diazafluorenyl group, a naphthyridinyl group, a phenanthrolinyl group, an acridinyl group, an azaspirobifluorenyl group, and a diazaspirobifluorenyl group.
  The most preferred aromatic heterocyclic groups are a pyridyl group, a pyrimidinyl group, a quinolyl group, an isoquinolyl group, an indolyl group, a quinoxalinyl group, a benzimidazolyl group, an azafluorenyl group, a diazafluorenyl group, a naphthyridinyl group, a phenanthrolinyl group, an acridinyl group, an azaspirobifluorenyl group, and a diazaspirobifluorenyl group.
  Further, the aromatic heterocyclic groups may also have a substituent. The substituents can be exemplified by the same ones as those illustrated as the substituents optionally possessed by the groups Ar¹ to Ar⁴ (aromatic hydrocarbon groups or aromatic heterocyclic groups) in the general formula (1).
  Further, in the general formula (3), the alkyl groups having 1 to 6 carbon atoms and represented by R¹ to R⁴ can be exemplified by the same ones as those illustrated in relation to the groups R⁵ to R¹⁶ in the aforementioned general formula (4).
  Furthermore, the aromatic hydrocarbon groups and the aromatic heterocyclic groups represented by R¹ to R⁴ in the general formula (3) can be exemplified by the same ones as those illustrated in relation to the group Ar⁵ in the general formula (2).
  It is preferred that the groups Ar⁵ to Ar⁷ and the group A bonded to the pyrimidine ring in the pyrimidine compound of the above-described general formula (2) be bonded at positions shown in the following formula (2a) or (2b).

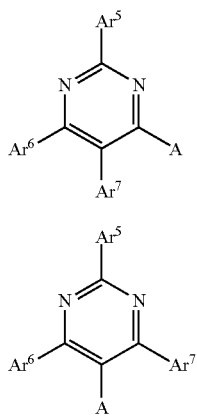

(2a)

(2b)

In the formulas, $Ar^5$ to $Ar^7$ and A are as defined hereinabove.

A group in which the group $Ar^8$ and the groups $R^1$ to $R^4$ are bonded to a benzene ring at positions shown in the following formula (3a) is preferred as the group A represented by the general formula (3).

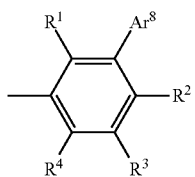

(3a)

In the formula, $Ar^8$ and $R^1$ to $R^4$ are as defined hereinabove.

The pyrimidine compound represented by the above-described general formula (2) can be specifically exemplified by Compounds (2-1) to (2-125) having structural formulas shown in FIGS. 27 to 50.

In the present invention, the pyrimidine compound represented by the above-described general formula (2) can be synthesized by a publicly known method (see, for example, Korean Patent Publication No. 2013-060157).

In the present invention, the electron transport layer 7 is formed using the pyrimidine compound represented by the above-described general formula (2), but publicly known electron transport materials may be used in combination therewith as long as excellent characteristics of the pyrimidine compound are not impaired.

For example, metal complexes of quinolinol derivatives such as $Alq_3$, various metal complexes including zinc, beryllium, aluminum, etc., triazole derivatives, triazine derivatives, oxadiazole derivatives, thiadiazole derivatives, carbodiimido derivatives, quinoxaline derivatives, phenanthroline derivatives, and silole derivatives can be used in combination with the pyrimidine compound for forming the electron transport layer 7.

Further, a laminate including a layer formed by a film forming process using the pyrimidine compound and a layer formed by a film forming process using another electron transport material can be also used as the electron transport layer 7.

<Electron Injection Layer 8>

The electron injection layer 8 is appropriately provided between the cathode 9 and the electron transport layer 7. The electron injection layer 8 can be formed using, for example, an alkali metal salt such as lithium fluoride and cesium fluoride, an alkaline earth metal salt such as magnesium fluoride and a metal oxide such as aluminum oxide.

<Cathode 9>

A metal with a low work function, such as aluminum, and alloys with a lower work function such as a magnesium-silver alloy, a magnesium-indium alloy, and an aluminum-magnesium alloy can be used as the electrode material of the cathode 9 in the organic EL device of the present invention.

<Other Layers>

The organic EL device of the present invention may have other layers, if necessary, in addition to the above-described layers. For example, an electron blocking layer can be provided between the second hole transport layer 5 and the luminous layer 6, and a hole blocking layer can be provided between the luminous layer 6 and the electron transport layer 7 (these configurations are not shown in FIG. 1).

These appropriately provided layers may be formed from publicly known materials by a publicly known method such as a vapor deposition method, a spin coating method, and an ink jet method selected according to the type of the material to be used.

The Electron Blocking Layer;

The electron blocking layer which is appropriately provided between the second hole transport layer 5 and the luminous layer 6 is formed to block the transmission of electrons from the luminous layer 6 and increase the luminous efficiency. Various compounds having electron blocking property can be used as the material for forming the electron blocking layer, the following carbazole derivatives being typical such compounds.

4,4',4"-tri(N-carbazolyl)triphenylamine (TCTA);
9,9-bis[4-(carbazol-9-yl)phenyl]fluorene;
1,3-bis(carbazol-9-yl)benzene (mCP); and
2,2-bis(4-carbazol-9-ylphenyl)adamantane (Ad-Cz).

In addition to the above-mentioned carbazole derivatives, compounds having a triphenylsilyl group and a triarylamine skeleton in a molecule, for example, 9-[4-(carbazol-9-yl)phenyl]-9-[4-(triphenylsilyl)phenyl]-9H-fluorene, can be also used as materials for forming the electron blocking layer.

The Hole Blocking Layer;

The hole blocking layer appropriately provided between the electron transport layer 7 and the luminous layer 6 is formed to prevent the transmission of holes from the luminous layer 6 and increase the luminous efficiency. The following compounds demonstrating the hole blocking action can be used as materials for forming the hole blocking layer: phenanthroline derivatives such as bathocuproine (BCP), metal complexes of quinolinol derivatives such as aluminum(III) bis(2-methyl-8-quinolinato)-4-phenylphenolate (BAlq), various rare earth complexes, triazole derivatives, triazine derivatives, and oxadiazole derivatives.

In the organic EL device of the present invention which is formed from the above-described layers, the second hole transport layer 5 is formed using an arylamine derivative represented by the general formula (1) and the electron transport layer 7 is formed using the pyrimidine compound of the general formula (2). Therefore, holes and electrons can be injected into the luminous layer 6 with good efficiency. As a result, optimum carrier balance is ensured and characteristics of the organic EL device are greatly improved.

EXAMPLES

The mode for carrying out the present invention is specifically described hereinbelow by examples, but the present invention is not intended to be limited to these examples.

Synthesis Example 1

Synthesis of an Arylamine Derivative (Compound 1-5)

the following components were added to a nitrogen-purged reactor, heated, and stirred for 16 h at 70° C.

| | |
|---|---|
| N-(biphenyl-4-yl)-N-(4-bromophenyl)aniline | 8.0 g, |
| N-(9,9-dimethyl-9H-fluoren-2-yl)-N-{3'-(4,4,5,5-tetramethyl-[1,3,2]dioxaboran-2-yl)biphenyl-4-yl}aniline | 11.4 g, |
| potassium carbonate | 7.5 g, |
| water | 64 mL, |
| toluene | 64 mL, |
| ethanol | 16 mL, |
| and | |
| tetrakis(triphenylphosphine)palladium | 0.8 g. |

The above-mentioned heating was followed by cooling to room temperature, ethyl acetate and water were added, and the organic layer was then collected by liquid separation.

After concentrating the organic layer, recrystallization using a mixed solvent of THF/acetone was performed to obtain 9.54 g (yield 69%) of a white powder of an arylamine derivative (Compound 1-5) to be used for forming the second hole transport layer.

This arylamine derivative (Compound 1-5) is 4-{(biphenyl-4-yl)-phenylamino}-4"-{(9,9-dimethyl-9H-fluoren-2-yl)-phenylamino}-1,1':3',1"-terphenyl, which is represented by the following formula.

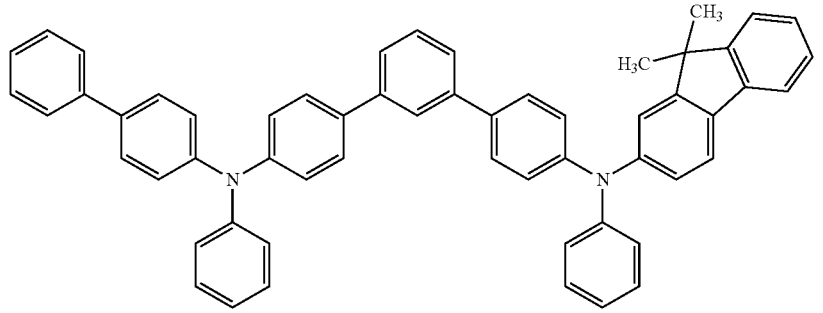

(1-5)

The structure of the obtained white powder was identified using NMR.

The following 44 hydrogen signals were detected with $^1$H-NMR (THF-$d_8$).

δ (ppm)=7.86 (1H)
7.68-6.97 (37H)
1.41 (6H)

Synthesis Example 2

Synthesis of an Arylamine Derivative (Compound 1-6)

a total of 7.88 g (yield 62%) of a light-yellow powder of an arylamine derivative (Compound 1-6) to be used for forming the second hole transport layer was obtained by the same operations as in Synthesis Example 1, except that
N-(3'-bromobiphenyl-4-yl)-N-(naphthalen-1-yl)aniline and
4-{N-(9,9-dimethyl-9H-fluoren-2-yl)-phenylamino}-phenylboronic acid
were used instead of
N-(biphenyl-4-yl)-N-(4-bromophenyl)aniline and
N-(9,9-dimethyl-9H-fluoren-2-yl)-N-{3'-(4,4,5,5-tetramethyl-[1,3,2]dioxaboran-2-yl)biphenyl-4-yl}aniline.

This arylamine derivative (Compound 1-6) is 4-{(9,9-dimethyl-9H-fluoren-2-yl)-phenylamino}-4"-{(naphthalen-1-yl)-phenylamino}-1,1':3',1"-terphenyl, which is represented by the following formula.

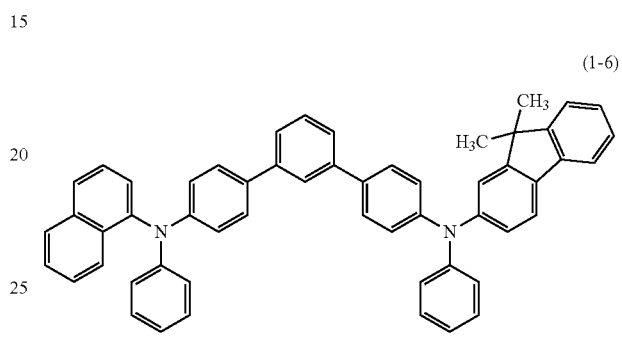

(1-6)

The structure of the obtained light-yellow powder was identified using NMR.

The following 42 hydrogen signals were detected with $^1$H-NMR (CDCl$_3$).

δ (ppm)=7.98 (1H)
7.92 (1H)
7.84-7.75 (2H)
7.70-6.94 (32H)
1.49 (6H)

Synthesis Example 3

Synthesis of an Arylamine Derivative (Compound 1-21)

the following components were added to a nitrogen-purged reactor, and a nitrogen gas was circulated therethrough while irradiating with ultrasonic waves for 30 min.

| | |
|---|---|
| 1,4-dibromobenzene | 6.20 g, |
| N-(biphenyl-4-yl)-N-{3-(4,4,5,5-tetramethyl-[1,3,2]dioxaboran-2-yl)phenyl}aniline | 25.1 g, |

-continued

| | |
|---|---|
| potassium carbonate | 10.8 g, |
| water | 39 mL, |
| toluene | 380 mL, |
| and ethanol | 95 mL. |
| Then, tetrakis(triphenylphosphine)palladium | 0.95 g | was added, followed by heating and reflux stirring for 18 h.

Cooling to room temperature was then performed, 200 mL of water and 190 mL of heptane were added, and the precipitate was then collected by filtration.

The precipitate was heated and dissolved in 1200 mL of 1,2-dichlorobenzene, purified by adsorption using 39 g of silica gel, and then purified by adsorption using 19 g of activated clay. A total of 725 mL of methanol was then added, and the precipitated crude product was collected by filtration.

This crude product was repeatedly subjected to crystallization using a mixed solvent of 1,2-dichlorobenzene/methanol, followed by reflux washing using 300 mL of methanol to obtain 15.22 g (yield 81%) of a white powder of an arylamine derivative (Compound 1-21) to be used for forming the second hole transport layer.

This arylamine derivative (Compound 1-21) is 3,3"-bis{(biphenyl-4-yl)-phenylamino}-1,1':4',1"-terphenyl, which is represented by the following formula.

This arylamine derivative (Compound 1-22) is 2,2"-bis{(biphenyl-4-yl)-phenylamino}-1,1':4',1"-terphenyl, which is represented by the following formula.

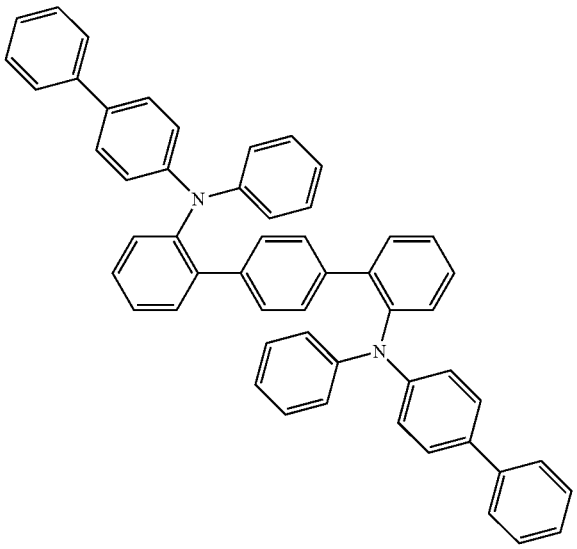

(1-22)

The structure of the obtained white powder was identified using NMR.

(1-21)

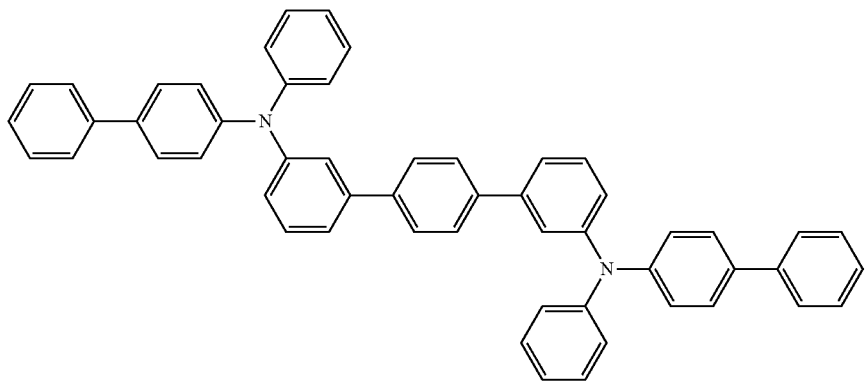

The structure of the obtained white powder was identified using NMR.

The following 40 hydrogen signals were detected with $^1$H-NMR (CDCl$_3$).

δ (ppm)=7.61 (2H)
7.56-6.83 (38H)

Synthesis Example 4

Synthesis of an Arylamine Derivative (Compound 1-22)

a total of 11.11 g (yield 58%) of a white powder of an arylamine derivative (Compound 1-22) to be used for forming the second hole transport layer was obtained by the same operations as in Synthesis Example 3, except that N-(biphenyl-4-yl)-N-{2-(4,4,5,5-tetramethyl-[1,3,2]dioxaboran-2-yl)phenyl}aniline
was used instead of
N-(biphenyl-4-yl)-N-{3-(4,4,5,5-tetramethyl-[1,3,2]dioxaboran-2-yl)phenyl}aniline.

The following 40 hydrogen signals were detected with $^1$H-NMR (THF-d$_8$).

δ (ppm)=7.52 (4H)
7.40-7.20 (18H)
7.03 (8H)
6.90-6.75 (10H)

Synthesis Example 5

Synthesis of an Arylamine Derivative (Compound 1-32)

the following components were added to a nitrogen-purged reactor, heated, and stirred overnight at 100° C.

| | |
|---|---|
| N-(biphenyl-4-yl)-N-(2"-bromo-1,1':4',1"-terphenyl-4-yl)aniline | 10.0 g, |
| 2-(phenylamino)-9,9-dimethyl-9H-fluorene | 6.2 g, |
| palladium acetate | 0.081 g, |

-continued

| | |
|---|---|
| t-butoxysodium | 3.5 g, |
| 50% (w/v) toluene solution of tri-t-butylphosphine and | 0.146 g, |
| toluene | 100 mL. |

Insolubles were then removed by filtration, followed by concentration and then purification using column chromatography (carrier: silica gel, eluent: heptane/dichloromethane) to obtain 4.77 g (yield 35%) of a white powder of an arylamine derivative (Compound 1-32) to be used for forming the second hole transport layer.

This arylamine derivative (Compound 1-32) is 4-{(biphenyl-4-yl)-phenylamino}-2"-{(9,9-dimethyl-9H-fluoren-2-yl)-phenylamino}-1,1':4',1"-terphenyl, which is represented by the following formula.

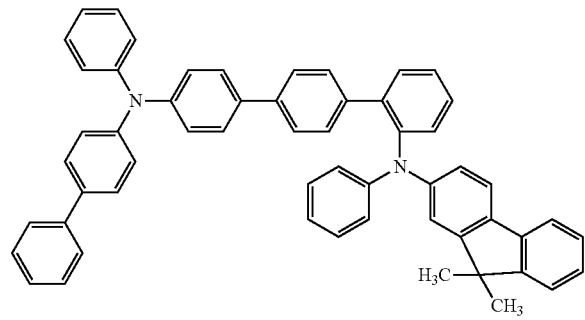

(1-32)

The structure of the obtained white powder was identified using NMR.
The following 44 hydrogen signals were detected with $^1$H-NMR (THF-$d_8$).
δ (ppm)=7.61-7.48 (4H)
7.42-6.92 (32H)
6.81 (1H)
6.76 (1H)
1.28 (6H)

Synthesis Example 6

Synthesis of an Arylamine Derivative (Compound 1-34)

the following components were added to a nitrogen-purged reactor, heated, and reflux stirred for 2 h.

| | |
|---|---|
| 4,4"-dibromo-1,1':3',1"-terphenyl | 8.81 g, |
| 2-(phenylamino)-9,9-dimethyl-9H-fluorene | 13.6 g, |
| t-butoxysodium | 5.12 g, |
| tris(dibenzylideneacetone)dipalladium and | 0.33 g, |
| 50% (w/v) toluene solution of tri-t-butylphosphine | 0.63 mL. |

Then, after natural cooling, methanol was added and the precipitate was collected by filtration. The precipitate was heated and dissolved, purified by adsorption using silica gel, and then purified by adsorption using activated clay. Crystallization using a mixed solvent of chlorobenzene/methanol was then performed, followed by reflux washing using methanol to obtain 16.25 g (yield 90%) of a white powder of an arylamine derivative (Compound 1-34) to be used for forming the second hole transport layer.

This arylamine derivative (Compound 1-34) is 4,4"-bis{(9,9-dimethyl-9H-fluoren-2-yl)-phenylamino}-1,1':3', 1"-terphenyl, which is represented by the following formula.

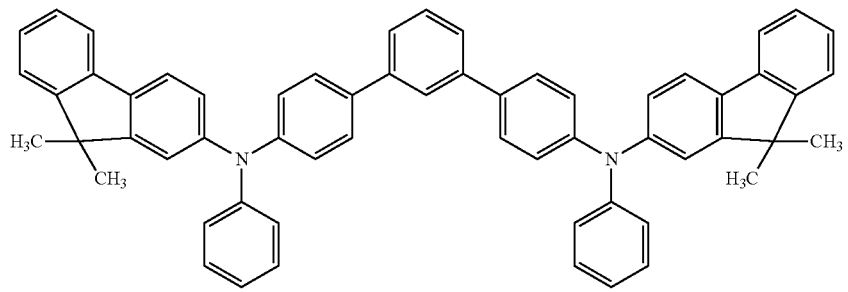

(1-34)

The structure of the obtained white powder was identified using NMR.
The following 48 hydrogen signals were detected with $^1$H-NMR (CDCl$_3$).
δ (ppm)=7.84 (1H)
7.70-7.03 (35H)
1.48 (12H)

Synthesis Example 7

Synthesis of an Arylamine Derivative (Compound 1-37)

a total of 11.7 g (yield 73%) of a white powder of an arylamine derivative (Compound 1-37) to be used for forming the second hole transport layer was obtained by the same operations as in Synthesis Example 5 by using N-(9,9-dimethyl-9H-fluoren-2-yl)-N-(2"-bromo-1,1':4',1"-terphenyl-4-yl)aniline and N-(biphenyl-4-yl)aniline instead of N-(biphenyl-4-yl)-N-(2"-bromo-1,1':4',1"-terphenyl-4-yl)aniline and 2-(phenylamino)-9,9-dimethyl-9H-fluorene.

This arylamine derivative (Compound 1-37) is 2-{(biphenyl-4-yl)-phenylamino}-4"-{(9,9-dimethyl-9H-fluoren-2-yl)-phenylamino}-1,1':4',1"-terphenyl, which is represented by the following formula.

(1-37)

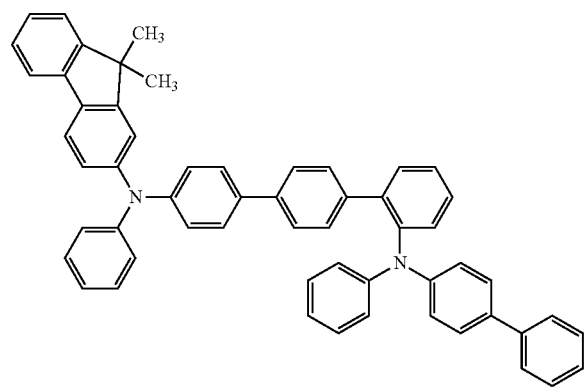

The structure of the obtained white powder was identified using NMR.

The following 44 hydrogen signals were detected with $^1$H-NMR (CDCl$_3$).

δ (ppm)=7.68 (1H)

7.64-6.84 (37H)

1.48 (6H)

Synthesis Example 8

Synthesis of an Arylamine Derivative (Compound 1-38)

a total of 6.6 g (yield 39%) of a white powder of an arylamine derivative (Compound 1-38) to be used for forming the second hole transport layer was obtained by the same operations as in Synthesis Example 3, except that 1,2-diiodobenzene and 4-{(9,9-dimethyl-9H-fluoren-2-yl)-phenylamino}-phenylboronic acid were used instead of 1,4-dibromobenzene and N-(biphenyl-4-yl)-N-{3-(4,4,5,5-tetramethyl-[1,3,2]dioxaboran-2-yl)phenyl}aniline.

This arylamine derivative (Compound 1-38) is 4,4"-bis{(9,9-dimethyl-9H-fluoren-2-yl)-phenylamino}-1,1':2',1"-terphenyl, which is represented by the following formula.

(1-38)

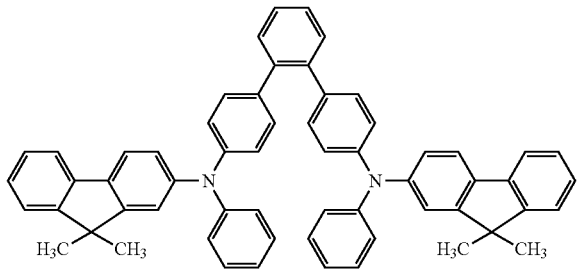

The structure of the obtained white powder was identified using NMR.

The following 48 hydrogen signals were detected with $^1$H-NMR (CDCl$_3$).

δ (ppm)=7.64 (2H)

7.58 (2H)

7.45-6.99 (32H)

1.38 (12H)

Synthesis Example 9

Synthesis of an Arylamine Derivative (Compound 1-39)

a total of 4.6 g (yield 24%) of a white powder of an arylamine derivative (Compound 1-39) to be used for forming the second hole transport layer was obtained by the same operations as in Synthesis Example 3, except that 1,2-diiodobenzene and 4-{bis(biphenyl-4-yl)amino}-phenylboronic acid were used instead of 1,4-dibromobenzene and N-(biphenyl-4-yl)-N-{3-(4,4,5,5-tetramethyl-[1,3,2]dioxaboran-2-yl)phenyl}aniline.

This arylamine derivative (Compound 1-39) is 4,4"-bis{bis(biphenyl-4-yl)amino}-1,1':2',1"-terphenyl, which is represented by the following formula.

(1-39)

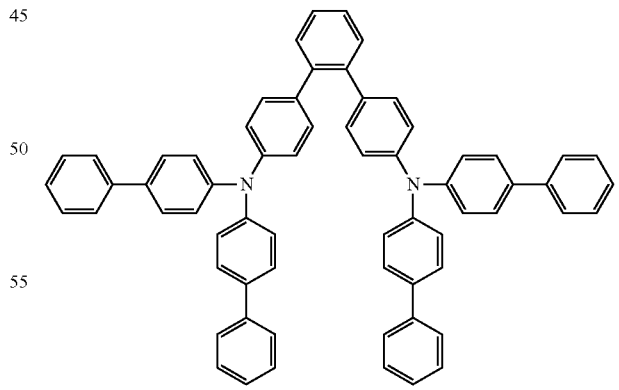

The structure of the obtained white powder was identified using NMR.

The following 48 hydrogen signals were detected with $^1$H-NMR (CDCl$_3$).

δ (ppm)=7.57-7.28 (32H)

7.21 (8H)

7.11 (8H)

Synthesis Example 10

Synthesis of an Arylamine Derivative (Compound 1-41)

a total of 5.0 g (yield 30%) of a white powder of an arylamine derivative (Compound 1-41) to be used for forming the second hole transport layer was obtained by the same operations as in Synthesis Example 6, except that
4,4"-dibromo-1,1':2',1"-terphenyl and
(biphenyl-4-yl)-(naphthalen-1-yl)amine
were used instead of
4,4"-dibromo-1,1':3',1"-terphenyl and
2-(phenylamino)-9,9-dimethyl-9H-fluorene.

This arylamine derivative (Compound 1-41) is 4,4"-bis{(biphenyl-4-yl)-(naphthalen-1-yl)amino}-1,1':2',1"-terphenyl, which is represented by the following formula.

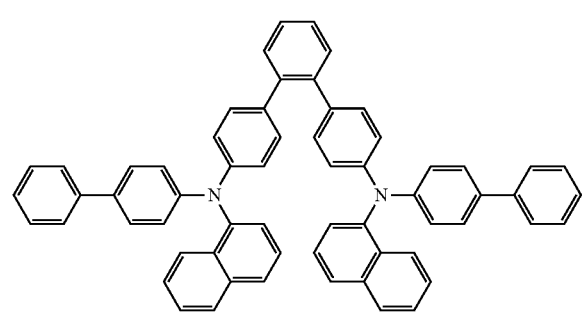

(1-41)

The structure of the obtained white powder was identified using NMR.
The following 44 hydrogen signals were detected with $^1$H-NMR (CDCl$_3$).
δ (ppm)=7.93-7.84 (4H)
7.79 (2H)
7.60-7.26 (24H)
7.25-6.92 (14H)

Synthesis Example 11

Synthesis of an Arylamine Derivative (Compound 1-42)

a total of 7.3 g (yield 43%) of a white powder of an arylamine derivative (Compound 1-42) to be used for forming the second hole transport layer was obtained by the same operations as in Synthesis Example 6, except that
4,4"-dibromo-1,1':2',1"-terphenyl and
N-{4-(naphthalen-1-yl)phenyl}aniline
were used instead of
4,4"-dibromo-1,1':3',1"-terphenyl and
2-(phenylamino)-9,9-dimethyl-9H-fluorene.

This arylamine derivative (Compound 1-42) is 4,4"-bis[{4-(naphthalen-1-yl)phenyl}-phenylamino]-1,1':2',1"-terphenyl, which is represented by the following formula.

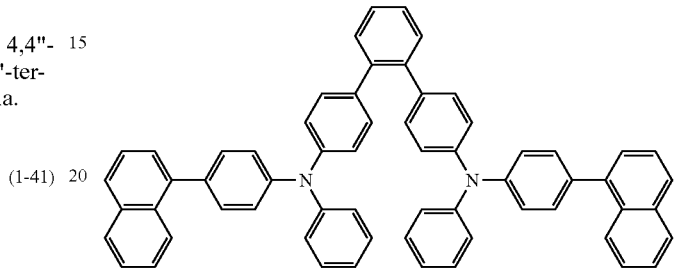

(1-42)

The structure of the obtained white powder was identified using NMR.
The following 44 hydrogen signals were detected with $^1$H-NMR (CDCl$_3$).
δ (ppm)=8.01 (2H)
7.91 (2H)
7.84 (2H)
7.53-6.98 (38H)

Synthesis Example 12

Synthesis of an Arylamine Derivative (Compound 1-45)

a total of 16.7 g (yield 79%) of a white powder of an arylamine derivative (Compound 1-45) to be used for forming the second hole transport layer was obtained by the same operations as in Synthesis Example 6, except that
4,4"-dibromo-1,1':3',1"-terphenyl and
N-{4-(naphthalen-1-yl)phenyl}aniline
were used instead of
4,4"-dibromo-1,1':3',1"-terphenyl and
2-(phenylamino)-9,9-dimethyl-9H-fluorene.

This arylamine derivative (Compound 1-45) is 4,4"-bis[{4-(naphthalen-1-yl)phenyl}-phenylamino]-1,1':3',1"-terphenyl, which is represented by the following formula.

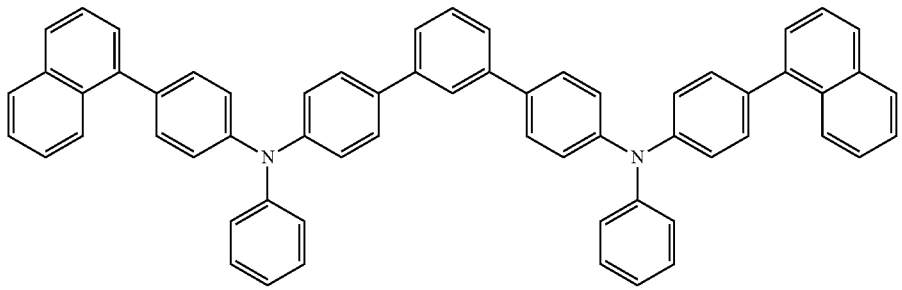

(1-45)

The structure of the obtained white powder was identified using NMR.

The following 44 hydrogen signals were detected with $^1$H-NMR (CDCl$_3$).

δ (ppm)=8.08 (2H)
7.94 (2H)
7.90-7.80 (3H)
7.65-7.00 (37H)

Synthesis Example 13

Synthesis of an Arylamine Derivative (Compound 1-47)

a total of 4.2 g (yield 25%) of a white powder of an arylamine derivative (Compound 1-47) to be used for forming the second hole transport layer was obtained by the same operations as in Synthesis Example 3, except that
1,3-diiodobenzene and
2-{(9,9-dimethyl-9H-fluoren-2-yl)-phenylamino}-phenylboronic acid
were used instead of
1,4-dibromobenzene and
N-(biphenyl-4-yl)-N-{3-(4,4,5,5-tetramethyl-[1,3,2]dioxaboran-2-yl)phenyl}aniline.

This arylamine derivative (Compound 1-47) is 2,2"-bis{(9,9-dimethyl-9H-fluoren-2-yl)-phenylamino}-1,1':3',1"-terphenyl, which is represented by the following formula.

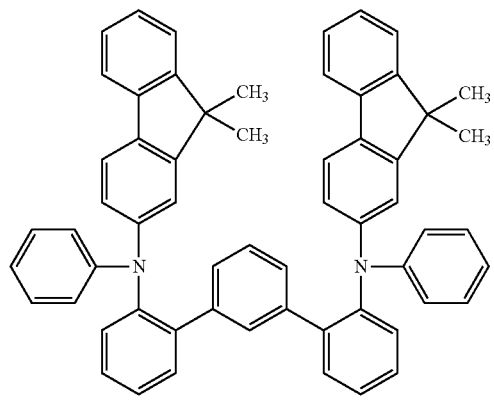

(1-47)

The structure of the obtained white powder was identified using NMR.

The following 48 hydrogen signals were detected with $^1$H-NMR (CDCl$_3$).

δ (ppm)=7.60 (2H)
7.38-7.09 (14H)
6.95-6.71 (14H)
6.66-6.56 (4H)
6.35 (2H)
1.26 (12H)

Synthesis Example 14

Synthesis of an Arylamine Derivative (Compound 1-49)

a total of 13.7 g (yield 76%) of a white powder of an arylamine derivative (Compound 1-49) to be used for forming the second hole transport layer was obtained by the same operations as in Synthesis Example 3, except that
2-{(9,9-dimethyl-9H-fluoren-2-yl)-phenylamino}-phenylboronic acid
was used instead of
N-(biphenyl-4-yl)-N-{3-(4,4,5,5-tetramethyl-[1,3,2]dioxaboran-2-yl)phenyl}aniline.

This arylamine derivative (Compound 1-49) is 2,2"-bis{(9,9-dimethyl-9H-fluoren-2-yl)-phenylamino}-1,1':4',1"-terphenyl, which is represented by the following formula.

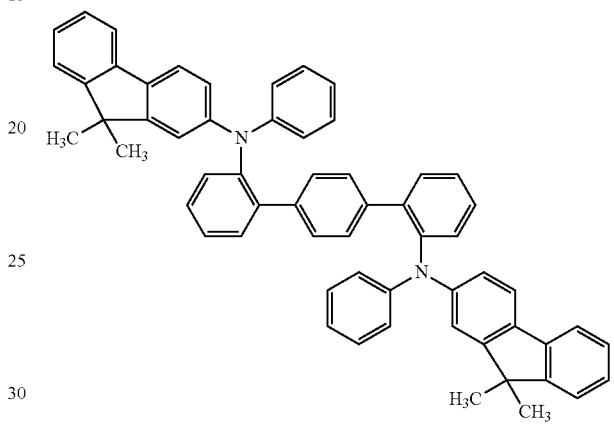

(1-49)

The structure of the obtained white powder was identified using NMR.

The following 48 hydrogen signals were detected with $^1$H-NMR (THF-d$_8$).

δ (ppm)=7.53 (2H)
7.35-6.81 (30H)
6.76 (2H)
6.67 (2H)
1.29 (12H)

Synthesis Example 15

Synthesis of an Arylamine Derivative (Compound 1-88)

a total of 11.4 g (yield 74%) of a white powder of an arylamine derivative (Compound 1-88) to be used for forming the second hole transport layer was obtained by the same operations as in Synthesis Example 6, except that
4,4"-diiodo-1,1':4',1"-terphenyl and
N-(triphenylen-2-yl)aniline
were used instead of
4,4"-dibromo-1,1':3',1"-terphenyl and
2-(phenylamino)-9,9-dimethyl-9H-fluorene.

This arylamine derivative (Compound 1-88) is 4,4"-bis{(triphenylen-2-yl)-phenylamino}-1,1':4',1"-terphenyl, which is represented by the following formula.

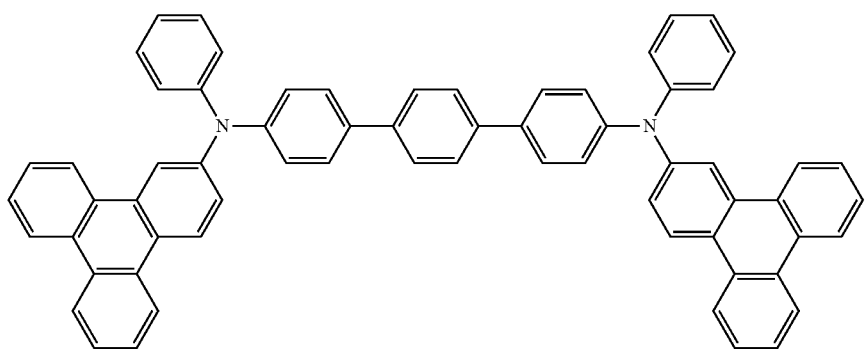

(1-88)

The structure of the obtained white powder was identified using NMR.

The following 44 hydrogen signals were detected with $^1$H-NMR (THF-$d_8$).

δ (ppm)=8.72-8.62 (8H)
   8.45 (2H)
   8.36 (2H)
   7.75 (4H)
   7.70-7.21 (26H)
   7.09 (2H)

Synthesis Example 16

Synthesis of an Arylamine Derivative (Compound 1-91)

a total of 6.80 g (yield 67%) of a light-yellow powder of an arylamine derivative (Compound 1-91) to be used for forming the second hole transport layer was obtained by the same operations as in Synthesis Example 1, except that N-(4'-bromo-1,1'-biphenyl-4-yl)-N-{4-(1-phenyl-indol-4-yl)phenyl}aniline and
{4-(4,4,5,5-tetramethyl-1,3,2-dioxaboran-2-yl)phenyl}-(biphenyl-4-yl)
were used instead of
N-(biphenyl-4-yl)-N-(4-bromophenyl)aniline and
N-(9,9-dimethyl-9H-fluoren-2-yl)-N-{3'-(4,4,5,5-tetramethyl-[1,3,2]dioxaboran-2-yl)biphenyl-4-yl}aniline.

This arylamine derivative (Compound 1-91) is 4-{(biphenyl-4-yl)-phenylamino}-4''-[{4-(1-phenyl-indol-4-yl)phenyl}-phenylamino]-1,1':4',1''-terphenyl, which is represented by the following formula.

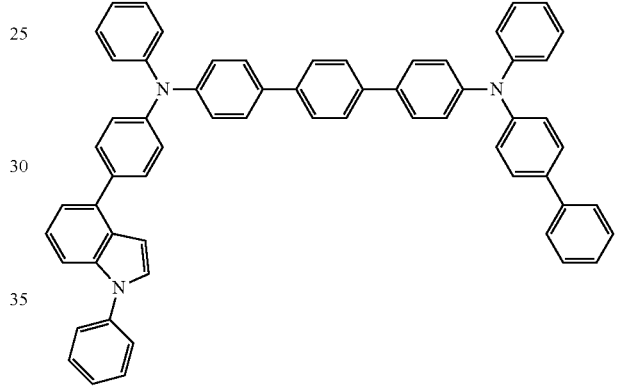

(1-91)

The structure of the obtained white powder was identified using NMR.

The following 45 hydrogen signals were detected with $^1$H-NMR (THF-$d_8$).

δ (ppm)=7.70 (4H)
   7.68-7.50 (16H)
   7.42-7.11 (23H)
   7.05 (1H)
   6.88 (1H)

Synthesis Example 17

Synthesis of an Arylamine Derivative (Compound 1-92)

the following components were added to a nitrogen-purged reactor, heated, and stirred for 24 h at 210° C.

| | |
|---|---|
| 4,4''-diiodo-1,1':4',1''-terphenyl | 13.0 g, |
| N-phenyl-N-(2-phenylbiphenyl-4-yl) aniline | 20.0 g, |
| copper powder | 0.18 g, |
| potassium carbonate | 11.3 g, |
| 3,5-di-tert-butylsalicylic acid | 0.7 g, |
| sodium hydrogensulfite and | 0.86 g, |
| dodecylbenzene | 30 mL. |

Then, after cooling,

-continued

| | |
|---|---|
| xylene and methanol | 30 mL, 60 mL | were added, and the precipitate was collected by filtration. A total of 250 mL of toluene and 20 g of silica were added to the precipitate, followed by heating to 90° C. Insolubles were then removed by hot filtration. After concentration, a crude product precipitated by the addition of ethyl acetate and methanol was collected by filtration.

This crude product was recrystallized using chlorobenzene, and then a reflux washing operation using methanol was performed to obtain 16.9 g (yield 72%) of a white powder of an arylamine derivative (Compound 1-92) to be used for forming the second hole transport layer.

This arylamine derivative is 4,4"-bis{(2-phenylbiphenyl-4-yl)-phenylamino}-1,1':4',1"-terphenyl, which is represented by the following formula.

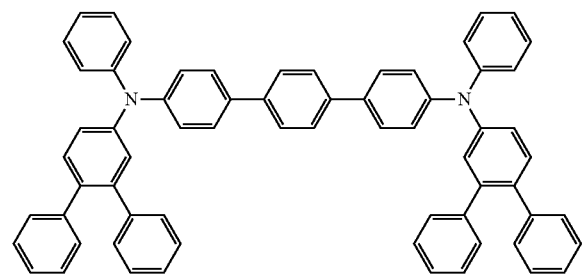

(1-92)

The structure of the obtained white powder was identified using NMR.

The following 48 hydrogen signals were detected with ¹H-NMR (CDCl₃).

δ (ppm)=7.68 (4H)
7.62-7.55 (4H)
7.39-7.06 (40H)

Synthesis Example 18

Synthesis of an Arylamine Derivative (Compound 1-93)

a total of 4.3 g (yield 42%) of a white powder of an arylamine derivative (Compound 1-93) to be used for forming the second hole transport layer was obtained by the same operations as in Synthesis Example 6, except that 4,4"-dibromo-1,1':2',1"-terphenyl and N-(2-phenylbiphenyl-4-yl)aniline were used instead of 4,4"-dibromo-1,1':3',1"-terphenyl and 2-(phenylamino)-9,9-dimethyl-9H-fluorene.

This arylamine derivative is 4,4"-bis{(2-phenylbiphenyl-4-yl)-phenylamino}-1,1':2',1"-terphenyl, which is represented by the following formula.

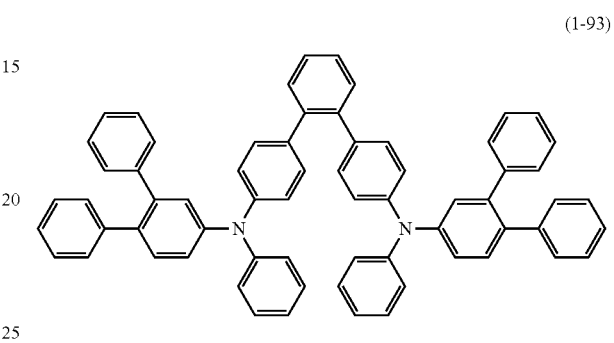

(1-93)

The structure of the obtained white powder was identified using NMR.

The following 48 hydrogen signals were detected with ¹H-NMR (CDCl₃).

δ (ppm)=7.50-7.39 (4H)
7.31-6.97 (44H)

Synthesis Example 19

Synthesis of an Arylamine Derivative (Compound 1-94)

a total of 7.7 g (yield 53%) of a white powder of an arylamine derivative (Compound 1-94) to be used for forming the second hole transport layer was obtained by the same operations as in Synthesis Example 6, except that N-(2-phenylbiphenyl-4-yl)aniline was used instead of 2-(phenylamino)-9,9-dimethyl-9H-fluorene.

This arylamine derivative is 4,4"-bis{(2-phenylbiphenyl-4-yl)-phenylamino}-1,1':3',1"-terphenyl, which is represented by the following formula.

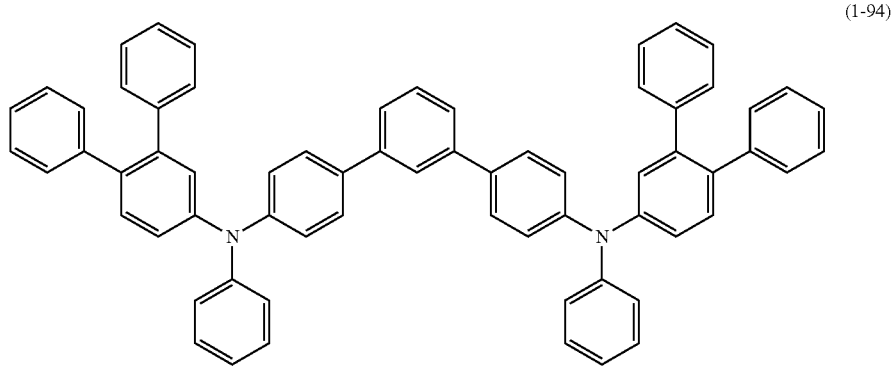 [SMILES: c1ccc(-c2ccc(N(c3ccccc3)c3ccc(-c4cccc(-c5ccc(N(c6ccccc6)c6ccc(-c7ccccc7)c(-c7ccccc7)c6)cc5)c4)cc3)cc2-c2ccccc2)cc1]

(1-94)

The structure of the obtained white powder was identified using NMR.

The following 48 hydrogen signals were detected with $^1$H-NMR (CDCl$_3$).

δ (ppm)=7.81 (2H)

7.61-7.48 (14H)

7.39-7.06 (32H)

Physical Property Evaluation Test 1

The glass transition temperature of the arylamine derivatives synthesized in the synthesis examples was determined with a high-sensitivity differential scanning calorimeter (DSC3100S, manufactured by Bruker AXS K.K.). The results are presented below.

|  | Glass transition temperature |
|---|---|
| Compound (1-5) of Synthesis Example 1 | 117° C. |
| Compound (1-6) of Synthesis Example 2 | 117° C. |
| Compound (1-21) of Synthesis Example 3 | 103° C. |
| Compound (1-32) of Synthesis Example 5 | 115° C. |
| Compound (1-34) of Synthesis Example 6 | 124° C. |
| Compound (1-37) of Synthesis Example 7 | 114° C. |
| Compound (1-38) of Synthesis Example 8 | 119° C. |
| Compound (1-39) of Synthesis Example 9 | 106° C. |
| Compound (1-41) of Synthesis Example 10 | 127° C. |
| Compound (1-42) of Synthesis Example 11 | 111° C. |
| Compound (1-45) of Synthesis Example 12 | 122° C. |
| Compound (1-47) of Synthesis Example 13 | 116° C. |
| Compound (1-49) of Synthesis Example 14 | 117° C. |
| Compound (1-88) of Synthesis Example 15 | 163° C. |
| Compound (1-91) of Synthesis Example 16 | 125° C. |
| Compound (1-92) of Synthesis Example 17 | 124° C. |
| Compound (1-93) of Synthesis Example 18 | 115° C. |
| Compound (1-94) of Synthesis Example 19 | 122° C. |

The results presented hereinabove indicate that the arylamine derivative represented by the general formula (1) has a glass transition temperature of 100° C. or higher, and particularly preferably a high glass transition temperature of 110° C. or higher. It can be found from these results that the arylamine derivative has a stable thin-film state.

Physical Property Evaluation Test 2

A vapor-deposited film with a thickness of 100 nm was produced on an ITO substrate by using the arylamine derivatives synthesized in the synthesis examples, and the work function was measured with an ionization potential measuring device (PYS-202, manufactured by Sumitomo Heavy Industries, Ltd.).

The results are presented below.

|  | Work function |
|---|---|
| Compound (1-5) of Synthesis Example 1 | 5.68 eV |
| Compound (1-6) of Synthesis Example 2 | 5.65 eV |
| Compound (1-21) of Synthesis Example 3 | 5.79 eV |
| Compound (1-22) of Synthesis Example 4 | 5.83 eV |
| Compound (1-32) of Synthesis Example 5 | 5.69 eV |
| Compound (1-34) of Synthesis Example 6 | 5.65 eV |
| Compound (1-37) of Synthesis Example 7 | 5.67 eV |
| Compound (1-38) of Synthesis Example 8 | 5.64 eV |
| Compound (1-39) of Synthesis Example 9 | 5.66 eV |
| Compound (1-41) of Synthesis Example 10 | 5.69 eV |
| Compound (1-42) of Synthesis Example 11 | 5.75 eV |
| Compound (1-45) of Synthesis Example 12 | 5.76 eV |
| Compound (1-47) of Synthesis Example 13 | 5.72 eV |
| Compound (1-49) of Synthesis Example 14 | 5.72 eV |
| Compound (1-88) of Synthesis Example 15 | 5.62 eV |
| Compound (1-91) of Synthesis Example 16 | 5.67 eV |
| Compound (1-92) of Synthesis Example 17 | 5.67 eV |
| Compound (1-93) of Synthesis Example 18 | 5.75 eV |
| Compound (1-94) of Synthesis Example 19 | 5.76 eV |

The results presented hereinabove indicate that the arylamine derivative represented by the general formula (1) shows an advantageous energy level and has a satisfactory hole transport capability when compared with the work function of 5.4 eV of the typical hole transport material such as NPD and TPD.

Example 1

The organic EL device with the device configuration shown in FIG. 1 was fabricated by performing vapor deposition according to the following procedure.

First, an ITO-attached glass substrate in which an ITO electrode (a transparent anode 2) with a film thickness of 150 nm was formed on a glass substrate (transparent substrate) 1 was prepared.

The glass substrate 1 was ultrasonically cleaned for 20 min in isopropyl alcohol and then dried for 10 min on a hot plate heated to 200° C. UV ozone treatment was then performed for 15 min, the ITO-attached glass substrate was attached inside a vacuum vapor deposition device, and the device was depressurized to 0.001 Pa or less.

Compound (HIM-1) of the following structural formula was then formed as a hole injection layer 3 to a film thickness of 5 nm so as to cover the transparent anode 2.

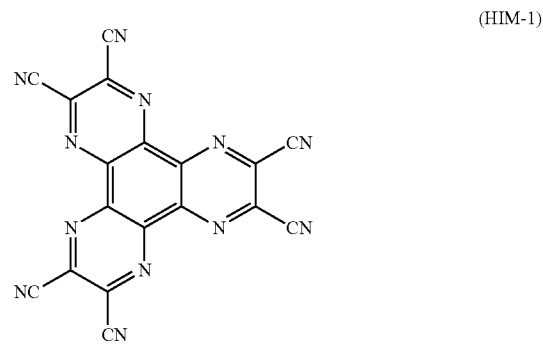 [SMILES: N#Cc1nc2c3nc(C#N)c(C#N)nc3c3nc(C#N)c(C#N)nc3c2nc1C#N]

(HIM-1)

A first hole transport layer 4 with a film thickness of 60 nm was formed on the hole injection layer 3 by using a di(triarylamine) compound (5-1) having two triphenylamine skeletons in a molecule.

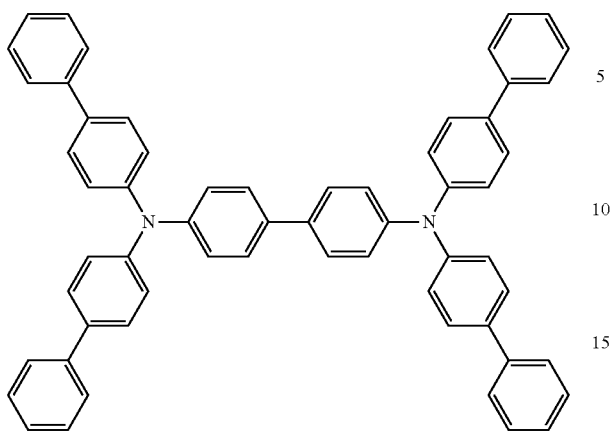

(5-1)

A second hole transport layer 5 with a film thickness of 5 nm was formed on the first hole transport layer 4, which has been thus formed, by using the following arylamine derivative (Compound 1-5) synthesized in Synthesis Example 1.

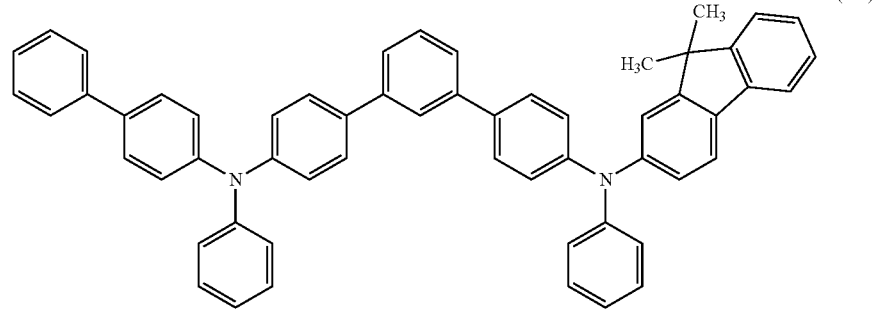

(1-5)

A luminous layer 6 with a film thickness of 20 nm was formed on the second hole transport layer 5 by binary vapor deposition of Compound (EMD-1) and Compound (EMH-1) of the following structural formulas at vapor deposition rates such that the vapor deposition rate ratio of EMD-1 to EMH-1 was 5:95.

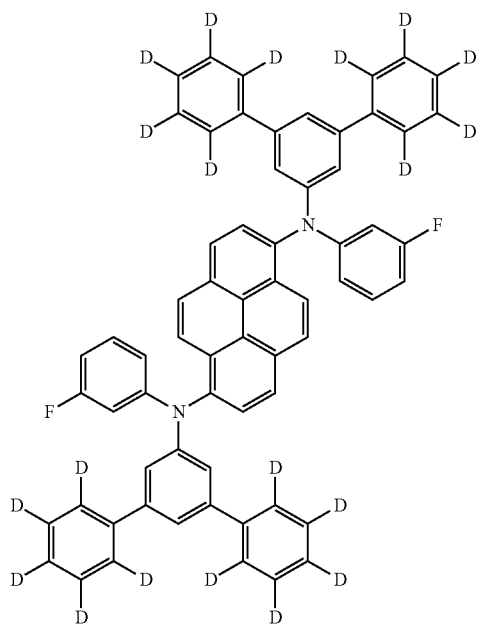

(EMD-1)

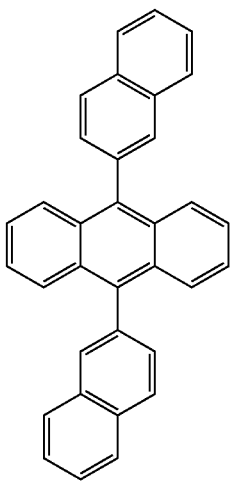

(EMH-1)

An electron transport layer 7 with a film thickness of 30 nm was then formed on the luminous layer 6 by binary vapor deposition of a pyrimidine compound (2-92) of the following structural formula and a compound ETM-1 of the following structural formula at vapor deposition rates such that the vapor deposition rate ratio of Compound (2-92) to ETM-1 was 50:50.

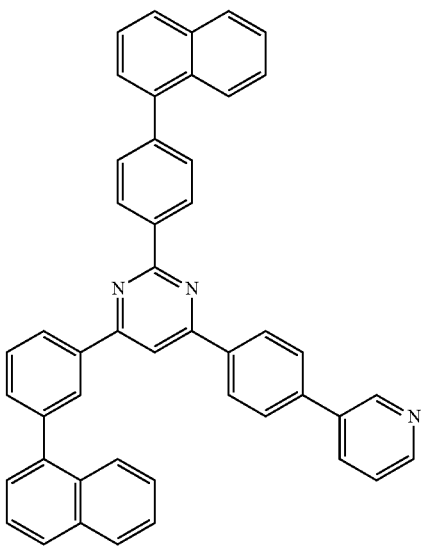

(2-92)

(ETM-1)

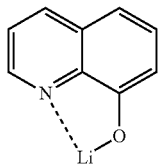

An electron injection layer 8 with a film thickness of 1 nm was then formed on the electron transport layer 7 by using lithium fluoride.

Finally, aluminum was vapor deposited to a film thickness of 100 nm to form the cathode 9 on the electron injection layer 8.

Characteristics of the organic EL device fabricated in the above-described manner were measured at normal temperature in the atmosphere.

The materials used to form the first hole transport layer, second hole transport layer, luminous layer, and electron transport layer in the fabricated organic EL device are shown in Table 1. The measurement results on light emission characteristics and device life which were obtained when a direct current voltage was applied to the organic EL device are shown in Table 2.

The device life was measured as a time till the emission luminance attenuated to 1900 cd/m² (corresponds to 95% when the initial luminance is 100%; 95% attenuation) when a constant-current drive was performed at an emission luminance at the emission start time (initial luminance) of 2000 cd/m².

Example 2

An organic EL device was fabricated in the same manner as in Example 1, except that the second hole transport layer 5 with a film thickness of 5 nm was formed using the arylamine derivative (1-41) synthesized in Synthesis Example 10, and light emission characteristics and device life thereof were measured.

(1-41)

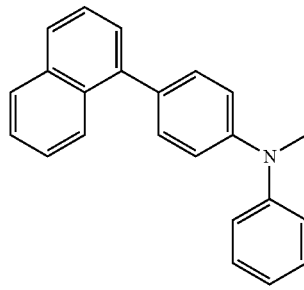

The materials used to form the first hole transport layer, second hole transport layer, luminous layer, and electron transport layer in the fabricated organic EL device are shown in Table 1. The measurement results on light emission characteristics and device life are shown in Table 2.

Example 3

An organic EL device was fabricated in the same manner as in Example 1, except that the second hole transport layer 5 with a film thickness of 5 nm was formed using the arylamine derivative (1-45) synthesized in Synthesis Example 12, and light emission characteristics and device life thereof were measured.

(1-45)

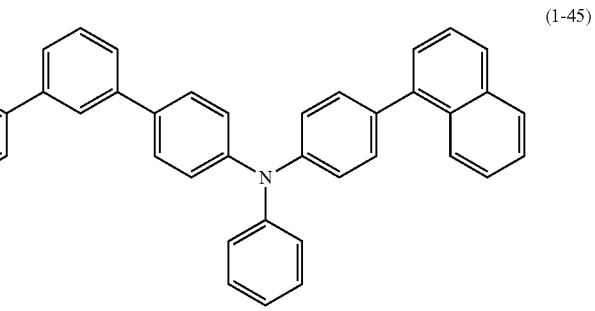

The materials used to form the first hole transport layer, second hole transport layer, luminous layer, and electron transport layer in the fabricated organic EL device are shown in Table 1. The measurement results on light emission characteristics and device life are shown in Table 2.

Example 4

An organic EL device was fabricated in the same manner as in Example 1, except that the second hole transport layer 5 with a film thickness of 5 nm was formed using the arylamine derivative (1-92) synthesized in Synthesis Example 17, and light emission characteristics and device life thereof were measured.

(1-92)

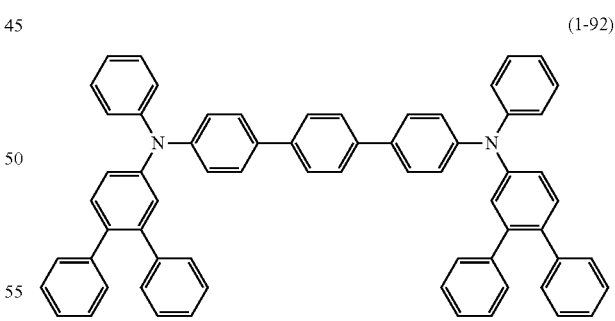

The materials used to form the first hole transport layer, second hole transport layer, luminous layer, and electron transport layer in the fabricated organic EL device are shown in Table 1. The measurement results on light emission characteristics and device life are shown in Table 2.

Example 5

An organic EL device was fabricated in the same manner as in Example 1, except that the electron transport layer 7 with a film thickness of 30 nm was formed by using a pyrimidine compound (2-123) of the following structural formula as a material for the electron transport layer 7 and performing binary vapor deposition of the pyrimidine compound (2-123) and Compound (ETM-1) at vapor deposition rates such that the vapor deposition rate ratio of Compound (2-123) to ETM-1 was 50:50, and light emission characteristics and device life thereof were measured.

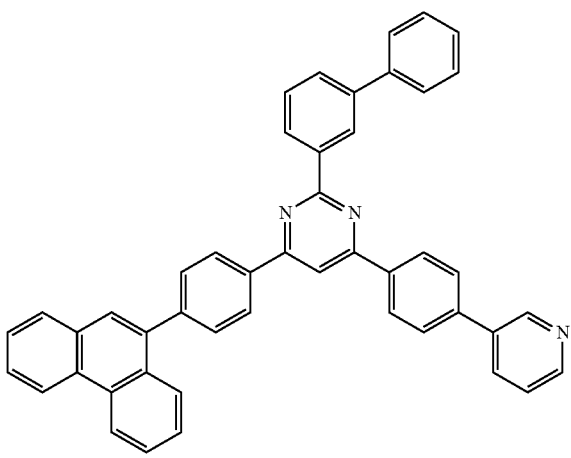

(2-123)

The materials used to form the first hole transport layer, second hole transport layer, luminous layer, and electron transport layer in the fabricated organic EL device are shown in Table 1. The measurement results on light emission characteristics and device life are shown in Table 2.

Example 6

An organic EL device was fabricated in the same manner as in Example 2, except that the electron transport layer 7 with a film thickness of 30 nm was formed by using the pyrimidine compound (2-123) of the structural formula indicated above as a material for the electron transport layer 7 and performing binary vapor deposition of the pyrimidine compound (2-123) and Compound (ETM-1) at vapor deposition rates such that the vapor deposition rate ratio of Compound (2-123) to ETM-1 was 50:50, and light emission characteristics and device life thereof were measured.

The materials used to form the first hole transport layer, second hole transport layer, luminous layer, and electron transport layer in the fabricated organic EL device are shown in Table 1. The measurement results on light emission characteristics and device life are shown in Table 2.

Example 7

An organic EL device was fabricated in the same manner as in Example 3, except that the electron transport layer 7 with a film thickness of 30 nm was formed by using the pyrimidine compound (2-123) of the structural formula indicated above as a material for the electron transport layer 7 and performing binary vapor deposition of the pyrimidine compound (2-123) and Compound (ETM-1) at vapor deposition rates such that the vapor deposition rate ratio of Compound (2-123) to ETM-1 was 50:50, and light emission characteristics and device life thereof were measured.

The materials used to form the first hole transport layer, second hole transport layer, luminous layer, and electron transport layer in the fabricated organic EL device are shown in Table 1. The measurement results on light emission characteristics and device life are shown in Table 2.

Example 8

An organic EL device was fabricated in the same manner as in Example 4, except that the electron transport layer 7 with a film thickness of 30 nm was formed by using the pyrimidine compound (2-123) of the structural formula indicated above as a material for the electron transport layer 7 and performing binary vapor deposition of the pyrimidine compound (2-123) and Compound (ETM-1) at vapor deposition rates such that the vapor deposition rate ratio of Compound (2-123) to ETM-1 was 50:50, and light emission characteristics and device life thereof were measured.

The materials used to form the first hole transport layer, second hole transport layer, luminous layer, and electron transport layer in the fabricated organic EL device are shown in Table 1. The measurement results on light emission characteristics and device life are shown in Table 2.

Comparative Example 1

An organic EL device was fabricated in the same manner as in Example 1, except that the second hole transport layer 4 with a film thickness of 5 nm was formed by using a di(triarylamine) compound (5-1) without using the arylamine derivative (Compound 1-5) synthesized in Synthesis Example 1, and light emission characteristics and device life thereof were measured.

The materials used to form the first hole transport layer, second hole transport layer, luminous layer, and electron transport layer in the fabricated organic EL device are shown in Table 1. The measurement results on light emission characteristics and device life are shown in Table 2.

Comparative Example 2

An organic EL device was fabricated in the same manner as in Comparative Example 1, except that the electron transport layer 7 with a film thickness of 30 nm was formed by using the pyrimidine compound (2-123) of the structural formula indicated above as a material for the electron transport layer 7 and performing binary vapor deposition of the pyrimidine compound (2-123) and Compound (ETM-1) at vapor deposition rates such that the vapor deposition rate ratio of Compound (2-123) to ETM-1 was 50:50, and light emission characteristics and device life thereof were measured.

The materials used to form the first hole transport layer, second hole transport layer, luminous layer, and electron transport layer in the fabricated organic EL device are shown in Table 1. The measurement results on light emission characteristics and device life are shown in Table 2.

Comparative Example 3

An anthracene compound (ETM-2) represented by the following formula and disclosed in WO 2003/060956) or the like was prepared as a material for the electron transport layer 7.

(ETM-2)

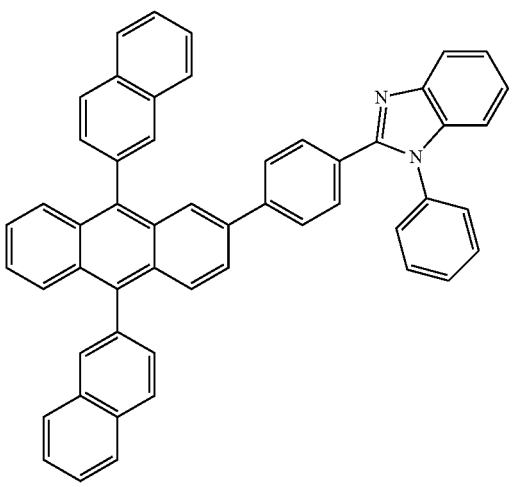

An organic EL device was fabricated under the same conditions as in Comparative Example 1, except that the electron transport layer with a film thickness of 30 nm was formed by performing binary vapor deposition of the anthracene compound (ETM-2) and Compound (ETM-1) at vapor deposition rates such that the vapor deposition rate ratio of ETM-2 to ETM-1 was 50:50, and light emission characteristics and device life thereof were measured.

The materials used to form the first hole transport layer, second hole transport layer, luminous layer, and electron transport layer in the fabricated organic EL device are shown in Table 1. The measurement results on light emission characteristics and device life are shown in Table 2.

Characteristics of the fabricated organic EL device were measured at normal temperature in the atmosphere. The measurement results on light emission characteristics which were obtained when a direct current voltage was applied to the fabricated organic EL device are shown in Table 2.

TABLE 1

|  | First hole transport layer | Second hole transport layer | Luminous layer | Electron transport layer |
|---|---|---|---|---|
| Example 1 | Compound 5-1 | Compound 1-5 | EMD-1/EMH-1 | Compound 2-92/ETM-1 |
| Example 2 | Compound 5-1 | Compound 1-41 | EMD-1/EMH-1 | Compound 2-92/ETM-1 |
| Example 3 | Compound 5-1 | Compound 1-45 | EMD-1/EMH-1 | Compound 2-92/ETM-1 |
| Example 4 | Compound 5-1 | Compound 1-92 | EMD-1/EMH-1 | Compound 2-92/ETM-1 |
| Example 5 | Compound 5-1 | Compound 1-5 | EMD-1/EMH-1 | Compound 2-123/ETM-1 |
| Example 6 | Compound 5-1 | Compound 1-41 | EMD-1/EMH-1 | Compound 2-123/ETM-1 |
| Example 7 | Compound 5-1 | Compound 1-45 | EMD-1/EMH-1 | Compound 2-123/ETM-1 |
| Example 8 | Compound 5-1 | Compound 1-92 | EMD-1/EMH-1 | Compound 2-123/ETM-1 |
| Comp. Ex. 1 | Compound 5-1 | Compound 5-1 | EMD-1/EMH-1 | Compound 2-92/ETM-1 |
| Comp. Ex. 2 | Compound 5-1 | Compound 5-1 | EMD-1/EMH-1 | Compound 2-123/ETM-1 |
| Comp. Ex. 3 | Compound 5-1 | Compound 5-1 | EMD-1/EMH-1 | ETM-2/ETM-1 |

TABLE 2

|  | Voltage [V] (@10 mA/cm$^2$) | Luminance [cd/m$^2$] (@10 mA/cm$^2$) | Luminous efficiency [cd/A] (@10 mA/cm$^2$) | Power efficiency [lm/W] (@10 mA/cm$^2$) | Device life, 95% attenuation (h) |
|---|---|---|---|---|---|
| Example 1 | 3.83 | 838 | 8.37 | 6.95 | 166 |
| Example 2 | 3.85 | 860 | 8.59 | 7.09 | 191 |
| Example 3 | 3.85 | 874 | 8.73 | 7.21 | 200 |
| Example 4 | 3.80 | 843 | 8.43 | 6.97 | 278 |

TABLE 2-continued

|  | Voltage [V] (@10 mA/cm$^2$) | Luminance [cd/m$^2$] (@10 mA/cm$^2$) | Luminous efficiency [cd/A] (@10 mA/cm$^2$) | Power efficiency [lm/W] (@10 mA/cm$^2$) | Device life, 95% attenuation (h) |
|---|---|---|---|---|---|
| Example 5 | 3.77 | 840 | 8.40 | 7.01 | 150 |
| Example 6 | 3.78 | 848 | 8.47 | 7.05 | 177 |
| Example 7 | 3.79 | 860 | 8.60 | 7.14 | 185 |
| Example 8 | 3.77 | 841 | 8.41 | 7.01 | 230 |
| Comp. Ex. 1 | 3.76 | 795 | 7.95 | 6.65 | 83 |
| Comp. Ex. 2 | 3.69 | 796 | 7.96 | 6.78 | 87 |
| Comp. Ex. 3 | 3.84 | 635 | 6.35 | 5.20 | 55 |

As indicated by the test results (Table 2), in the organic EL device of Comparative Example 3 in which the electron transport layer is formed using the anthracene compound (ETM-2) which is a publicly known electron transport material, the luminous efficiency is 6.35 cd/A when a current with a current density of 10 mA/cm$^2$ flows in the device.

By contrast, in the organic EL device of Comparative Examples 1 and 2 in which the electron transport layer is formed using the pyrimidine compound represented by the general formula (2), the luminous efficiency is high such as 7.95 cd/A to 7.96 cd/A.

Further, in the organic EL devices of Examples 1 to 8 in which the second hole transport layer is formed using the arylamine derivative represented by the general formula (1) and also the electron transport layer is formed using the pyrimidine compound represented by the general formula (2), the luminous efficiency is even higher such as 8.37 cd/A to 8.73 cd/A.

Furthermore, as for the power efficiency, the organic EL device of Comparative Example 3 has 5.20 lm/W, whereas the organic EL devices of Comparative Examples 1 and 2 have higher values of 6.65 lm/W to 6.78 lm/W, and the organic EL devices of Examples 1 to 8 have even higher values of 6.95 lm/W to 7.21 lm/W.

Similar results are obtained also with respect to the device life (95% attenuation).

Thus, the device life of the organic EL device of Comparative Example 3 is 55 h, whereas the device life of the organic EL devices of Comparative Examples 1 and 2 is extended to 83 h to 87 h. It is also understood that in the organic EL devices of Examples 1 to 8, the device life is further greatly extended to 150 h to 278 h.

INDUSTRIAL APPLICABILITY

The organic EL device of the present invention in which a specific arylamine derivative and a specific pyrimidine compound are used as device materials has increased luminous efficiency and greatly improved durability and can be expected to be put to uses such as domestic electrical appliances and illumination.

DESCRIPTION OF REFERENCE NUMERALS

1 Glass substrate
2 Transparent anode
3 Hole injection layer
4 First hole transport layer
5 Second hole transport layer
6 Luminous layer
7 Electron transport layer
8 Electron injection layer
9 Cathode

The invention claimed is:

1. An organic electroluminescence device having an anode, a first hole transport layer, a second hole transport layer, a luminous layer, an electron transport layer, and a cathode in the order of description, wherein the second hole transport layer includes an arylamine derivative represented by any of the following formulas (1a-a), (1a-b), (1b-a), (1c-a), (1c-b), or (1c-c):

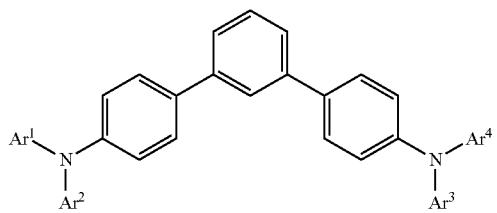
(1a-a)

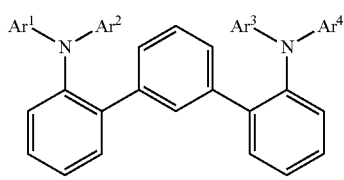
(1a-b)

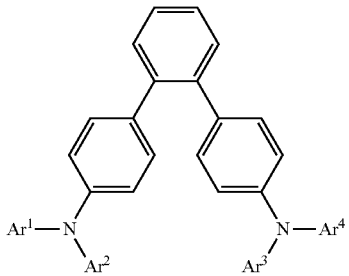
(1b-a)

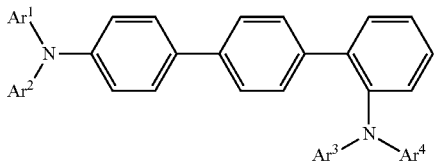
(1c-a)

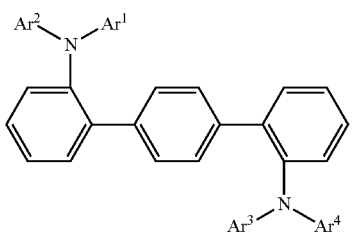
(1c-b)

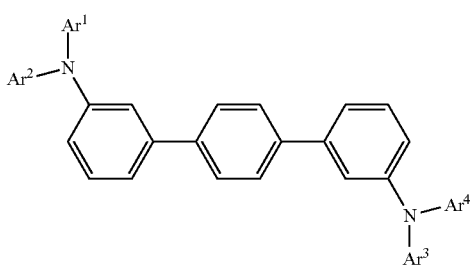
(1c-c)

wherein $Ar^1$ to $Ar^4$ are phenyl groups that may have a substituent, biphenyl groups that may have a substituent, terphenyl groups that may have a substituent, triphenylenyl groups that may have a substituent, or fluorenyl groups that may have a substituent, said substituent being an alkyl group, a naphthyl group, or an indolyl group, and the electron transport layer includes a pyrimidine compound represented by formula (2a)

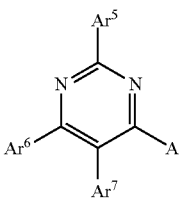
(2a)

wherein $Ar^5$ is a phenyl group or a phenyl group substituted with a naphthyl group, $Ar^6$ is a naphthyl group or a phenyl group substituted with a phenanthrenyl group, $Ar^7$ is a hydrogen atom, and A is a phenyl group substituted with a pyridyl group.

2. The organic electroluminescence device according to claim 1, wherein the first hole transport layer includes an arylamine compound having hole transport property and having a molecular structure different from that of the arylamine derivative included in the second hole transport layer.

3. The organic electroluminescence device according to claim 1, wherein the luminous layer includes a blue luminous dopant.

4. The organic electroluminescence device according to claim 3, wherein the blue luminous dopant is a pyrene derivative.

5. The organic electroluminescence device according to claim 1, wherein the luminous layer includes an anthracene derivative.

6. The organic electroluminescence device according to claim 5, wherein the anthracene derivative is a host material.

* * * * *